(12) United States Patent
Rishi et al.

(10) Patent No.: US 9,598,441 B2
(45) Date of Patent: Mar. 21, 2017

(54) THERAPEUTIC COMPOUNDS AND METHODS

(75) Inventors: Arun K. Rishi, Detroit, MI (US); Scott D. Larsen, Ann Arbor, MI (US)

(73) Assignees: Wayne State University, Detroit, MI (US); Regents of the University of Michigan, Ann Arbor, MI (US); Department of Veteran Affairs, Washington, DC (US)

( * ) Notice: Subject to any disclaimer, the term of this patent is extended or adjusted under 35 U.S.C. 154(b) by 71 days.

(21) Appl. No.: 14/239,881

(22) PCT Filed: Aug. 30, 2012

(86) PCT No.: PCT/US2012/053135
§ 371 (c)(1),
(2), (4) Date: Aug. 26, 2014

(87) PCT Pub. No.: WO2013/033392
PCT Pub. Date: Mar. 7, 2013

(65) Prior Publication Data
US 2014/0221412 A1    Aug. 7, 2014

Related U.S. Application Data

(60) Provisional application No. 61/529,144, filed on Aug. 30, 2011.

(51) Int. Cl.
C07D 513/10    (2006.01)
A61K 31/433    (2006.01)
C07D 513/20    (2006.01)

(52) U.S. Cl.
CPC .......... *C07D 513/10* (2013.01); *A61K 31/433* (2013.01); *C07D 513/20* (2013.01)

(58) Field of Classification Search
CPC .................................................. C07D 513/10
See application file for complete search history.

(56) References Cited

U.S. PATENT DOCUMENTS

| | | | |
|---|---|---|---|
| 4,559,157 A | 12/1985 | Smith | |
| 4,608,392 A | 8/1986 | Jacquet | |
| 4,820,508 A | 4/1989 | Wortzman | |
| 4,938,949 A | 7/1990 | Borch | |
| 4,992,478 A | 2/1991 | Geria | |
| 2004/0192739 A1 | 9/2004 | Solow-Cordero et al. | |
| 2005/0101518 A1 | 5/2005 | Solow-Cordero et al. | |
| 2008/0125469 A1 | 5/2008 | Bursavich et al. | |
| 2009/0163545 A1 | 6/2009 | Goldfarb | |
| 2010/0305106 A1* | 12/2010 | Dirusso ................ | A61K 31/404 514/218 |

FOREIGN PATENT DOCUMENTS

| | | | | |
|---|---|---|---|---|
| GB | WO 2005092304 A2 * | 10/2005 | ........... | A61K 31/433 |
| WO | WO 03/062392 A2 | 7/2003 | | |
| WO | WO 2005/092304 A2 | 10/2005 | | |
| WO | WO 2007/008529 A2 | 1/2007 | | |
| WO | WO 2007008529 A2 * | 1/2007 | ............ | A61K 31/15 |
| WO | WO 2007/146138 A2 | 12/2007 | | |
| WO | WO 2009/052288 A1 | 4/2009 | | |
| WO | WO 2009/137597 A1 | 11/2009 | | |

OTHER PUBLICATIONS

Luo et al. Cell, 2009, 136, pp. 823-837.*
Muthu et al. Oncotarget, 2015, 6, 6499-6510.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Patani et al. Chem. Rev. 1996, 96, 3147-3176.*
Puliyappadamba et al. J. Biol. Chem. 2011, 286, 38000-38017.*
Bursavich et al. Bioorg. Med. Chem. Lett. 2007, 17, 5630-5633.*
Alafeefy et al., "Development of certain novel N-(2-(2-(2-oxoindolin-3-ylidene) hydrazinecarbonyl)phenyl)-benzamides and 3-(2-oxoindolin-3-ylideneamino)-2-substituted quinazolin-4(3H)-ones as CFM-1 analogs: Design, Synthesis, QSAR analysis and anticancer activity", European Journal of Medicinal Chemistry (2015), doi: 10.1016/j.ejmech.2014.12.048.
Ali et al., "Potential antimicrobial agents-I: structural modifications and antimicrobial activity of some isatin derivatives", *Archives of Pharmacal Research*, 17(2), 131-133 (1994).
Ashour et al., "CARP-1 functional mimetics: A novel class of small molecule inhibitors of medulloblastoma cell growth", *PLoS One* 8(6), e66733 (2013).

(Continued)

*Primary Examiner* — Matthew Coughlin
(74) *Attorney, Agent, or Firm* — Viksnins Harris & Payds PLLP

(57) ABSTRACT

The invention provides compounds of formula I: and salts thereof. The invention also provides pharmaceutical compositions comprising a compound of formula I, processes for preparing compounds of formula I, intermediates useful for preparing compounds of formula I and therapeutic methods for treating cancer using compounds of formula I.

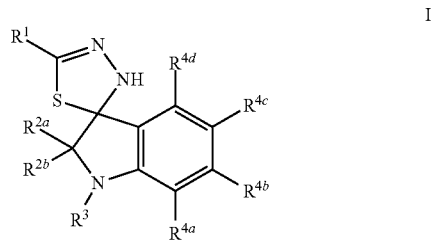

24 Claims, 22 Drawing Sheets

(56) References Cited

OTHER PUBLICATIONS

Ashour et al., "Mechanisms of inhibition of breast cancer cell growth and metastasis by novel small molecule compounds", Oral presentation at the 7th Middle East Best of CTRC-AACR San Antonio Breast Cancer Symposium, Riyadh, Saudi Arabia; Jan. 2013. [Abstract].

Ashour et al., "Mechanisms of inhibition of cancer cell growth and metastasis by novel small molecule compounds", American Association of Cancer Research (AACR) 104th Annual Meeting, Washington, DC, USA; Apr. 6-10, 2013. [Abstract].

Ashour et al., "Mechanisms of inhibition of cancer cell growth and metastasis by novel small molecule compounds", Department of Veterans Affairs Research & Development Program, John D. Dingell VA Medical Center, Detroit, MI Research Day (May 17, 2013). [Poster].

Ashour et al., "CARP-1 functional mimetics (CFMs): a novel class of small molecule inhibitors (SMIs) of medulloblastoma cell growth", American Association of Cancer Research (AACR) 104th Annual Meeting, Washington, DC, USA; Apr. 6-10, 2013. [Abstract].

Ashour et al., "CARP-1 functional mimetics (CFMs): a novel class of small molecule inhibitors (SMIs) of medulloblastoma cell growth", Department of Veterans Affairs Research & Development Program, John D. Dingell VA Medical Center, Detroit, MI Research Day (May 17, 2013). [Poster].

Bao et al., "Mechanisms of Malignant Pleural Mesothelioma Cell Growth Inhibition by Novel Small Molecule Compounds", Summer Undergraduate Research Experience, Cancer Biology Program, Karmanos Cancer Institute, Wayne State University; Aug. 2011. [Poster].

Beausoleil et al., "Large-scale characterization of HeLa cell nuclear phosphoproteins", *Proc Natl Acad Sci*, 101, 12130-12135 (2004).

Bursavich et al., "5'-Phenyl-3'H-spiro[indoline-3,2'-[1,3,4]thiadiazol]-2-one inhibitors of ADAMTS-5 (Aggrecanase-2)", *Bioorganic & Medicinal Chemistry Letters* 17, 5630-5633 (2007).

Carson et al., "Mechanisms of Neuroblastoma Cell Growth Inhibition by Novel Small Molecule Compounds", Summer Undergraduate Research Experience, Cancer Biology Program, Karmanos Cancer Institute, Wayne State University; Aug. 2013. [Poster].

Chao "Mechanisms of Cancer Cell Growth Inhibition by Novel Small Molecule Compounds", Summer Undergraduate Research Experience, Cancer Biology Program, Karmanos Cancer Institute, Wayne State University; Aug. 2012. [Poster].

Database Registry [Online] Chemical Abstracts Service; Accession No. 820228-36-2, XP002733188, 1 page, Jan. 26, 2005.

Dolowiec et al., "Mechanisms of Breast Cancer Cell Growth Inhibition by Novel Small Molecule Compounds", Summer Undergraduate Research Experience, Cancer Biology Program, Karmanos Cancer Institute, Wayne State University; Aug. 2010. [Poster].

Doyle et al., "A multidrug resistance transporter from human MCF-7 breast cancer cells", *Proc. Natl. Acad Sci* 95, 15665-15670 (1998).

Finley et al., "Interaction mating reveals binary and ternary connections between *Drosophila* cell cycle regulators", *Proc Natl Acad Sci* 91(26), 12980-12984 (1994).

Finley, "Targeting cyclin-dependent kinases in *Drosophila* with peptide aptamers", *Proc. Natl. Acad Sci* 95(24), 14266-14271 (1998).

Gyuris et al., "Cdi1, a human G1 and S phase protein phosphatase that associates with Cdk2", *Cell* 75, 791-803 (1993).

Hossain et al., "In Vitro Free Radical Scavenging Activity of Some β-Lactams and Phenolics", *International Journal of Pharmacy and Pharmaceutical Sciences*, vol. 2 (2), 60-63 (2010).

Inglese et al., "High-throughput screening assays for the identification of chemical probes", *Nat. Chem. Biol.* 3(8), 466-479 (2007).

Islam et al., "Cyclization of some isatin 3-thiosemicarbazones leading to D2-1,3,4-thiadiazolines and their selective deacetylation with hydrazine hydrate", *Journal of the Bangladesh Chemical Society*, 13(1 & 2), 149-155 (2000). English Abstract.

Islam et al, "Synthesis of 5-spiro(5'-methylisatin)-4-acetyl-2-(acetylamino)-D2-1,3,4-thiadiazoli ne and 5-spiro(5'-methylisatin)-4-acetyl-2-(5'methylisatin-3'-hydrazino)D2-1,3,4-thiadiazoline", *Indian Journal of Chemistry, Section B: Organic Chemistry Including Medicinal Chemistry*, 40B(3), 240-242 (2001). ISSN: 0376-4699; English.

Jamal et al., "CARP-1 functional mimetics are a novel class of small molecule inhibitors of malignant pleural mesothelioma cells", *PLoS One* 9 (3), e89146 (2014).

Jamal et al., "CARP-1 functional mimetics are a novel class of small molecule inhibitors of malignant pleural mesothelioma cells", American Association of Cancer Research (AACR) 105th Annual Meeting, San Diego, CA, USA; Apr. 5-9, 2014. [Abstract].

Jamal et al., "CARP-1 functional mimetics are a novel class of small molecule inhibitors of malignant pleural mesothelioma cells", Department of Veterans Affairs Research & Development Program, John D. Dingell VA Medical Center, Detroit, MI Research Day (May 23, 2014). [Poster].

Karim et al., "Synthesis of some isatin heterocycles as anticancer agents", *Journal of the Bangladesh Chemical Society* 18(2), 103-109 (2005). English Abstract.

Larina et al., "1H, 13C, 15N and 19F NMR study of acetylation products of heterocyclic thiosemicarbazones", *Magnetic Resonance in Chemistry*, vol. 45 (8), 667-673 (2007).

Levi et al., "Cell cycle and apoptosis regulatory protein (CARP)-1 is a novel, adriamycin-inducible, diffuse large B-cell lymphoma (DLBL) growth suppressor", *Can. Chemother Pharmacol.* 67(6), 1401-1413 (2011).

Mamun et al., "Microwave-assisted Efficient Synthesis of Isatins and spiro-Thiadiazolines under Green Chemistry Protocol" *J. Sci. Res.* 2 (2), 322-329 (2010).

Miller, "Xenograft models of premalignant breast disease", *J. Mammary Gland Biol. Neoplasia* 5, 379-391 (2000).

Muthu et al., "Mechanisms of neuroblastoma cell growth inhibition by CARP-1 functional mimetics", *PLoS One* 9(7), e102567 (2014).

Muthu et al., "Mechanisms of neuroblastoma cell growth inhibition by CARP-1 functional mimetics", Department of Veterans Affairs Research & Development Program, John D. Dingell VA Medical Center, Detroit, MI Research Day (May 23, 2014). [Poster].

Muthu et al., "Identification and testing of novel CARP-1 functional mimetic compounds as inhibitors of non-small cell lung and triple-negative breast cancers", *J. Biomed. Nanotechnol.* 11, 1-20 (2015).

Nabha et al., "Upregulation of PKC-delta contributes to antiestrogen resistance in mammary tumor cells", *Oncogene* 24, 3166-3176 (2005).

Olomola et la., "Synthesis and antibacterial activity of two spiro [indole] thiadiazole derivatives", *Toxicological & Environmental Chemistry*, vol. 91 (5), 941-946 (2009).

Patent Cooperation Treaty, International Searching Authority, Search Report and Written Opinion for PCT/US2012/53135, 8 pages, Nov. 6, 2012.

Puliyappadamba et al., "Antagonists of Anaphase Promoting Complex (APC)-2-Cell Cycle and Apoptosis Regulatory Protein (CARP)-1 Interaction are Novel Regulators of Cell Growth and Apoptosis", *Journal of Biological Chemistry* vol. 286 (44), 38000-38017 (2011).

Puliyappadamba et al., "Development and testing of novel small molecule inhibitors of malignant pleural mesothelioma", American Association for Cancer Research New horizons in Cancer Research: Biology to Prevention to Therapy, New Delhi, India 2011. [Abstract].

Radul et al., "Synthesis, structure, and configuration of new spirooxyndol compound", *Journal of Structural Chemistry*, vol. 46 (4), 732-737 (2005).

Rishi et al., "Identification and characterization of a cell cycle and apoptosis regulatory protein-1 as a novel mediator of apoptosis signaling by retinoid CD437", *J. Biol. Chem.* 278, 33422-33435 (2003).

Rishi et al., "Cell cycle- and apoptosis-regulatory protein-1 is involved in apoptosis signaling by epidermal growth factor receptor", *J. Biol. Chem.* 281, 13188-13198 (2006).

(56) References Cited

OTHER PUBLICATIONS

Rishi et al., "CARP-1 Functional Mimetics: A Novel Class of Anti-Cancer Agents", BIT's 4th Annual World Congress of Molecular and Cell Biology, Dalian, China, Apr. 25-28, 2014. [Abstract].
Runnebaum et al., "Mutations in p53 as potential molecular markers for human breast cancer", *Proc. Natl Acad Sci* 88, 10657-10661 (1991).
Saha et al., "Syntheses of thiocarbohydrazide, some thiocarbohydrazones and their cyclized products as probes for pharmacological studies", *Indian Journal of Chemistry, Section B: Organic Chemistry Including Medicinal Chemistry*, 31B(8), 547-550 (1992), ISSN: 0376-4699; English.
Sandoval et al., "Identification and characterization of small compound inhibitors of human FATP2", *Biochemical Pharmacology*, vol. 79 (7), 99-999 (2010).
Science IP Search Report for Registry Database, 75 pages, Apr. 18, 2011.
Somagoni et al., "Nano Lipid Carrier system of a Novel Cell Cycle and Apoptosis Regulatory Protein (CARP-1) Mimetic agent to Combat Non-Small Cell Lung Cancer—In vitro and In vivo", American Association for Pharmaceutical Scientists Annual Meeting and Exposition, San Diego, CA. Nov. 2-6, 2014. [Abstract].
Somagoni et al., "Novel Cell Cycle and Apoptosis Regulatory Protein (CARP-1) Mimetic Agent Loaded Nano Lipid Formulation to Combat Triple Negative Breast Cancer", American Association for Pharmaceutical Scientists Annual Meeting and Exposition, San Diego, CA. Nov. 2-6, 2014. [Abstract].
Somogyi, "Synthesis of spiro[indoline-3,2'(3'H)-[1,3,4]thiadiazolin]-2-ones by acetylation of isatin b-thiosemicarbazones", *Liebigs Annalen der Chemie*, (8), 931-934 (1993).
Sultana et al., "Synthesis and cytotoxicity of some new 1,3,4-thiadiazoline derivatives and their Mannich bases", Journal of the Bangladesh Chemical Society 20(1), 79-85 (2007). English Abstract.
Sundararajan et al., "Caspase-dependent processing activates the proapoptotic activity of deleted in breast cancer-1 during tumor necrosis factor-alpha-mediated death signaling", *Oncogen* 24, 4908-4920 (2005).
Tomchin, "Heterocyclic semicarbazones and thiosemicarbazones. L. Reaction of 1-acylisatins with (arenethioyl)hydrazines", HCAPLUS, Accession No. 1988:131684, Zhurnal Organicheskoi Khimii (1987), 23(6), 1305-12.
Tomchin et al., "Heterocyclic semicarbazones and thiosemicarbazones. XLVI. Activity of acylhydrazones of a-dicarbonyl compounds with respect to influenza virus", HCAPLUS, Accession No. 1984:85533, Khimiko-Farmatsevticheskii Zhurnal (1983), 17(6), 691-7.
Tomchin, "Structure of condensation products of 1-alkylisatins with thiobenzoylhydrazine", HCAPLUS, Accession No. 1981:569091, Zhurnal Organicheskoi Khimii (1981), 17(7), 1561-2.
Tomchin, "Heterocyclic semicarbazones and thiosemicarbazones. XLIV. Cyclization of isatin and 1-acetylisatin 3-thiobenzoylhydrazones", HCAPLUS, Accession No. 1981:462139, Zhurnal Organicheskoi Khimii (1981), 17(3), 589-95.
Tomchin et al., "Heterocyclic semicarbazones and thiosemicarbazones. XXXV. Transformations of 5'-phenylthiocarbohydrazones of isatin and acenaphthenequinone", HCAPLUS, Accession No. 1975:140027, Zhurnal Organicheskoi Khimii (1975), 11(1), 184-90.
Ude et al., "Mechanisms of Cancer Cell Growth Inhibition by Novel Small Molecule Compounds", Summer Undergraduate Research Experience, Cancer Biology Program, Karmanos Cancer Institute, Wayne State University; Aug. 2014. [Poster].
Vineshkumar et al., "Development and testing of novel small molecule inhibitors of malignant pleural mesothelioma", Department of Veterans Affairs Research & Development Program, John D. Dingell VA Medical Center, Detroit, MI Research Day (Apr. 27, 2012). [Poster].
Wadia et al., "Transducible TAT-HA fusogenic peptide enhances escape of TAT-fusion proteins after lipid raft micropinocytosis", *Nat. Medicine* 10, 310-315 (2004).
Wang et al., "Targeted proteasome inhibition by Velcade induces apoptosis in human mesothelioma and breast cancer cell lines", *Can. Chemother. Pharmacol.* 66, 455-466 (2010).
Yu et al., "Identification of a cullin homology region in a subunit of the anaphase-promoting complex", *Science* 279, 1219-1222 (1998).
Zhang et al., "Transactivator of transcription-tagged cell cycle and apoptosis regulatory protein-1 peptides suppress the growth of human breast cancer cells in vitro and in vivo", *Mol. Cancer Ther.* 6(5), 1661-1672 (2007).

* cited by examiner

FIGURE 1 (PULIYAPPADAMBA ET AL)

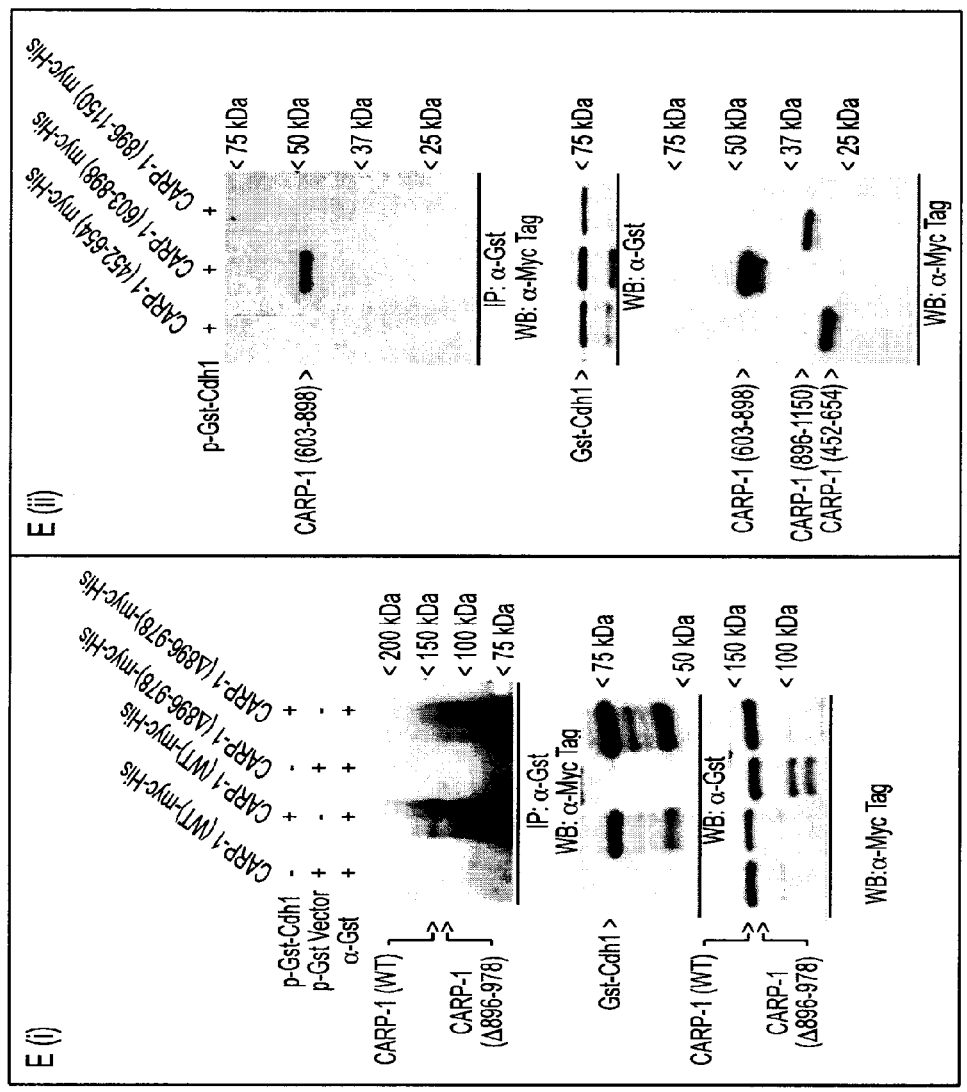
FIG. 1E(i) AND 1E(ii)

A

B

FIGURE 7 (PULIYAPPADAMBA ET AL)

FIG. 14

| Compound number | Rel. cell viability MDA-MB-468 (20μM) | IC50(μM) | | | | | | | | | | | |
|---|---|---|---|---|---|---|---|---|---|---|---|---|---|
| | | Cervical Cancer HeLa Cells | HUMAN BREAST CANCER CELLS | | | | | HUMAN PANCREATIC CANCER CELLS | | HUMAN PROSTATE CANCER CELLS | | HUMAN MESOTHELIOMA CELLS | |
| | | | MCF-7 | MDA-MB-231 | MDA-MB-468 | MDA-MB-453 | SKBR-3 | BxPc-3 | PANC-1 | PC-3 | LnCaP | H2461 | H2373 |
| CFM-4 | 0.48 | 10-15 | >20 | 10 | 10-15 | 10 | 10 | >20 | 20 | 10 | 20 | 20 | 20 |
| 1 | 0.15 | 0.5 | ~15 | 0.5 | 1.0 | 0.5 | 0.4 | 2.0 | 0.5 | 15 | 20 | 15 | 0.2 |
| 2 | 0.08 | 0.5 | ~15 | 0.2 | 0.2 | 0.5 | 0.2 | 2.0 | 3.0 | 15 | 20 | 15 | 10 |
| 4 | 0.61 | ND | ND | | | | | | | | | | |

| Compound number | Rel. cell viability MDA-MB-468 (20μM) | IC50(μM) | | | | | | | | | | | |
|---|---|---|---|---|---|---|---|---|---|---|---|---|---|
| | | Cervical Cancer HeLa Cells | HUMAN BREAST CANCER CELLS | | | | | HUMAN PANCREATIC CANCER CELLS | | HUMAN PROSTATE CANCER CELLS | | HUMAN MESOTHELIOMA CELLS | |
| | | | MCF-7 | MDA-MB-231 | MDA-MB-468 | MDA-MB-453 | SKBR-3 | BxPc-3 | PANC-1 | PC-3 | LnCaP | H2461 | H2373 |
| CFM-4 | 0.48 | 10-15 | >20 | 10 | 10-15 | 10 | 10 | >20 | 20 | 10 | 20 | 20 | 20 |
| 12 | 0.10 | 10 | 15 | 7 | 10 | 10 | 7 | 20 | 10 | 15 | 20 | 15 | 10 |
| 5 | 0.32 | ND | | | | | | | | | | | |
| 13 | 0.68 | ND | | | | | | | | | | | |
| 10 | 0.30 | ND | | | | | | | | | | | |
| 7 | 0.19 | 15 | 20 | 10 | 10 | 10 | 7 | 20 | 15 | 15 | >20 | 15 | 10 |
| 8 | 0.61 | ND | | | | | | | | | | | |
| 11 | 0.40 | ND | | | | | | | | | | | |

THERAPEUTIC COMPOUNDS AND METHODS

CROSS REFERENCE TO RELATED APPLICATION

This patent application claims the benefit of priority of U.S. application Ser. No. 61/529,144, filed Aug. 30, 2011, which application is hereby incorporated by reference.

GOVERNMENT FUNDING

The invention described herein was made with government support from the Department of Veterans Affairs. The United States Government has certain rights in the invention.

BACKGROUND OF THE INVENTION

A range of intracellular as well as extracellular signals are known to target the cell division cycle and apoptosis pathways and function to maintain homeostasis in normal tissues. The pathways regulating the cell division cycle as well as apoptosis are frequently altered in inflammation-associated disorders such as cancers. The regulators of mitotic control and/or apoptosis signaling therefore remain important targets for current and future intervention strategies for such disorders.

The identification and characterization of a peri-nuclear protein termed CARP-1/CCAR1 that functions to regulate chemotherapy-dependent apoptosis signaling has been reported. Depletion of CARP-1 confers resistance to apoptosis induced by chemotherapeutic agents such as adriamycin or Iressa. CARP-1 functions in a biphasic manner as a co-activator of signaling by steroid receptors and tumor suppressor p53. CARP-1 expression enhances CDKI p21$^{WAF1CIP1}$ levels and apoptosis while attenuating expression of mediators of cell-cycle and/or proliferation such as c-Myc, cyclin B, topoisomerase IIα, p21Rac1, and mitogen-activated protein kinase (MAPK)/extracellular signal regulating kinase (ERK) 1/2 regulator MEK2. CARP-1 is a serine and tyrosine phospho-protein that possesses multiple, non-overlapping apoptosis-inducing subdomains. CARP-1 tyrosine$^{192}$ regulates apoptosis signaling by EGFRs, while CARP-1-dependent apoptosis involves activation of stress-activated protein kinase (SAPK) p38α/β, and caspase-9.

The APC/C is a multiprotein complex with E3 ubiquitin ligase activity. APC/C is inhibited by activation of the mitotic spindle checkpoint during the cell division cycle. APC/C-targeting/activating molecules such as securin, polo-like kinase, aurora kinase, and SnoN are potential oncogenes that often promote dysregulation of APC/C. APC/C is composed of at least 12 subunits, which contains tetratricopeptide repeat proteins (APC-3, 5, 6, 7, and 8), a cullin homology protein (APC-2), and a ring-H2 finger domain protein (APC-11). APC/C requires two WD40 repeat-containing coactivators, Cdc20 and Cdh1, to recruit and select various substrates at different stages of the cell cycle. APC/C$^{Cdc20}$ promotes metaphase/anaphase transition by ubiquitinating and degrading securin, an inhibitor of separase that participates in degradation of the chromatin cohesion complex. APC/C$^{Cdc20}$ also ubiquitinates cyclin-B1 and accelerates its loss during late mitosis to promote exit from M phase. In addition, APC/C targets various cell cycle regulatory molecules, including spindle-associated proteins, DNA replication inhibitors, and mitotic kinases. Alterations in APC/C complex proteins have been noted in breast and colon cancer cells as well as primary colon cancers, while endogenous as well as synthetic inhibitors targeting APC/C-activating oncogenes or the APC/C complex have also been recently described. A yeast-two-hybrid (Y2H) screen has revealed CARP-1 interaction with the APC-2 protein. Antagonists of CARP-1 binding with APC-2 were identified (e.g. CFMs, CARP-1 Functional Mimetics).

Accordingly, there is a need for additional agents that treat cancer including agents that treat cancer via novel mechanisms of action. There is also a need for agents that treat breast cancer including drug resistant breast cancers.

SUMMARY OF THE INVENTION

In one embodiment the invention provides a compound of formula I:

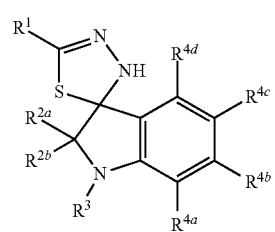

I wherein:

$R^1$ is aryl or —$(C_1$-$C_6)$alkylaryl, wherein any aryl or —$(C_1$-$C_6)$alkylaryl of $R^1$ is optionally substituted with one or more groups (e.g. 1, 2, 3, 4 or 5) selected from $(C_1$-$C_6)$alkyl, $(C_2$-$C_6)$alkenyl, $(C_2$-$C_6)$alkynyl, $(C_3$-$C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$;

$R^{2a}$ and $R^{2b}$ are each H, or $R^{2a}$ and $R^{2b}$ together are oxo(=O);

$R^3$ is —$(C_1$-$C_6)$alkylaryl or —$(C_1$-$C_6)$alkylheteroaryl, wherein any —$(C_1$-$C_6)$alkylaryl or —$(C_1$-$C_6)$alkylheteroaryl of $R^3$ is optionally substituted with one or more groups (e.g. 1, 2, 3, 4 or 5) selected from $Z^1$, $(C_1$-$C_6)$alkyl, $(C_2$-$C_6)$alkenyl and $(C_2$-$C_6)$alkynyl;

$R^{4a}$ is H, $(C_1$-$C_8)$alkyl, $(C_2$-$C_6)$alkenyl, $(C_2$-$C_6)$alkynyl, $(C_3$-$C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4b}$ is H, $(C_1$-$C_8)$alkyl, $(C_2$-$C_8)$alkenyl, $(C_2$-$C_8)$alkynyl, $(C_3$-$C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4c}$ is H, $(C_1$-$C_8)$alkyl, $(C_2$-$C_8)$alkenyl, $(C_2$-$C_8)$alkynyl, $(C_3$-$C_7)$carbocycle, halogen, —CN, —$OR_{n3}$, —$NR_{q3}R_{r3}$, —$NR_{n3}R_{p3}$, $NO_2$, —$C(O)R_{n3}$ or —$C(O)OR_{n3}$;

$R^{4d}$ is H, $(C_1$-$C_8)$alkyl, $(C_2$-$C_8)$alkenyl, $(C_2$-$C_8)$alkynyl, $(C_3$-$C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

each $Z^1$ is independently selected from $(C_3$-$C_7)$carbocycle, halogen, —CN, —$OR_{n2}$, —$NR_{q2}R_{r2}$, —$NR_{n2}COR_{p2}$, $NO_2$, —$C(O)R_{n2}$ and —$C(O)OR_{n2}$;

each $R_{n1}$ is independently selected from H, $(C_1$-$C_6)$alkyl, $(C_2$-$C_6)$alkenyl, $(C_2$-$C_6)$alkynyl and $(C_3$-$C_7)$carbocycle;

each $R_{p1}$ is independently selected from $(C_1$-$C_6)$alkyl, $(C_2$-$C_6)$alkenyl, $(C_2$-$C_6)$alkynyl and $(C_3$-$C_7)$carbocycle;

$R_{q1}$ and $R_{r1}$ are each independently selected from H, $(C_1$-$C_6)$alkyl, $(C_2$-$C_6)$alkenyl, $(C_2$-$C_6)$alkynyl and $(C_3$-$C_7)$carbocycle, or $R_{q1}$ and $R_{r1}$ together with the nitrogen to which they are attached form a heterocycle;

each $R_{n2}$ is independently selected from H, $(C_1-C_6)$alkyl, $(C_2-C_6)$alkenyl, $(C_2-C_6)$alkynyl and $(C_3-C_7)$carbocycle;

each $R_{p2}$ is independently selected from $(C_1-C_6)$alkyl, $(C_2-C_6)$alkenyl, $(C_2-C_6)$alkynyl and $(C_3-C_7)$carbocycle;

$R_{q2}$ and $R_{r2}$ are each independently selected from H, $(C_1-C_6)$alkyl, $(C_2-C_6)$alkenyl, $(C_2-C_6)$alkynyl and $(C_3-C_7)$carbocycle, or $R_{q2}$ and $R_{r2}$ together with the nitrogen to which they are attached form a heterocycle;

each $R_{n3}$ is independently selected from H, $(C_1-C_6)$alkyl, $(C_2-C_6)$alkenyl, $(C_2-C_6)$alkynyl and $(C_3-C_7)$carbocycle;

each $R_{p3}$ is independently selected from $(C_1-C_6)$alkyl, $(C_2-C_6)$alkenyl, $(C_2-C_6)$alkynyl and $(C_3-C_7)$carbocycle; and $R_{q3}$ and $R_{r3}$ are each independently selected from H, $(C_1-C_6)$alkyl, $(C_2-C_6)$alkenyl, $(C_2-C_6)$alkynyl and $(C_3-C_7)$carbocycle, or $R_{q3}$ and $R_{r3}$ together with the nitrogen to which they are attached form a heterocycle;

or a pharmaceutically acceptable salt thereof;

provided:

$R^1$ is not 4-methylphenyl when, $R^{4a}$ is H, $R^{4b}$ is H, $R^{4c}$ is methyl, $R^{4d}$ is H, $R^3$ is benzyl and $R^{2a}$ and $R^{2b}$ together are oxo(=O);

$R^1$ is not 4-methoxyphenyl when, $R^{4a}$ is H, $R^{4b}$ is H or n-propyl, $R^{4c}$ is H or methyl, $R^{4d}$ is H, $R^3$ is benzyl and $R^{2a}$ and $R^{2b}$ together are oxo(=O);

$R^3$ is not 2-chlorophenylmethyl, 2-fluorophenylmethyl, 2,6-dichlorophenylmethyl, 4-chlorophenylmethyl, 4-fluorophenylmethyl or naphth-1-ylmethyl when $R^1$ is phenyl, $R^{4a}$ is H, $R^{4b}$ is H, $R^{4c}$ is H, $R^{4d}$ is H and $R^{2a}$ and $R^{2b}$ together are oxo(=O); and $R^3$ is not 4-nitrophenylmethyl when $R^1$ is 4-methylphenyl, $R^{4a}$ is H, $R^{4b}$ is H, $R^{4c}$ is H, $R^{4d}$ is H and $R^{2a}$ and $R^{2b}$ together are oxo(=O); and $R^3$ is not 2-phenylethyl when $R^1$ is phenyl, $R^{4a}$ is H, $R^{4b}$ is H, $R^{4c}$ is Br, $R^{4d}$ is H and $R^{2a}$ and $R^{2b}$ together are oxo(=O).

In one embodiment, the invention provides a method for treating cancer (e.g. breast cancer, pancreatic cancer and mesotheliomas) in a mammal (e.g. a human) comprising administering to the mammal an effective amount of a compound of formula I:

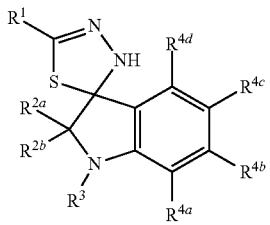

I wherein:

$R^1$ is aryl or $—(C_1-C_6)$alkylaryl, wherein any aryl or $—(C_1-C_6)$alkylaryl of $R^1$ is optionally substituted with one or more groups (e.g. 1, 2, 3, 4 or 5) selected from $(C_1-C_6)$alkyl, $(C_2-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$;

$R^{2a}$ and $R^{2b}$ are each H, or $R^{2a}$ and $R^{2b}$ together are oxo(=O);

$R^3$ is H, $(C_1-C_6)$alkyl, —$(C_1-C_6)$alkylaryl or —$(C_1-C_6)$alkylheteroaryl, wherein any $(C_1-C_6)$alkyl of $R^3$ is optionally substituted with one or more (e.g. 1, 2, 3, 4 or 5) $Z^1$ groups and wherein any —$(C_1-C_6)$alkylaryl or —$(C_1-C_6)$alkylheteroaryl of $R^3$ is optionally substituted with one or more (e.g. 1, 2, 3, 4 or 5) groups selected from $Z^1$, $(C_1-C_6)$alkyl, $(C_2-C_6)$alkenyl and $(C_2-C_6)$alkynyl;

$R^{4a}$ is H, $(C_1-C_8)$alkyl, $(C_2-C_6)$alkenyl, $(C_2-C_6)$alkynyl, $(C_3-C_7)$carbocycle, halogen, —CN, —$OR_{n3}$, —$NR_{q3}R_{r3}$, —$NR_{n3}R_{p3}$, $NO_2$, —$C(O)R_{n3}$ or —$C(O)OR_{n3}$;

$R^{4b}$ is H, $(C_1-C_8)$alkyl, $(C_2-C_8)$alkenyl, $(C_2-C_8)$alkynyl, $(C_3-C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4c}$ is H, $(C_1-C_8)$alkyl, $(C_2-C_8)$alkenyl, $(C_2-C_8)$alkynyl, $(C_3-C_7)$carbocycle, halogen, —CN, —$OR_{13}$, —$NR_{q3}R_{r3}$, —$NR_{n3}COR_{p3}$, $NO_2$, —$C(O)R_{n3}$ or —$C(O)OR_{n3}$;

$R^{4d}$ is H, $(C_1-C_8)$alkyl, $(C_2-C_8)$alkenyl, $(C_2-C_8)$alkynyl, $(C_3-C_7)$carbocycle, halogen, —CN, —$OR_{n3}$, —$NR_{q3}R_{r3}$, —$NR_{n3}R_{p3}$, $NO_2$, —$C(O)R_{n3}$ or —$C(O)OR_{n3}$;

each $Z^1$ is independently selected from $(C_3-C_7)$carbocycle, halogen, —CN, —$OR_{n2}$, —$NR_{q2}R_{r2}$, —$NR_{n2}COR_{p2}$, $NO_2$, —$C(O)R_{n2}$ and —$C(O)OR_{n2}$;

each $R_{n1}$ is independently selected from H, $(C_1-C_6)$alkyl, $(C_2-C_6)$alkenyl, $(C_2-C_6)$alkynyl and $(C_3-C_7)$carbocycle;

each $R_{p1}$ is independently selected from $(C_1-C_6)$alkyl, $(C_2-C_6)$alkenyl, $(C_2-C_6)$alkynyl and $(C_3-C_7)$carbocycle;

$R_{q1}$ and $R_{r1}$ are each independently selected from H, $(C_1-C_6)$alkyl, $(C_2-C_6)$alkenyl, $(C_2-C_6)$alkynyl and $(C_3-C_7)$carbocycle, or $R_{q1}$ and $R_{r1}$ together with the nitrogen to which they are attached form a heterocycle;

each $R_{n2}$ is independently selected from H, $(C_1-C_6)$alkyl, $(C_2-C_6)$alkenyl, $(C_2-C_6)$alkynyl and $(C_3-C_7)$carbocycle;

each $R_{p2}$ is independently selected from $(C_1-C_6)$alkyl, $(C_2-C_6)$alkenyl, $(C_2-C_6)$alkynyl and $(C_3-C_7)$carbocycle;

$R_{q2}$ and $R_{r2}$ are each independently selected from H, $(C_1-C_6)$alkyl, $(C_2-C_6)$alkenyl, $(C_2-C_6)$alkynyl and $(C_3-C_7)$carbocycle, or $R_{q2}$ and $R_{r2}$ together with the nitrogen to which they are attached form a heterocycle;

each $R_{n3}$ is independently selected from H, $(C_1-C_6)$alkyl, $(C_2-C_6)$alkenyl, $(C_2-C_6)$alkynyl and $(C_3-C_7)$carbocycle;

each $R_{p3}$ is independently selected from $(C_1-C_6)$alkyl, $(C_2-C_6)$alkenyl, $(C_2-C_6)$alkynyl and $(C_3-C_7)$carbocycle; and $R_{q3}$ and $R_{r3}$ are each independently selected from H, $(C_1-C_6)$alkyl, $(C_2-C_6)$alkenyl, $(C_2-C_6)$alkynyl and $(C_3-C_7)$carbocycle, or $R_{q3}$ and $R_{r3}$ together with the nitrogen to which they are attached form a heterocycle;

or a pharmaceutically acceptable salt thereof.

The invention also provides a pharmaceutical composition comprising a compound of formula I or a pharmaceutically acceptable salt thereof, and a pharmaceutically acceptable carrier.

The invention also provides a method for treating cancer (e.g. breast cancer including a drug resistant breast cancer, pancreatic cancer and mesotheliomas) in a mammal comprising administering to the mammal an effective amount of a compound of formula I, or a pharmaceutically acceptable salt thereof.

The invention also provides a pharmaceutical composition for the treatment of cancer (e.g. breast cancer including a drug resistant breast cancer, pancreatic cancer and mesotheliomas), comprising a compound of formula I, or a pharmaceutically acceptable salt thereof, in combination with a pharmaceutically acceptable carrier.

The invention also provides a compound of formula I, or a pharmaceutically acceptable salt thereof, or composition of formula I, for use in the prophylactic or therapeutic treatment of cancer (e.g. breast cancer including a drug resistant breast cancer, pancreatic cancer and mesotheliomas).

The invention also provides a compound of formula I, or a pharmaceutically acceptable salt thereof, or composition of formula I, for use in the manufacture of a medicament for the treatment cancer (e.g. breast cancer including a drug resistant breast cancer, pancreatic cancer and mesotheliomas) in a mammal (e.g. a human).

The invention also provides novel compounds of formula I as well as processes and novel intermediates that are useful for preparing novel compounds of formula I or salts thereof.

BRIEF DESCRIPTION OF THE FIGURES

FIGS. 1A-1E(ii): CARP-1 interacts with APC-2. 1A, protein complexes from approximately 1 mg total proteins derived from wild-type HBC or HeLa cells were subjected to IP using anti-Gst, anti-CARP-1 ($\alpha$2), or anti-APC-2 antibodies. Immunoprecipitates or 50 µg of the respective cell lysate/lane were analyzed by WB with noted antibodies. 1B, schematic of CARP-1 and its mutants (left hand box) and APC-2 and its mutants (right hand box) that interact with APC-2 and CARP-1 proteins, respectively. Numbers above or at the side of each bar indicate amino acids of the respective proteins. +, positive interaction; −, no interaction. CS, Cold shock domain; SAP, DNA binding domain; CH, Cullin homology domain; $\alpha$1 and $\alpha$2, epitopes for CARP-1 $\alpha$1 and $\alpha$2 polyclonal antibodies, respectively. 1C, cos-7 cells were transfected with plasmid encoding Gst-tagged APC-2 alone or in combination with vector plasmid pcDNA3, plasmid for myc-His-tagged CARP-1 (WT) or plasmid for myc-His-tagged CARP-1 ($\Delta$896-978) protein as indicated. Protein complexes were subjected to IP using anti-STAT3 or anti-myc-tag antibodies. Immunoprecipitates or protein lysates were subjected to WB with anti-Gst antibodies as in A. The membrane with immunoprecipitates was then probed with anti-Myc tag antibodies (lower blot). 1D, CARP-1 interacts with Cdc20 and Cdh1. Protein complexes derived from wild-type MDA-MB-468 HBC cells (upper blot) or cos-7 cells transfected with noted plasmids (lower blot) were subjected to IP using indicated antibodies, followed by WB of the Immunoprecipitates or respective cell lysate as in A. 1E, Cdh1-interacting epitope of CARP-1 is distinct from its APC-2-binding epitope. Cos-7 cells were transfected with plasmids encoding myc-His-tagged wild-type (WT) CARP-1, its $\Delta$896-978 mutant in (i), or different CARP-1 mutants (ii) in combination with plasmid expressing Gst-Cdh1. The cell lysates were subjected to IP-WB using indicated antibodies as in A. Presence of the endogenous or the transfected proteins in panels A, C, D, and E is indicated by a arrowhead on the left side of each blot except that the Gst-tagged Cdc20 and Cdh1 are indicated in the respective lane of the lower blot of panel D. Approximate location of various molecular weight markers is indicated on the right side of each blot in panels A, C, D, and E. kDa, kilodalton.

FIG. 14: Testing of compounds of formula I in various cancer cells.

DETAILED DESCRIPTION OF THE INVENTION

Definitions

Figure 1A:
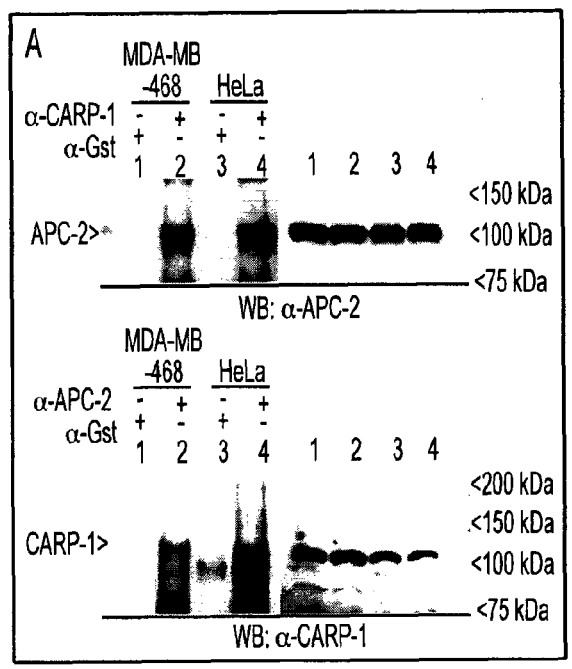

"Alkyl" denotes both straight and branched carbon chains but reference to an individual radical such as "propyl" embraces only the straight chain radical, a branched chain isomer such as "isopropyl" being specifically referred to. For example, an alkyl group can have 1 to 20 carbon atoms (i.e., ($C_1$-$C_{20}$)alkyl), 2 to 8 carbon atoms (i.e., ($C_1$-$C_8$)alkyl), or 1 to 6 carbon atoms (i.e., ($C_1$-$C_6$)alkyl).

"Alkenyl" is a straight or branched hydrocarbon containing at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon containing at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

"Alkylaryl" refers to an alkyl radical as defined herein in which one of the hydrogen atoms bonded to a carbon atom is replaced with an aryl radical as described herein (i.e., an -alkyl-aryl moiety). For example, the alkyl group of the "alkylaryl" can be 1 to 6 carbon atoms (i.e. —($C_1$-$C_6$) alkylaryl). Alkylaryl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1, 2, 3, 4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. The rings of the multiple condensed ring system can be connected to each other via fused, Spiro and bridged bonds when allowed by valency requirements. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Alkylheteroaryl" refers to an alkyl radical as defined herein in which one of the hydrogen atoms bonded to a carbon atom is replaced with a heteroaryl radical as described herein (i.e., an -alkyl-heteroaryl moiety). For example, the alkyl group of the "alkylheteroaryl" can be 1 to 6 carbon atoms (i.e. —($C_1$-$C_6$)alkylheteroaryl). Alkylheteroaryl groups include, but are not limited to, pyridylmethyl, 2-pyrdin-2-ylethan-1-yl and the like.

The term "heterocyclyl" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, Spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a Spiro connection (e.g. spiropentane, spiro[4,5]decane, spiro[4.5]decane, etc), via two adjacent carbon atoms to form a fused connection such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity).

"Treatment" or "treating" refers to any manner in which the symptoms of a condition, disorder or disease are ameliorated or otherwise beneficially altered. In the context of treating the cancers disclosed herein, the cancer can be onset, relapsed or refractory. Full eradication of the condition, disorder or disease is not required. Amelioration of symptoms of a particular disorder refers to any lessening of symptoms, whether permanent or temporary, that can be attributed to or associated with administration of a therapeutic composition of the present invention or the corresponding methods and combination therapies. Treatment also encompasses pharmaceutical use of the compositions in accordance with the methods disclosed herein.

"Mammal" as used herein includes humans.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the method of the invention may have chiral centers, e.g., chiral carbon or phosphorus atoms. The compounds thus include racemic mixtures of all stereoisomers, including enantiomers, diastereomers, and atropisomers. In addition, the compounds include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the method of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

It is understood by one skilled in the art that this invention also includes any compound that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

Compounds of Formula I

A specific group of compounds of formula I are compounds of formula Ia.

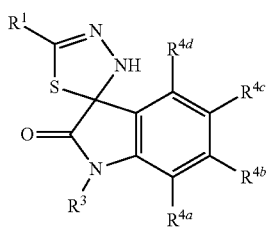

and pharmaceutically acceptable salts thereof.

Specific values listed below are values for compounds of formula I as well as the compounds of formula Ia.

A specific group of compounds of formula I are compounds wherein $R^{2a}$ and $R^{2b}$ together are oxo(=O).

A specific value for $R^3$ is —$(C_1-C_6)$alkylaryl, wherein —$(C_1-C_6)$alkylaryl is optionally substituted with one or more groups selected from $Z^1$, $(C_1-C_6)$alkyl, $(C_2-C_6)$alkenyl and $(C_2-C_6)$alkynyl.

Another specific value for $R^3$ is benzyl, wherein benzyl is optionally substituted with one or more groups selected from $Z^1$, $(C_1-C_6)$alkyl, $(C_2-C_6)$alkenyl and $(C_2-C_6)$alkynyl.

Another specific value for $R^3$ is benzyl, naphth-2-ylmethyl, 2-chlorobenzyl, 2-methoxybenzyl, 3-chlorobenzyl, pyridine-2-ylmethyl or quinolin-8-ylmethyl.

Another specific value for $R^3$ is:

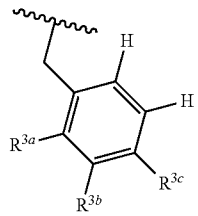

wherein $R^{3a}$, $R^{3b}$ and $R^{3c}$ are each independently selected from H, $Z^1$, $(C_1-C_6)$alkyl, $(C_2-C_6)$alkenyl and $(C_2-C_6)$alkynyl.

A specific group of compounds of formula I are compounds wherein $R^{3b}$ and $R^{3c}$ are each H.

A specific group of compounds of formula I are compounds wherein $R^{3a}$ and $R^{3b}$ are each H.

A specific value for $R^{3b}$ is H.

A specific group of compounds of formula I are compounds wherein each $Z^1$ is selected from $(C_3-C_7)$carbocycle, Br, I, —CN, —$OR_{n2}$, —$O(C_3-C_7)$carbocycle, —$NR_{q2}R_{r2}$, —$NR_{n2}COR_{p2}$, $NO_2$, —$C(O)R_{n2}$ and —$C(O)OR_{n2}$.

Another specific group of compounds of formula I are compounds wherein each $Z^1$ is selected from $(C_3-C_7)$carbocycle, —CN, —$OR_{n2}$, —$O(C_3-C_7)$carbocycle, —$NR_{q2}R_{r2}$, —$NR_{n2}COR_{p2}$, $NO_2$, —$C(O)R_{n2}$ and —$C(O)OR_{n2}$.

Another specific group of compounds of formula I are compounds wherein each $Z^1$ is independently selected from $(C_3-C_7)$carbocycle, Br, I, —CN, —OH, —$O(C_2-C_6)$alkyl, —$O(C_2-C_6)$alkenyl, —$O(C_2-C_6)$alkynyl, —$O(C_3-C_7)$carbocycle, —$NR_{q2}R_{r2}$, —$NR_{n2}COR_{p2}$, $NO_2$, —$C(O)R_{n2}$ and —$C(O)OR_{n2}$.

Another specific group of compounds of formula I are compounds wherein each $Z^1$ is independently selected from $(C_3-C_7)$carbocycle, —CN, —OH, —$O(C_3-C_6)$alkyl, —$O(C_2-C_6)$alkenyl, —$O(C_2-C_6)$alkynyl, —$O(C_3-C_7)$carbocycle, —$NR_{q2}R_{r2}$, —$NR_{n2}COR_{p2}$, $NO_2$, —$C(O)R_{n2}$ and —$C(O)OR_{n2}$.

Another specific group of compounds of formula I are compounds wherein each $Z^1$ is independently selected from $(C_3-C_7)$carbocycle, Br, I, —CN, —$OR_{n2}$, —$O(C_3-C_7)$carbocycle, —$NR_{q2}R_{p2}$, —$NR_{n2}COR_{p2}$, —$C(O)R_{n2}$ and —$C(O)OR_{n2}$.

Another specific group of compounds of formula I are compounds wherein each $Z^1$ is independently selected from $(C_3-C_7)$carbocycle, —CN, —$OR_{n2}$, —$O(C_3-C_7)$carbocycle, —$NR_{q2}R_{r2}$, —$NR_{n2}COR_{p2}$, —$C(O)R_{n2}$ and —$C(O)OR_{n2}$.

Another specific group of compounds of formula I are compounds wherein each $Z^1$ is independently selected from $(C_3-C_7)$carbocycle, Br, I, —CN, —OH, —$O(C_2-C_6)$alkyl, —$O(C_2-C_6)$alkenyl, —$O(C_2-C_6)$alkynyl, —$O(C_3-C_7)$carbocycle, —$NR_{q2}R_{r2}$, —$NR_{n2}COR_{p2}$, —$C(O)R_{n2}$ and —$C(O)OR_{n2}$.

Another specific group of compounds of formula I are compounds wherein each $Z^1$ is independently selected from $(C_3-C_7)$carbocycle, —CN, —OH, —$O(C_3-C_6)$alkyl, —$O(C_2-C_6)$alkenyl, —$O(C_2-C_6)$alkynyl, —$O(C_3-C_7)$carbocycle, —$NR_{q2}R_{r2}$, —$NR_{n2}COR_{p2}$, —$C(O)R_{n2}$ and —$C(O)OR_{n2}$.

A specific value for $R^3$ is —$(C_1-C_6)$alkylheteroaryl, wherein any —$(C_1-C_6)$alkylheteroaryl of $R^3$ is optionally substituted with one or more groups selected from $Z^1$, $(C_1-C_6)$alkyl, $(C_2-C_6)$alkenyl and $(C_2-C_6)$alkynyl.

A specific value for $R^{4a}$ is H.
A specific value for $R^{4b}$ is H.
A specific value for $R^{4d}$ is H.
A specific value for $R^{4c}$ is H, halogen, or —$OR_{n3}$.
A specific value for $R_{n3}$ is independently $(C_1-C_6)$alkyl.
A specific value for $R^{4c}$ is H.
A specific value for $R^1$ is aryl, wherein any aryl of $R^1$ is optionally substituted with one or more groups selected from $(C_1-C_6)$alkyl, $(C_2-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$.

Another specific value for $R^1$ is:

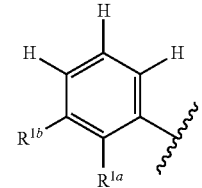

wherein each $R^{1a}$ and $R^{1b}$ is independently selected from H, $(C_1-C_6)$alkyl, $(C_2-C_6)$alkenyl, $(C_2-C_6)$alkynyl, $(C_3-C_7)$ carbocycle, halogen, —CN, —OR$_{n1}$, —NR$_{q1}$R$_{r1}$, —NR$_{n1}$COR$_{p1}$, NO$_2$, —C(O)R$_{n1}$ and —C(O)OR$_{n1}$.

A specific value for R$^{1a}$ is H.

A specific value for R$^{1b}$ is H.

A specific group of compounds of formula I are compounds wherein at least one of R$^{1a}$ or R$^{1b}$ is independently selected (C$_1$-C$_6$)alkyl, (C$_2$-C$_6$)alkenyl, (C$_2$-C$_6$)alkynyl, (C$_3$-C$_7$)carbocycle, halogen, —CN, —OR$_{n1}$, —NR$_{q1}$R$_{r1}$, —NR$_{n1}$COR$_{p1}$, NO$_2$, —C(O)R$_{n1}$ and —C(O)OR$_{n1}$.

Another specific value for R$^1$ is phenyl or —(C$_1$-C$_6$)alkylphenyl, wherein any phenyl or —(C$_1$-C$_6$)alkylphenyl of R$^1$ is optionally substituted with one or more groups selected from (C$_1$-C$_6$)alkyl, (C$_2$-C$_6$)alkenyl, (C$_2$-C$_6$)alkynyl, (C$_3$-C$_7$)carbocycle, halogen, —CN, —OR$_{n1}$, —NR$_{q1}$R$_{r1}$, —NR$_{n1}$COR$_{p1}$, NO$_2$, —C(O)R$_{n1}$ and —C(O)OR$_{n1}$.

Another specific value for R$^1$ is phenyl, wherein phenyl is optionally substituted with one or more groups selected from (C$_1$-C$_6$)alkyl, (C$_2$-C$_6$)alkenyl, (C$_2$-C$_6$)alkynyl, (C$_3$-C$_7$)carbocycle, halogen, —CN, —OR$_{n1}$, —NR$_{q1}$R$_{r1}$, —NR$_{n1}$COR$_{p1}$, NO$_2$, —C(O)R$_{n1}$ and —C(O)OR$_{n1}$.

Another specific value for R$^1$ is phenyl, wherein phenyl is optionally substituted with one or more groups selected from (C$_1$-C$_6$)alkyl, halogen or —OR$_n$.

Another specific value for R$^1$ is phenyl, 3-chlorophenyl, 3-methoxyphenyl or 2-methylphenyl.

Another specific value for R$^3$ is (C$_1$-C$_6$)alkyl or —(C$_1$-C$_6$)alkylaryl, wherein any (C$_1$-C$_6$)alkyl of R$^3$ is optionally substituted with one or more Z$^1$ groups and wherein any —(C$_1$-C$_6$)alkylaryl is optionally substituted with one or more groups selected from Z$^1$, (C$_1$-C$_6$)alkyl, (C$_2$-C$_6$)alkenyl and (C$_2$-C$_6$)alkynyl.

Another specific value for R$^3$ is —(C$_1$-C$_6$)alkylaryl, wherein —(C$_1$-C$_6$)alkylaryl is optionally substituted with one or more groups selected from Z$^1$, (C$_1$-C$_6$)alkyl, (C$_2$-C$_6$)alkenyl and (C$_2$-C$_6$)alkynyl.

Another specific value for R$^3$ is —(C$_1$-C$_6$)alkylaryl, wherein —(C$_1$-C$_6$)alkylaryl is optionally substituted with one or more halogen.

Another specific value for R$^3$ is methyl, benzyl, phenethyl or —(CH$_2$)-naphthyl wherein benzyl is substituted with one or more halogen.

One specific group of compounds of formula I are compounds wherein each R$^{4a}$, R$^{4b}$, R$^{4c}$ and R$^{4d}$ is independently H or halogen.

In one embodiment the compounds of formula I are selected from:

-continued
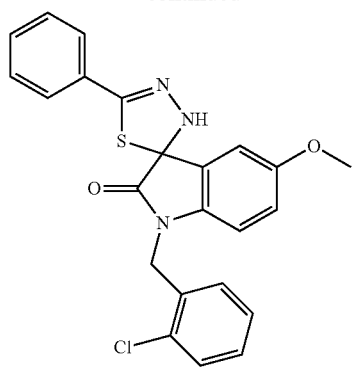
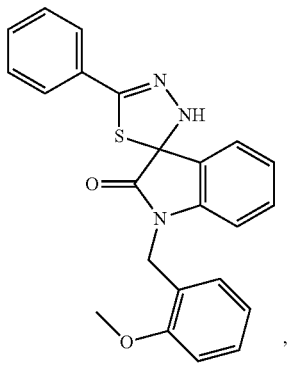
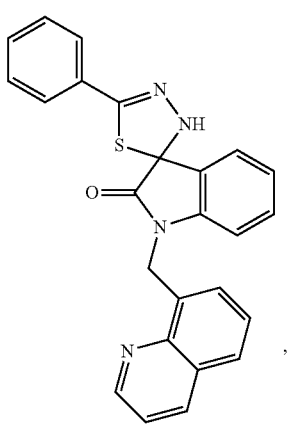
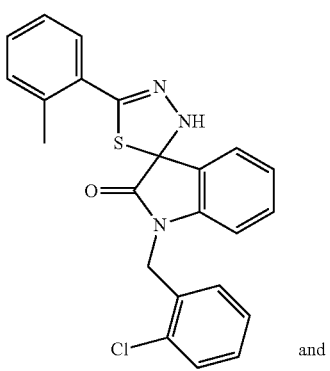
and
-continued
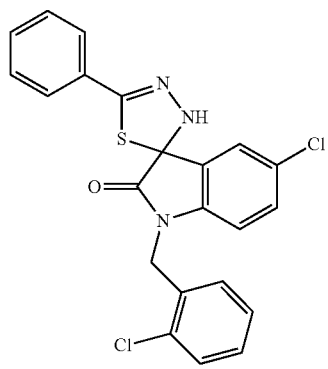
and salts thereof.
In one embodiment the compounds of formula I are selected from:
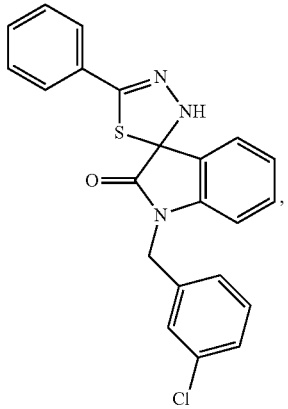
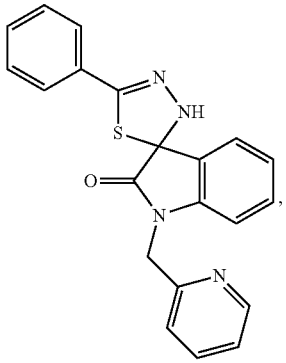
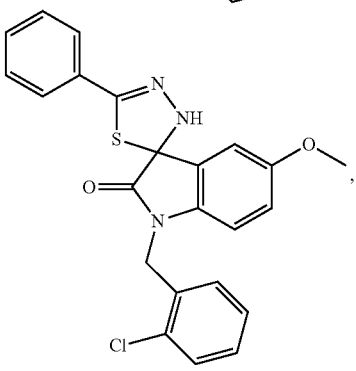

-continued
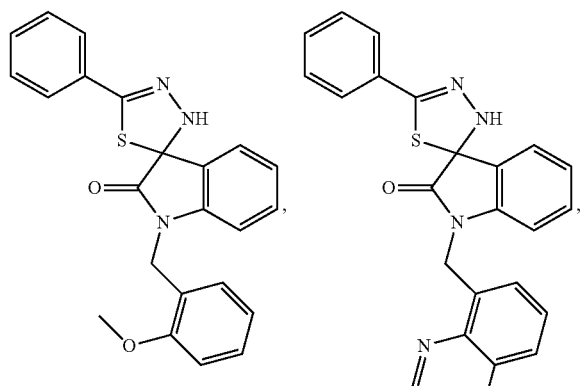
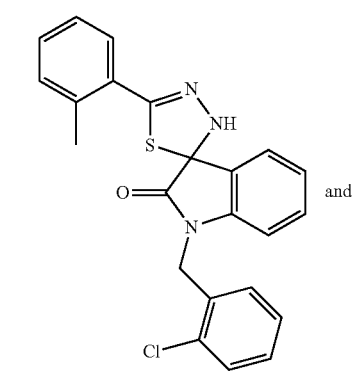
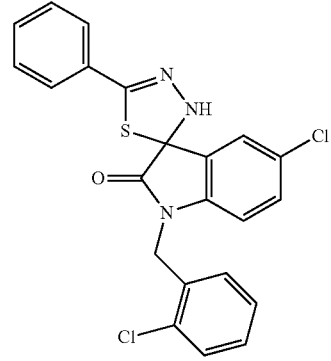
and salts thereof.
In one embodiment the compounds of formula I are selected from:
-continued
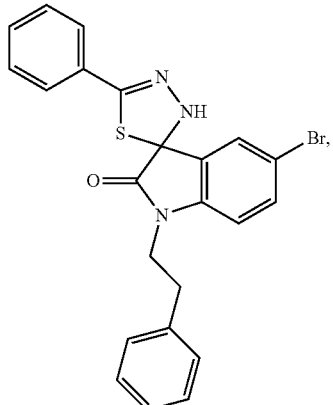
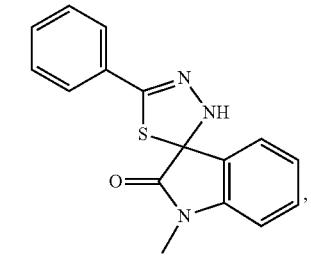
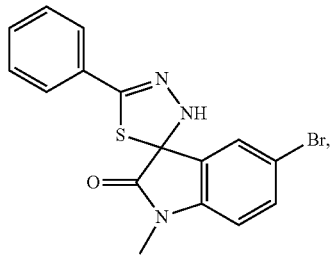
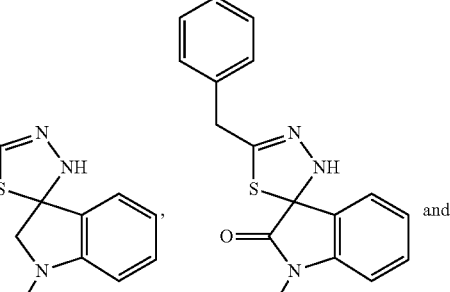
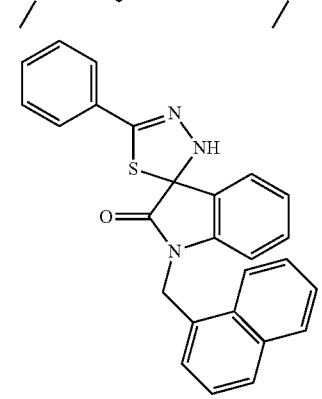
and pharmaceutically acceptable salts thereof.
In one embodiment the compounds of formula I are selected from:
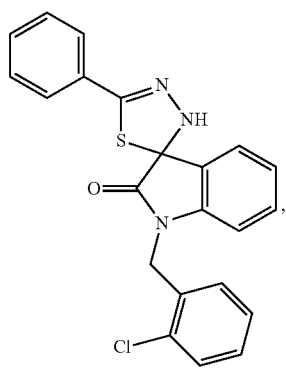

-continued
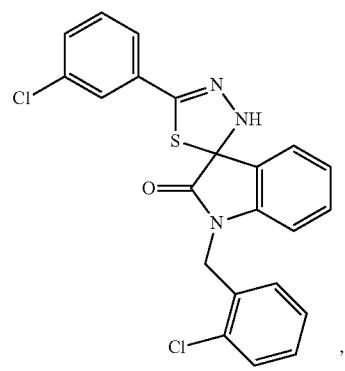
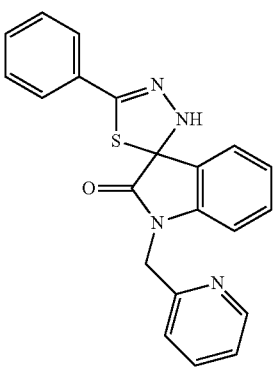
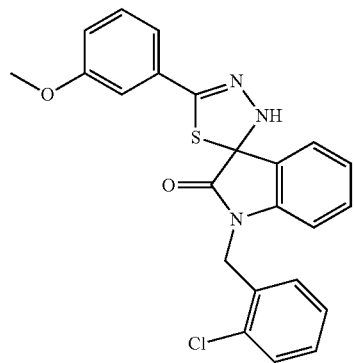
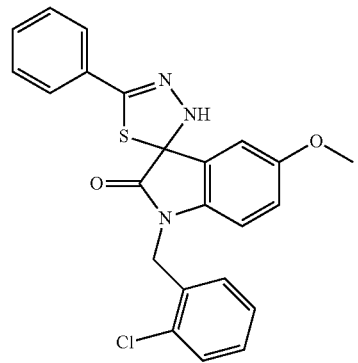
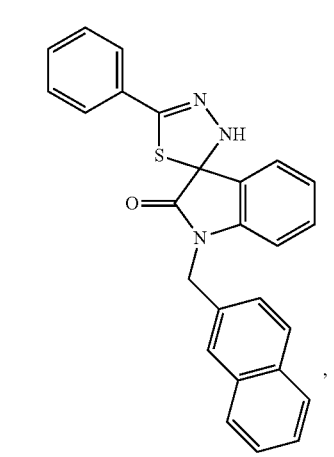
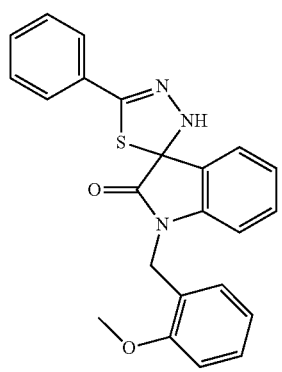
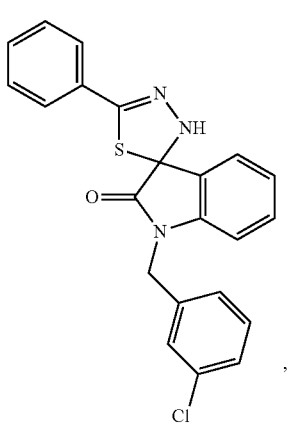
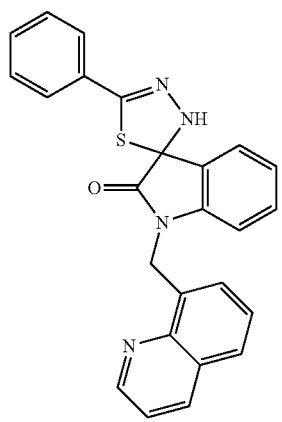

23
-continued
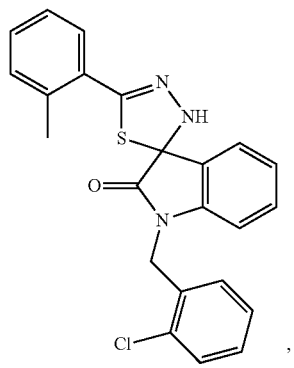
,
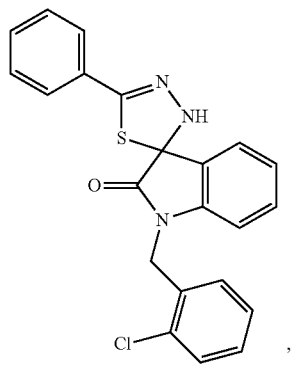
,
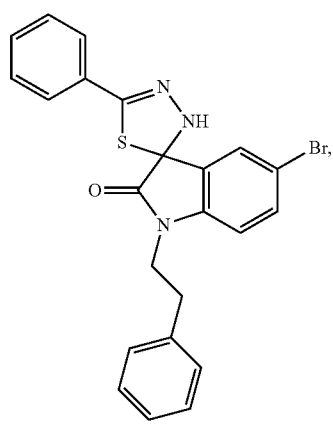
,
24
-continued
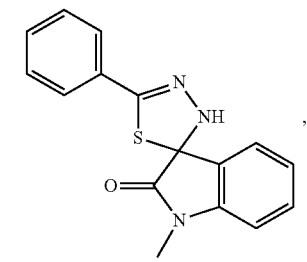
,
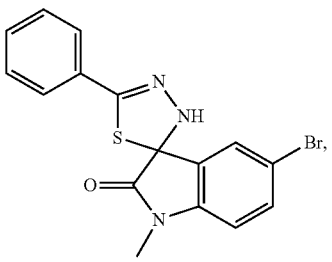
,
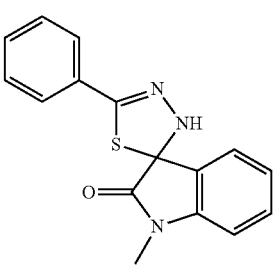
,
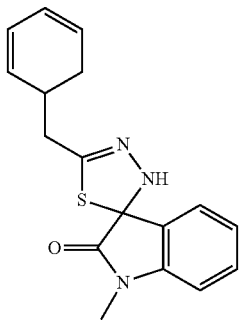
and -continued
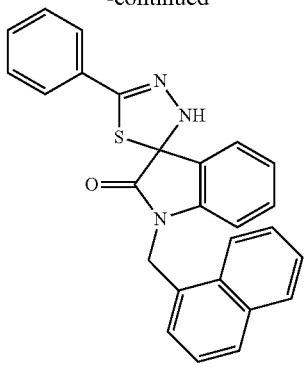
and pharmaceutically acceptable salts thereof.
In one embodiment the compounds of formula I are selected from:
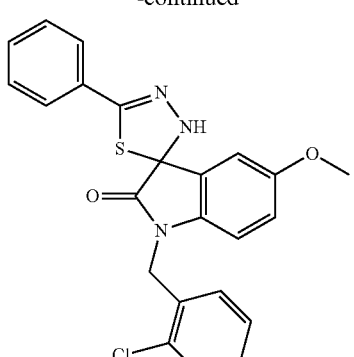
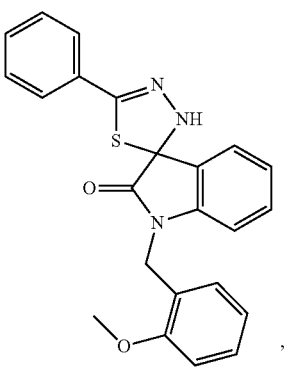
,
-continued
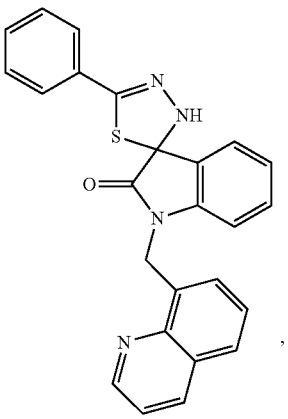
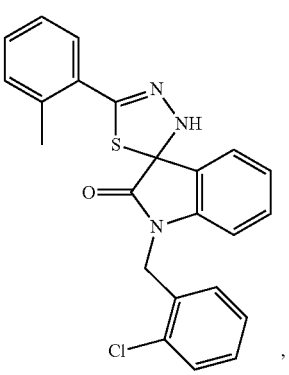

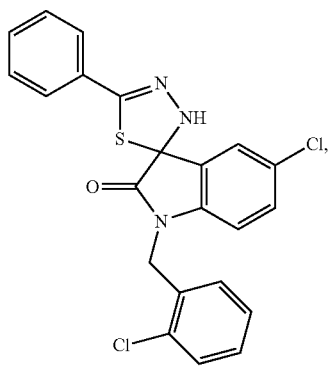
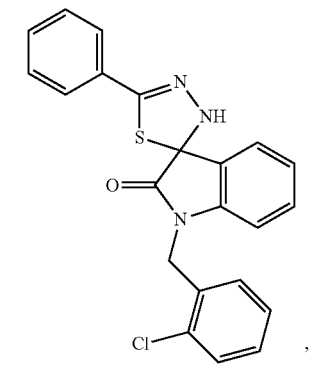
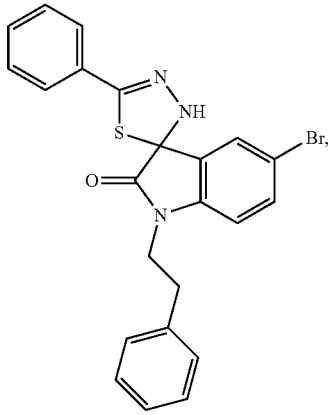
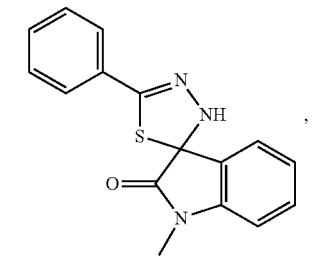
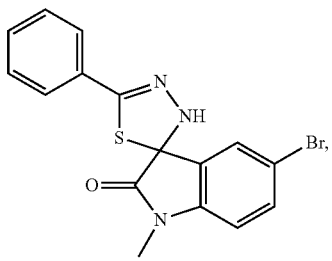
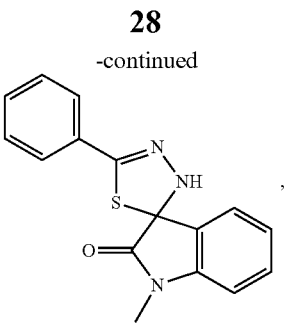
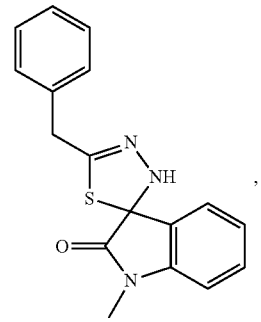
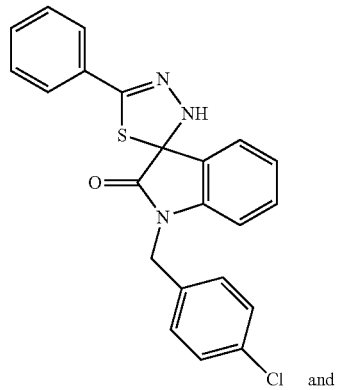
and
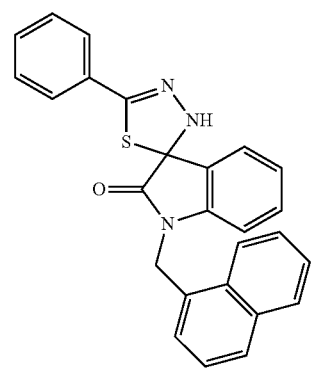 [SMILES: O=C1N(Cc2cccc3ccccc23)c2ccccc2C12NN=C(c1ccccc1)S2]
and pharmaceutically acceptable salts thereof.
In one embodiment, the invention provides a method for treating breast cancer in a mammal (e.g. a human) comprising administering to the mammal an effective amount of a compound of formula I:

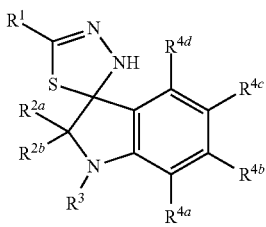

I wherein:

R[1] is aryl or —($C_1$-$C_6$)alkylaryl, wherein any aryl or —($C_1$-$C_6$)alkylaryl of R[1] is optionally substituted with one or more (e.g. 1, 2, 3, 4 or 5) groups selected from ($C_1$-$C_6$) alkyl, ($C_2$-$C_6$)alkenyl, ($C_2$-$C_6$)alkynyl, ($C_3$-$C_7$)carbocycle, halogen, —CN, —$OR_{n1}$, —$NR_{q1}R_{r1}$, —$NR_{n1}COR_{p1}$, $NO_2$, —C(O)$R_{n1}$ and —C(O)$OR_{n1}$;

$R^{2a}$ and $R^{2b}$ are each H, or $R^{2a}$ and $R^{2b}$ together are =O;

R[3] is H, ($C_1$-$C_6$)alkyl or —($C_1$-$C_6$)alkylaryl, wherein any ($C_1$-$C_6$)alkyl of R[3] is optionally substituted with one or more (e.g. 1, 2, 3, 4 or 5) $Z^1$ groups and wherein any —($C_1$-$C_6$) alkylaryl is optionally substituted with one or more (e.g. 1, 2, 3, 4 or 5) groups selected from $Z^1$, ($C_1$-$C_6$)alkyl, ($C_2$-$C_6$) alkenyl and ($C_2$-$C_6$)alkynyl;

$R^{4a}$ is H, ($C_1$-$C_8$)alkyl, ($C_2$-$C_6$)alkenyl, ($C_2$-$C_6$)alkynyl, ($C_3$-$C_7$)carbocycle, halogen, —CN, —$OR_{n3}$, —$NR_{q3}R_{r3}$, —$NR_{n3}COR_{p3}$, $NO_2$, —C(O)$R_{n3}$ or —C(O)$OR_{n3}$;

$R^{4b}$ is H, ($C_1$-$C_8$)alkyl, ($C_2$-$C_8$)alkenyl, ($C_2$-$C_8$)alkynyl, ($C_3$-$C_7$)carbocycle, halogen, —CN, —$OR_{n3}$, —$NR_{q3}R_{r3}$, —$NR_{n3}COR_{p3}$, $NO_2$, —C(O)$R_{n3}$ or —C(O)$OR_{n3}$;

$R^{4c}$ is H, ($C_1$-$C_8$)alkyl, ($C_2$-$C_8$)alkenyl, ($C_2$-$C_8$)alkynyl, ($C_3$-$C_7$)carbocycle, halogen, —CN, —$OR_{n3}$, —$NR_{q3}R_{r3}$, —$NR_{n3}COR_{p3}$, $NO_2$, —C(O)$R_{n3}$ or —C(O)$OR_{n3}$;

$R^{4d}$ is H, ($C_1$-$C_8$)alkyl, ($C_2$-$C_8$)alkenyl, ($C_2$-$C_8$)alkynyl, ($C_3$-$C_7$)carbocycle, halogen, —CN, —$OR_{n3}$, —$NR_{q3}R_{r3}$, —$NR_{n3}COR_{p3}$, $NO_2$, —C(O)$R_{n3}$ or —C(O)$OR_{n3}$;

each $Z^1$ is independently selected from ($C_3$-$C_7$)carbocycle, halogen, —CN, —$OR_{n2}$, —$NR_{q2}R_{r2}$, —$NR_{n2}COR_{p2}$, $NO_2$, —C(O)$R_{n2}$ and —C(O)$OR_{n2}$;

each $R_{n1}$ is independently selected from H, ($C_1$-$C_6$)alkyl, ($C_2$-$C_6$)alkenyl, ($C_2$-$C_6$)alkynyl and ($C_3$-$C_7$)carbocycle;

each $R_{p1}$ is independently selected from ($C_1$-$C_6$)alkyl, ($C_2$-$C_6$)alkenyl, ($C_2$-$C_6$)alkynyl and ($C_3$-$C_7$)carbocycle;

$R_{q1}$ and $R_{r1}$ are each independently selected from H, ($C_1$-$C_6$)alkyl, ($C_2$-$C_6$)alkenyl, ($C_2$-$C_6$)alkynyl and ($C_3$-$C_7$) carbocycle, or $R_{q1}$ and $R_{r1}$ together with the nitrogen to which they are attached form a heterocycle;

each $R_{n2}$ is independently selected from H, ($C_1$-$C_6$)alkyl, ($C_2$-$C_6$)alkenyl, ($C_2$-$C_6$)alkynyl and ($C_3$-$C_7$)carbocycle;

each $R_{p2}$ is independently selected from ($C_1$-$C_6$)alkyl, ($C_2$-$C_6$)alkenyl, ($C_2$-$C_6$)alkynyl and ($C_3$-$C_7$)carbocycle;

$R_{q2}$ and $R_{r2}$ are each independently selected from H, ($C_1$-$C_6$)alkyl, ($C_2$-$C_6$)alkenyl, ($C_2$-$C_6$)alkynyl and ($C_3$-$C_7$) carbocycle, or $R_{q2}$ and $R_{r2}$ together with the nitrogen to which they are attached form a heterocycle;

each $R_{n3}$ is independently selected from H, ($C_1$-$C_6$)alkyl, ($C_2$-$C_6$)alkenyl, ($C_2$-$C_6$)alkynyl and ($C_3$-$C_7$)carbocycle;

each $R_{p3}$ is independently selected from ($C_1$-$C_6$)alkyl, ($C_2$-$C_6$)alkenyl, ($C_2$-$C_6$)alkynyl and ($C_3$-$C_7$)carbocycle; and $R_{q3}$ and $R_{r3}$ are each independently selected from H, ($C_1$-$C_6$)alkyl, ($C_2$-$C_6$)alkenyl, ($C_2$-$C_6$)alkynyl and ($C_3$-$C_7$) carbocycle, or $R_{q3}$ and $R_{r3}$ together with the nitrogen to which they are attached form a heterocycle;

or a pharmaceutically acceptable salt thereof.

In one embodiment the compounds of formula I do not include the compounds of formula:

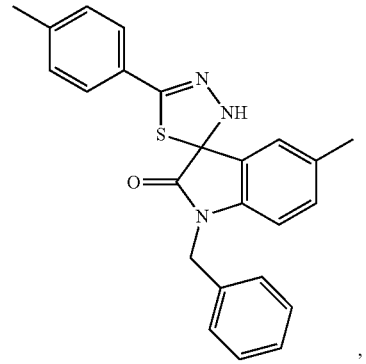

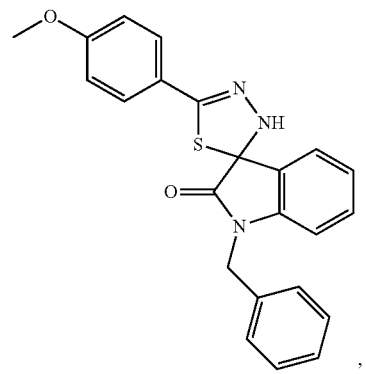

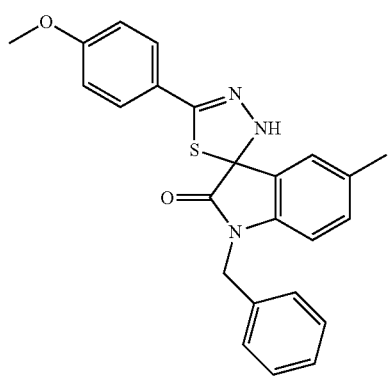

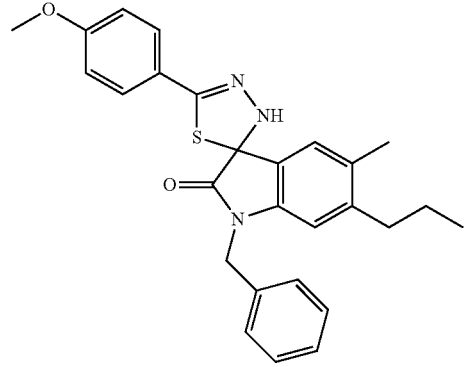

31
-continued
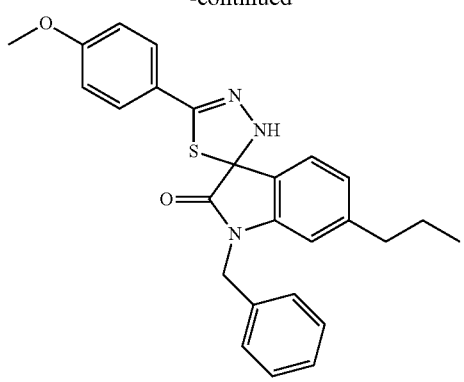
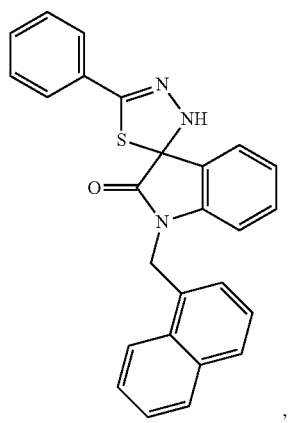
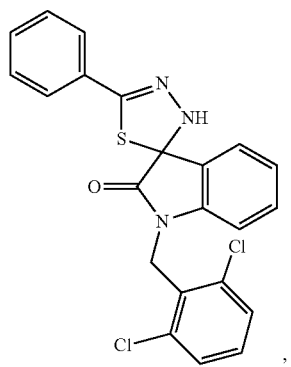
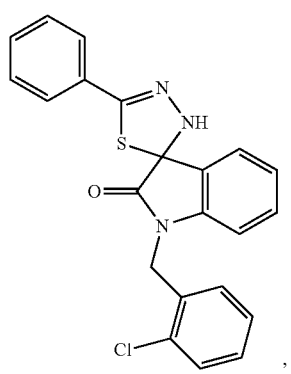
32
-continued
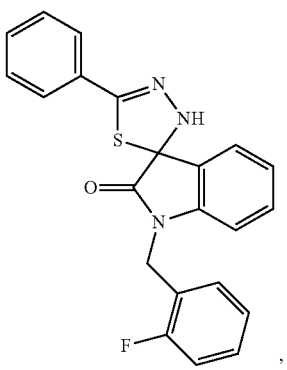
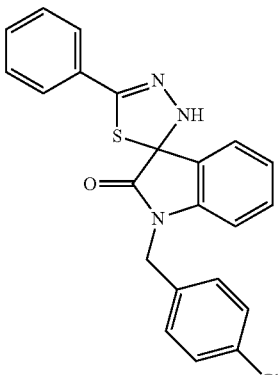
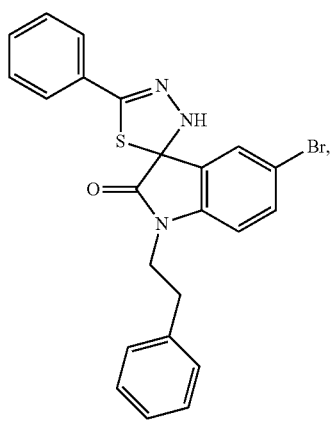
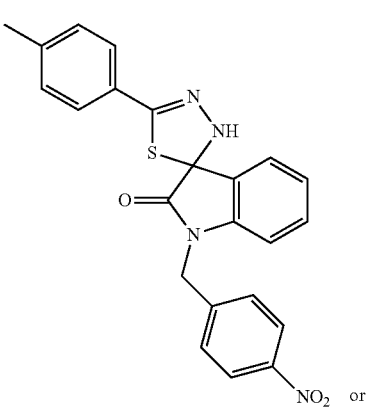
or

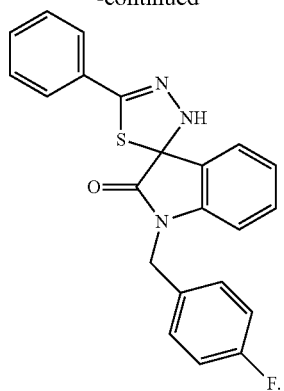
In one embodiment the compounds of formula I do not include the compounds of formula:
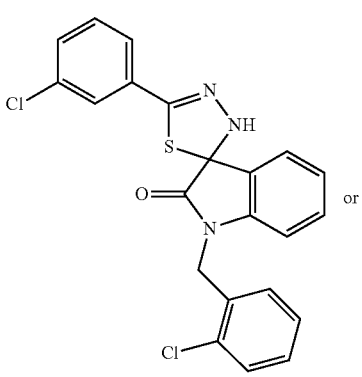
or
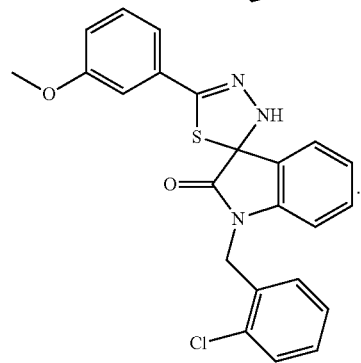
.
In one embodiment the compounds of formula I are selected from:
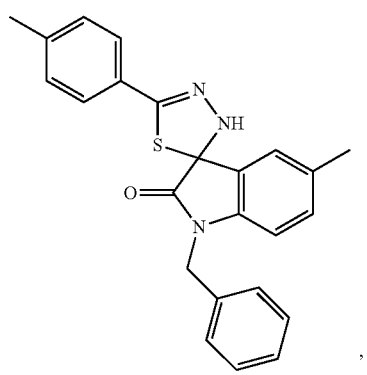
,
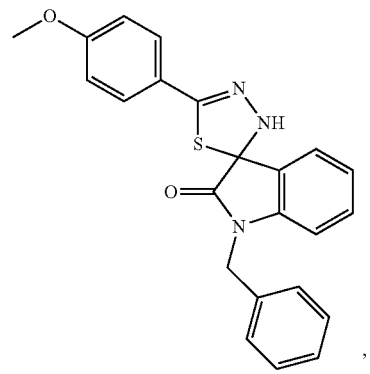
,
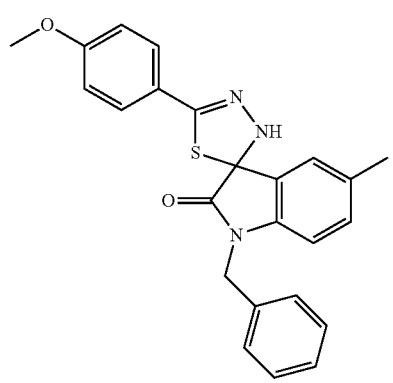
,
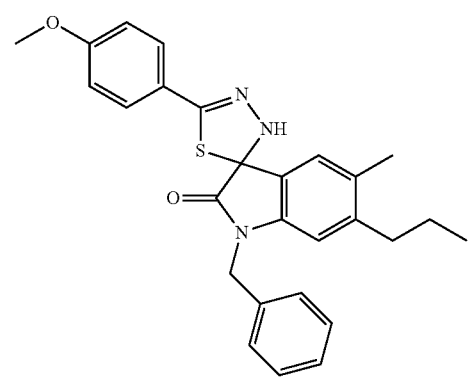
,
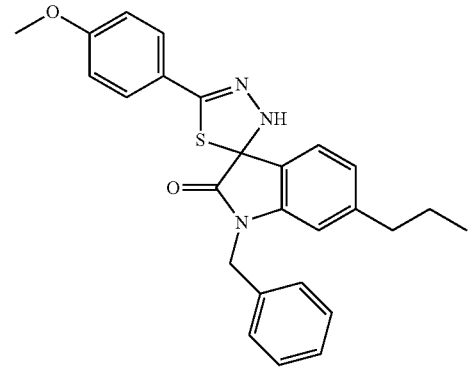
, -continued
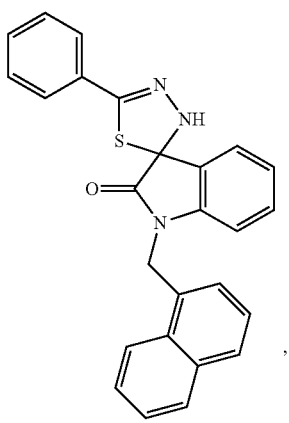
,
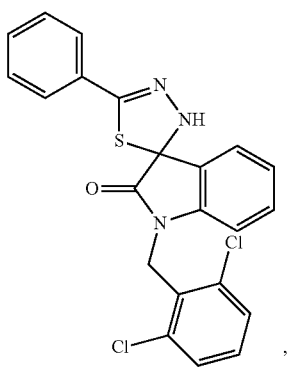
,
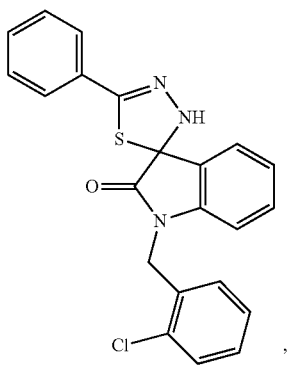
,
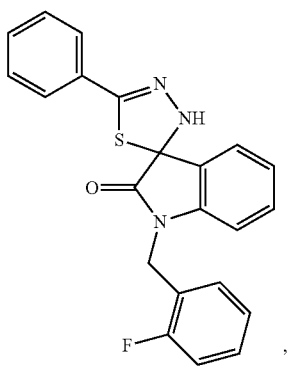
,
-continued
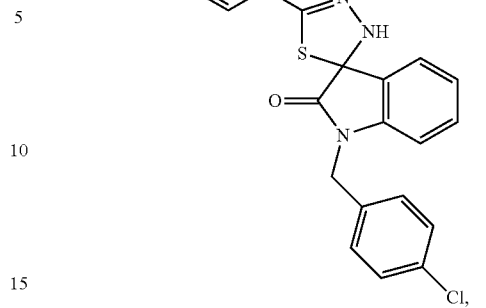
,
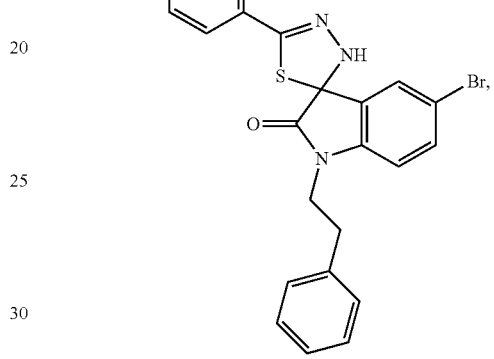
,
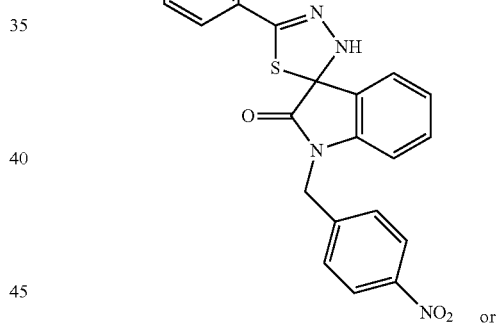  or
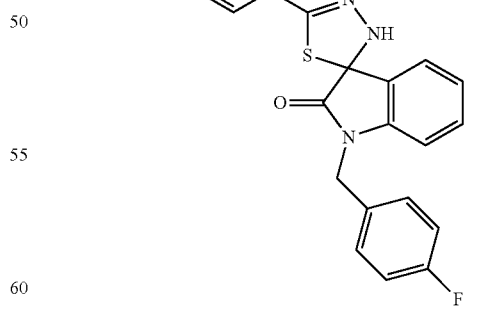
and pharmaceutically acceptable salts thereof.
Human breast cancers, in general, can be divided into three broad categories. A majority (~60-70%) of breast cancers are the luminal type breast cancers with positive expression of estradiol and progesterone receptors (ER/PR).

These cancers are often treated with drugs that target estradiol receptor (e.g. Tamoxifen and related anti-estrogens) or the estradiol biosynthesis pathway (e.g. Fulvestrant/Faslodex). Tamoxifen-resistant breast cancers have been a significant problem in the clinic.

Another class of breast cancers that lack ER/PRs are classified as ER-negative cancers. These ER-negative cancers can be divided into two subsets. The ER-negative cancers with overexpression of human EGFR (HER)-2/ErbB2 oncogene are often treated with anti-Her-2 antibodies (Herceptin). The ER-negative cancers that lack ER/PR as well as Her-2 are categorized as "triple negative" breast cancers (TNBC). Treatments for TNBSs include the anthracycline toxin adriamycin, EGFR antibodies (e.g. Cetuximab), and/or radiation combined with surgery. Breast cancers with resistance to herceptin or adriamycin have also been frequently encountered.

The compounds of formula I have been found to inhibit the growth of breast cancer cells including drug resist breast cancer cells such as tamoxifen and adriamycin-resistant breast cancer cells. Thus, the compounds of formula I and formula II provide a novel avenue to develop treatment options for combating breast cancers, including triple negative and her-2-positive breast cancers, as well as drug resistant breast cancers thereof, including drug-resistant luminal type breast cancers as well as TNBCs.

Accordingly, the invention provides compounds of formula I and formula II and methods, uses and medicaments utilizing compounds of formula I and formula II for treating breast cancers including drug resistant breast cancers. The invention also provides compounds of formula I and formula II and methods, uses and medicaments utilizing compounds of formula I and formula II for treating triple negative and her-2-positive breast cancers, as well as drug resistant breast cancer variants thereof. The invention also provides compounds of formula I and formula II and methods, uses and medicaments utilizing compounds of formula I and formula II for treating pancreatic cancer and/or mesotheliomas.

In one embodiment the invention provides a method to treat breast cancer in a mammal (e.g. a human) in need of such treatment comprising administering to the mammal a compound of formula I, or a pharmaceutically acceptable salt thereof.

In another embodiment the invention provides a method to treat a drug resistant breast cancer in a mammal (e.g. a human) in need of such treatment comprising administering to the mammal a compound of formula I, or a pharmaceutically acceptable salt thereof.

In another embodiment the invention provides a method to treat breast cancer in a mammal (e.g. a human) diagnosed with breast cancer, comprising administering to the mammal a compound of formula I, or a pharmaceutically acceptable salt thereof.

In another embodiment the invention provides a method to treat a drug resistant breast cancer in a mammal (e.g. a human) diagnosed with drug resistant breast cancer, comprising administering to the mammal a compound of formula I, or a pharmaceutically acceptable salt thereof.

The invention provides a method for treating breast cancer, including drug resistant breast cancer or mesothelial lung cancer in a mammal (e.g. a human) comprising administering to the mammal an effective amount of a compound of formula II (e.g. CFM-5):

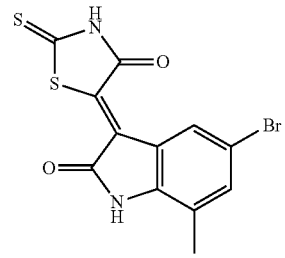

or a salt thereof.

The invention also provides a pharmaceutical composition for the treatment of breast cancer, including a drug resistant breast cancer, or mesothelial lung cancer comprising a compound of formula II, or a pharmaceutically acceptable salt thereof, in combination with a pharmaceutically acceptable carrier.

The invention also provides a compound of formula II, or a pharmaceutically acceptable salt thereof, or composition of formula II, for use in the prophylactic or therapeutic treatment of breast cancer, including a drug resistant breast cancer, or mesothelial lung cancer.

The invention also provides a compound of formula II, or a pharmaceutically acceptable salt thereof, or composition of formula II, for use in the manufacture of a medicament for the treatment of breast cancer, including a drug resistant breast cancer, or mesothelial lung cancer in a mammal (e.g. a human).

In one embodiment the invention provides a method to treat breast cancer in a mammal (e.g. a human) in need of such treatment comprising administering to the mammal a compound of formula II, or a pharmaceutically acceptable salt thereof.

In another embodiment the invention provides a method to treat a drug resistant breast cancer in a mammal (e.g. a human) in need of such treatment comprising administering to the mammal a compound of formula II, or a pharmaceutically acceptable salt thereof.

In another embodiment the invention provides a method to treat mesothelial lung cancer in a mammal (e.g. a human) in need of such treatment comprising administering to the mammal a compound of formula II, or a pharmaceutically acceptable salt thereof.

In another embodiment the invention provides a method to treat breast cancer in a mammal (e.g. a human) diagnosed with breast cancer, comprising administering to the mammal a compound of formula II, or a pharmaceutically acceptable salt thereof.

In another embodiment the invention provides a method to treat a drug resistant breast cancer in a mammal (e.g. a human) diagnosed with drug resistant breast cancer, comprising administering to the mammal a compound of formula II, or a pharmaceutically acceptable salt thereof.

In another embodiment the invention provides a method to treat mesothelial lung cancer in a mammal (e.g. a human) diagnosed with mesothelial lung cancer, comprising administering to the mammal a compound of formula II, or a pharmaceutically acceptable salt thereof.

Compound II is commercially available.

In cases where compounds are sufficiently basic or acidic, a salt of a compound of formula I or formula II can be useful as an intermediate for isolating or purifying a compound of formula I or formula II. Additionally, administration of a compound of formula I or formula II as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or formula II can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of formula I or formula II formulated in such a unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of breast cancer including drug resistant breast cancer. Examples of such agents include: (1) agents that treat ER/PR positive, luminal type breast cancers such as agents that target the estradiol receptor (e.g. Tamoxifen and related anti-estrogens) or the estradiol biosynthesis pathway (e.g. Fulvestrant/Faslodex); (2) agents that treat ER-negative cancers which overexpress human EGFR (HER)-2/ErbB2 oncogene (e.g. anti-Her-2 antibodies (Herceptin(Trastuzumab)) and (3) agents that treat ER-negative cancers that lack ER/PR as well as Her-2 (e.g. anthracycline toxin adriamycin, or EGFR antibodies including Erbitrux (Cetuximab). Accordingly, additional therapeutic agents that can be administered with compounds of formula I and II include Tamoxifen, Raloxifen, fulvestrant, Erbitrux (Cetuximab), Iressa, Lapatinib and adriamycin.

Accordingly, in one embodiment the invention provides a composition comprising a compound of formula I or formula II, or a pharmaceutically acceptable salt thereof, at least one other therapeutic agent, and a pharmaceutically acceptable diluent or carrier. The invention also provides a kit comprising a compound of formula I or formula II, or a pharmaceutically acceptable salt thereof, at least one other therapeutic agent, packaging material, and instructions for administering the compound of formula I or formula II or the pharmaceutically acceptable salt thereof and the other therapeutic agent or agents to a mammal to treat cancer including breast cancer and drug resistant breast cancer.

Numerous compounds of formula I are commercially available including the compounds shown directly below. These compounds can be used to prepare additional compounds of formula I. Other compounds of formula I can be prepared from readily available starting materials using standard synthetic techniques.

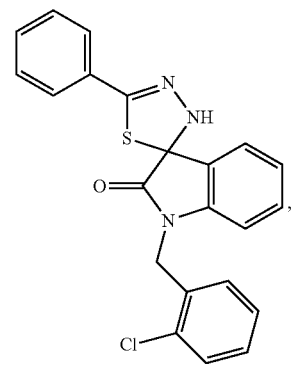

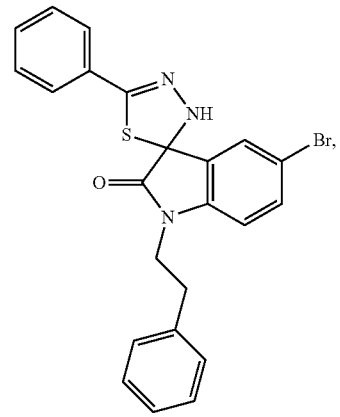

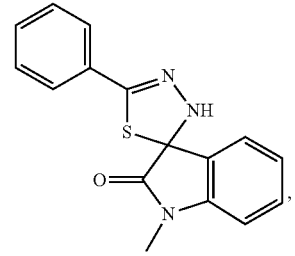

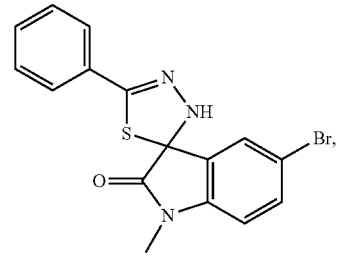

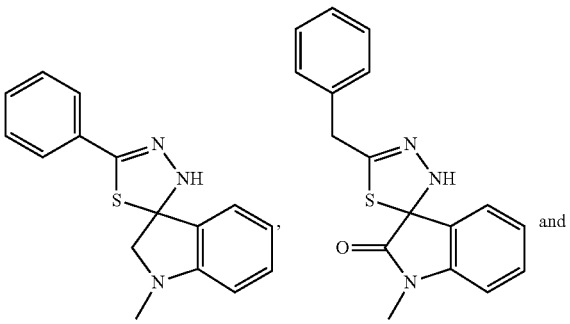

-continued

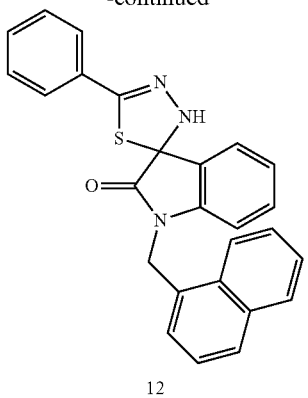

12

The invention will now be illustrated by the following non-limiting Examples.

Example 1

Materials

Figure 2A:
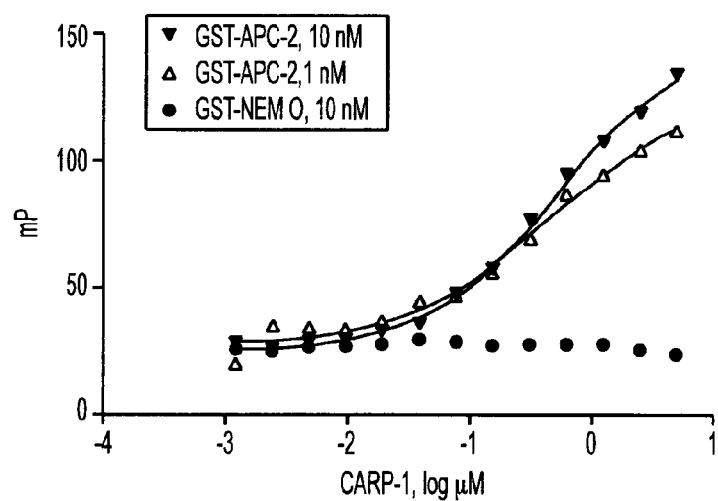
FIGS. 2A-2D: Identification of small molecular antagonists of CARP-1 binding with APC-2. 2A, FP assay for CARP-1-APC-2 binding. Increasing concentrations of fluorescein-tagged A-epitope peptide [CARP-1 (951-980)] were incubated with the indicated quantities of the Gst-APC-2 (685-754) proteins in assay buffer containing 0.01% triton-X100. Gst-NEMO (221-317) was included as a negative control. mP, millipolarization units. 2B, chemical structures of inhibitors of CARP-1 binding with APC-2 identified from HTS. CFM, CARP-1 Functional Mimetic; CFM-1, (Z)-5-(5-bromo-7-methyl-2-oxoindolin-3-ylidene)-2-thioxothiazolidin-4-one; CFM-4,1-(2-chlorobenzyl)-5'-phenyl-3'H-spiro[indoline-3,2'-[1,3,4]thiadiazol]-2-one; CFM-5,5-bromo-1-phenethyl-5'-phenyl-3'H-spiro[indoline-3,2'-[1,3,4]thiadiazol]-2-one. 2C, CFM-4 and CFM-5 bind CARP-1. In left panel, His-TAT-HA-tagged A-epitope peptide was affinity purified and immobilized on beads, incubated with or without CFMs, and then allowed to bind with affinity purified Gst-APC-2 (685-754) as in methods. In right panel, Gst-APC-2 (685-754) peptide was affinity purified and immobilized on beads, incubated with or without CFMs, and then allowed to bind with affinity purified His-TAT-HA-tagged A-epitope peptide. The complexes were analyzed by SDS-PAGE followed by WB with the noted antibodies. Presence of the respective fusion proteins is indicated by an arrowhead on the left side of each blot. 2D, wild-type MDA-MB-468 HBC cells were either untreated or treated with CFM-4 for noted dose and time. Protein complexes were subjected to IP using indicated antibodies. Immunoprecipitates or the respective cell lysates were analyzed by WB with noted antibodies as in FIG. 1A. Presence of endogenous CARP-1 and APC-2 proteins is indicated by an arrowhead on the left side of each blot, while approximate location of various molecular weight markers is indicated on the right side of each blot. kDa, kilodalton.
Figure 2B:
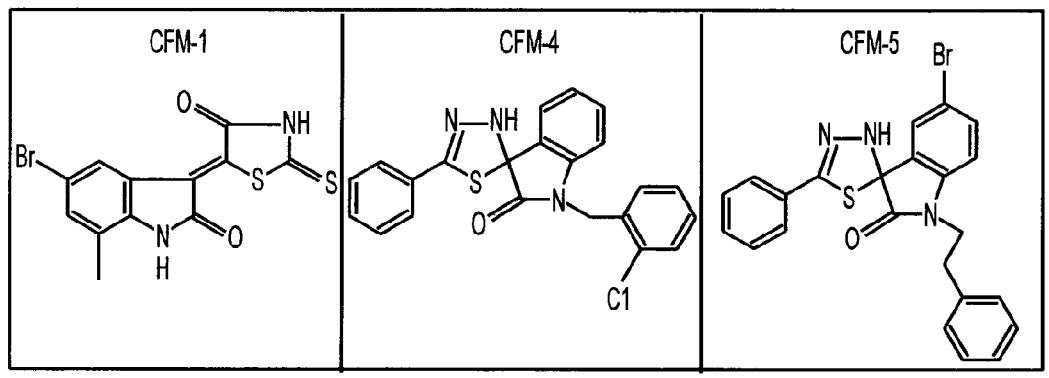

DMEM, Ham's F-12 medium and fetal bovine serum (FBS) was purchased from Life Technologies, Inc., Grand Island, N.Y. The compounds of formula I (CFMs; see FIG. 2) were obtained from ChemDiv, San Diego, Calif., and Ryan Scientific, Inc., Mt. Pleasant, S.C. Clinical grade ADR was from the Harper Hospital Pharmacy, Wayne State University, Detroit, Mich. The pan-caspase inhibitor z-VAD-fmk and caspase 9 inhibitor z-LEHD-fmk were purchased from EMD Chemicals. Caspase 8 inhibitor z-IETD-fmk and caspase 6 inhibitor Ac-VEOD-CHO were obtained from R&D Systems and Enzo Life Sciences, Inc., respectively. The anti-estrogen tamoxifen, and anti-actin, anti-Flag tag, and anti-Cdh1 antibodies were purchased from Sigma Chemical Co, St. Louis, Mo., while Velcade (Bortezomib) was obtained from Millenium (Cambridge, Mass.). The ON-Target plus SiRNAs for knockdown of CARP-1, APC-2, Cdc20, Cdh1, and Bim proteins were purchased from Dharmacon Inc., Thermo Fisher Scientific, Lafayette, Colo. The affinity purified, anti-CARP-1 (a1 and a2) polyclonal antibodies have been described (Rishi, A. K., Zhang, L., Boyanapalli, M., Wali, A., Mohammad, R. M., Yu, Y., Fontana, J. A., Hatfield, J. S., Dawson, M. I., Majumdar, A. P. N., and Reichert, U. (2003) J. Biol. Chem. 278, 33422-33435). Antibodies for Gst-tag, Myc-tag, cyclin B1, p38, phospho-p38, caspases 3, 8, 9, Bim, Bax, Bid, Bad, phospho-Bad, Bcl2, PARP1, p21$^{WAF1/CIP1}$, and Bcl$_{XL}$ were purchased from Cell Signaling, Beverley, Mass. Anti-Cdc20, anti-APC-2, and anti-STAT3 antibodies were obtained from Santa Cruz Biotechnology, Santa Cruz, Calif., and anti-HA tag antibodies were from Covance, Berkeley, Calif. The antibodies for UbCH10 and p27$^{KIP1}$ were purchased from Millipore Corp., Bellerica, Mass. and Novocastra Laboratories, Buffalo Grove, Ill., respectively. The ProBond resin for affinity purification of His-TAT-HA-tagged peptide was purchased from Invitrogen, Corp., while the Gst-Tagged proteins were purified using glutathione sepharose beads (Amersham Biosciences). The plasmid pCMV-SPORT6 having human NEMO (IKKγ) or Deleted in breast cancer (Dbc)-1 (Sundararajan, R., Chen, G., Mukherkee, C., and White, E. (2005) Oncogene 24, 4908-4920) cDNAs were purchased from ATCC (Manassas, Va.), while the plasmids having human APC-2, Cdc20, or Cdh1 cDNAs (Yu, H., Peters, J. M., King, R. W., Page, A. M., Hieter, P., Kirschner, M. W. (1998) Science 279, 1219-1222) were obtained from Addgene (Cambridge, Mass.).

Cloning of cDNAs and Affinity Purification of Various Fusion Proteins:

The plasmid for expression of myc-His-tagged wild-type CARP-1 has been described before (Rishi, A. K., Zhang, L., Boyanapalli, M., Wali, A., Mohammad, R. M., Yu, Y., Fontana, J. A., Hatfield, J. S., Dawson, M. I., Majumdar, A. P. N., and Reichert, U. (2003) J. Biol. Chem. 278, 33422-33435). Expression plasmids encoding myc-His-tagged CARP-1 mutant proteins including the plasmid for expression of CARP-1 having in-frame deletion of amino acids 896 to 978 (that harbor APC-2-interacting epitope) as well as Gst-tagged APC-2 (wild-type and mutant) proteins were generated by standard molecular biological and cloning manipulations and are summarized in FIG. 1B. The ORFs of Cdc20, Cdh1, p38SAPK, Dbc-1, and p53 were PCR amplified using specific sense and anti-sense oligonucleotides for the respective cDNA, and the respective expression plasmids or the reverse transcribed cDNAs as templates. The PCR amplified cDNAs of Cdc20, Cdh1, p38, and p53 were then separately subcloned down-stream of the Gst to obtain recombinant plasmids for expression of respective Gst-tagged proteins. The PCR amplified ORF of Dbc-1 however was subcloned down-stream of the Flag epitope to obtain a recombinant pcDNA3 plasmid for expression of Flag-tagged Dbc-1. In addition, recombinant pGEX/4T plasmids were generated by inserting PCR amplified cDNA fragment of APC-2 and NEMO proteins for expression of Gst-APC-2(685-754) and Gst-NEMO-(221-317) proteins. The APC-2-binding epitope of CARP-1 (A-epitope) from position 951-980 was synthesized as 90-mer each of the sense and antisense oligonucleotides. Additional pair of 90-mer each of the sense and antisense oligonucleotides were synthesized for expression of the scrambled version of the A-epitope (N-GKHKLASVRLRTELTKYNVSKQLCLRLVLF-C, SEQ ID NO:1). The oligonucleotide pair encoding the wild-type or scrambled A-epitope were annealed and ligated downstream of HA-epitope in the pTAT/HA vector (Zhang, L., Levi, E., Majumder, P., Yu, Y., Aboukameel, A., Du, J., Xu, H., Mohammad, R. M., Hatfield, J. S., Wali, A., Adsay, V., Majumdar, A. P. N., and Rishi, A. K. (2007) Mol. Cancer Ther. 6(5), 1661-1672) for expression of wild-type or scrambled His-TAT-HA-CARP-1 (951-980) peptides, respectively. All the recombinant plasmids were sequenced to confirm the accuracy and validity of various inserts/epitopes. The recombinant pGEX and pTAT/HA plasmids were utilized to transform E. coli (BL-21) DE3 strain and independent E. coli isolates expressing respective proteins were obtained. Expression of GST or His-TAT-HA-tagged proteins was induced by IPTG followed by affinity purification of recombinant proteins from bacterial lysates utilizing glutathione sepharose or Probond resin, respectively, using manufacturer suggested protocols essentially as described (Zhang, L., et al., A. K. (2007) Mol. Cancer Ther. 6(5), 1661-1672.)

Cell Lines and Cell Culture:

Routine maintenance and culture of MDA-MB-231, MDA-MB-468, SKBR-3 (all lack ER and have mutant p53), MCF-7, T47D (both have ER and wild-type p53) HBC cells (Runnebaum, I. B., Nagarajan, M., Bowman, M., Soto, D., and Sukumar, S. (1991). Proc. Natl. Acad. Sci. USA 88, 10657-10661), human prostate cancer PC3 and LnCAP cells, HCT-116 human colon cancer, human pancreatic cancer PANC-1 and BxPC-3, Burkett lymphoma Raji, diffuse large B-cell lymphoma WSU-DLCL2, follicular lymphoma WSU-FSCCL cells, cervical cancer HeLa, human mesothelial Met5a, human pleural malignant mesothelioma (MPM), murine MPM AB12 cells (Wang, Y., Rishi, A. K., Puliyappadamba, V. T., Sharma, S., Yang, H., Tarca, A., Dou, Q. P., Lonardo, F., Ruckdeschel, J. C., Pass, H. I., Wali, A. (2010) Can. Chemother. Pharmacol. 66, 455-466), and the green monkey kidney Cos-7 cells was carried out essentially as described (Rishi, A. K., Zhang, L., Boyanapalli, M., Wali, A., Mohammad, R. M., Yu, Y., Fontana, J. A., Hatfield, J. S., Dawson, M. I., Majumdar, A. P. N., and Reichert, U. (2003) J. Biol. Chem. 278, 33422-33435, Rishi, A. K., Zhang, L., Yu, Y., Jiang, Y., Nautiyal, J., Wali, A., Fontana, J. A., Levi, E., and Majumdar, A. P. N. (2006) J. Biol. Chem. 281(19), 13188-98, Zhang, L., Levi, E., Majumder, P., Yu, Y., Aboukameel, A., Du, J., Xu, H., Mohammad, R. M., Hatfield, J. S., Wali, A., Adsay, V., Majumdar, A. P. N., and Rishi, A. K. (2007) Mol. Cancer Ther. 6(5), 1661-1672, Levi, L., Zhang, L., Aboukameel, A., Rishi, S., Mohammad, R. M., Polin, L., Hatfield, J. S., and Rishi, A. K. Can. Chemother. Pharmacol. (in Press). The immortalized, non-tumorigenic human breast epithelial MCF-10A have been described before (Miller, F. R. (2000). J. Mammary Gland Biol. Neoplasia 5, 379-391). MCF-7 cells that are resistant to adriamycin (MCF-7/Adr/Vp) or tamoxifen (MCF-7-TAM) were obtained from Drs. Douglas Ross (University of Maryland Baltimore) and Kaladhar Reddy (Pathology Department, Wayne State University, Detroit, Mich.), respectively, and were maintained essentially following methods described before (Doyle, L. A., Yang, W., Abruzzo, L. V., Krogmann, T., Gao, Y., Rishi, A. K., and Ross, D. D. (1998). Proc. Natl. Acad. Sci. (USA), 95, 15665-15670, Nabha, S., Glaros, S., Hong, M., Lykkesfeidt, A. E., Schiff, R., Osborne, C. K., Reddy, K. B. (2005). Oncogene, 24, 3166-3176). The stable sublines were generated by transfecting the MDA-MB-468 cells with the vector or the recombinant pcDNA3/CARP-1 (Δ896-978)-myc-His plasmid followed by selection in the presence of 800 μg/ml neomycin using described methods (Rishi, A. K., Zhang, L., Boyanapalli, M., Wali, A., Mohammad, R M, Yu, Y., Fontana, J. A., Hatfield, J. S., Dawson, M. I., Majumdar, A. P. N., and Reichert, U. (2003) J. Biol. Chem. 278, 33422-33435).

Immunoprecipitation, Western Blot, MTT and Apoptosis Assays:

Logarithmically growing cells were either untreated or treated with different agents for various time periods. The cells were lysed to prepare protein extracts. IP was carried out by incubating approximately 1 mg of the protein lysate with appropriate antibodies, and the immunoprecipitates or cell lysates were then electrophoresed on 9-12% SDS-polyacrylamide gels, and transferred to nitrocellulose membranes. The membranes were subsequently probed with various antibodies to determine expression/presence of the corresponding proteins. The cell growth inhibition was assessed by using MTT assay. Briefly, MTT (3-[4,5-Dimethylthiazol-2-yl]-2,5diphenyltetrazolium bromide) was dissolved in sterile 1×PBS to prepare a stock solution of 5 mg/ml. The solution was subsequently filtered through 0.2 μm filter and stored at 2-8° C. 4–5×$10^2$ cells were seeded in 96-well plates. After 72 h incubation with or without different agents, MTT stock solution was added to each culture being assayed to equal one tenth the original culture volume, followed by incubation of cells at 37° C. for another 2 h. At the end of the incubation, the media was removed and cells were treated with 100-200 μl of DMSO to solubilize the dye. The assessment of the live cells was derived by measuring the absorbance of the converted dye at wavelength of 570 nm.

Apoptosis levels were determined by utilizing either DNA fragmentation based ELISA or TUNEL kits (Roche Diagnostics, Indianapolis, Ind.) essentially following manufacturer suggested protocols. For apoptosis ELISA assay, 4–5×$10^2$ cells were seeded in 96-well plates and treated essentially as indicated in the MTT assay above. Untreated as well as treated cells were lysed, and levels of mono and oligo-nucleosomal DNA fragments in the lysates were determined by measuring optical density of each sample at 405 nm and 495 nm wavelengths. The "enrichment factor" indicating level of apoptosis was calculated essentially by the manufacturer suggested formula. For TUNEL labeling, the cells were treated with various agents, fixed, labeled and photographed essentially as detailed in immuno-localization protocols described before (Zhang, L., Levi, E., Majumder, P., Yu, Y., Aboukameel, A., Du, J., Xu, H., Mohammad, R. M., Hatfield, J. S., Wali, A., Adsay, V., Majumdar, A. P. N., and Rishi, A. K. (2007) Mol. Cancer. Ther. 6(5), 1661-1672). Activation of caspases was measured by utilizing the ApoAlert Caspase profiling plate (Clontech) essentially following manufacturer suggested guidelines. Cell lysates derived from vehicle DMSO (Control) or CFM-4-treated cells were added to the wells that had immobilized fluorogenic caspase-3, caspase-8, caspase-9, or caspase-2 substrates. The fluorescence released from the activated caspase-dependent cleavage of respective substrate was detected by a plate reader at the excitation and emission wavelengths of 380 nm and 460 nm, respectively.

Fluorescence Polarization Assay:

Although, several formats for FP are indicated in the published literature (Inglese, J., Johnson, R. L., Simeonov, A., Xia, M., Zheng, W., Austin, C. P., Auld, D. S. (2007) Nat. Chem. Biol. 3(8), 466-79), the assays using 96-well or higher density plates are often and routinely employed. Optimization of FP for HTS involves several steps including the determination of $K_d$ values, optimization of the buffer conditions, incubation and measurement times, and determination of the DMSO tolerance of the assay. Our goal was to minimize variation and to aim for adequate signal:background without adversely effecting the sensitivity of the assay. The FP polarization values in milli-polarization (mp) were measured to determine changes in the mp (Amp=mp of bound peptide mp of free peptide), the $K_d$ and $K_i$ constants of the binding. A 30-mer CARP-1 peptide that contained APC-2-binding epitope (A-epitope peptide) was commercially synthesized (US Biologicals, MA), labeled with fluorescein at the N-terminus, and purified to >98% purity. Increasing concentrations of A-epitope peptide were incubated with the indicated quantities of the affinity-purified Gst-APC-2 (685-754) protein in assay buffer containing 0.01% triton-X100. Affinity-purified Gst-NEMO (221-317) was included as a negative control. The Δmp was measured by excitation at 485 nm and emission at 538 nm.

In Vitro Binding of SMIs:

The CFM-4 and 5 were separately dissolved in DMSO to obtain a stock of 20-50 mM. For in vitro binding experiments we utilized affinity-purified Gst-APC-2 (685-754) and His-TAT-HA-tagged A-epitope (WT) peptide. Ten nanogram of the His-TAT-HA-tagged A-epitope (WT) peptide was first allowed to bind with Ni-NTA beads (ProBond, InVitrogen), and then the reaction was incubated with DMSO (control), 100 μM CFM-4, or 100 μM CFM-5 for 30 min at RT. The reactions were then subjected to three washes with the binding buffer, followed by incubation with 10 ng of affinity-purified Gst-APC-2 (685-754) peptide for 30 min at RT. The reactions were washed again for three times with PBS, eluted and analyzed on a SDS-PAGE followed by western blotting (WB) with anti-Gst antibodies. A similar strategy was performed by immobilizing the Gst-APC-2 (685-754) peptide with Gst-beads. The beads were washed, incubated with DMSO or the CFMs, and the reactions washed again. The reactions were then allowed to incubate with affinity purified A-epitope peptide, and the complexes analyzed by SDS-PAGE followed by WB with anti HA-tag antibodies.

Figure 10:
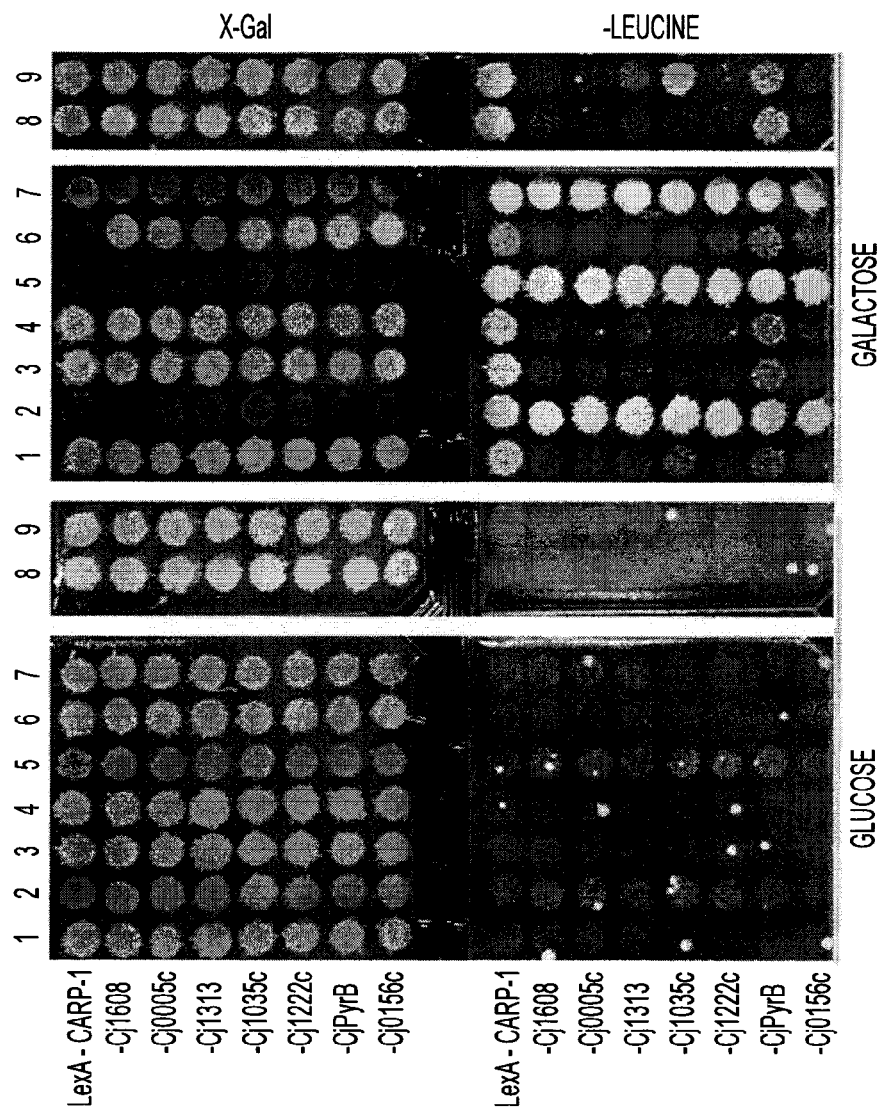
FIG. 10: APC-2 interacts specifically with CARP-1 in a yeast two-hybrid assay. An interaction mating assay (1) in which haploid yeast expressing different LexA fusion proteins (rows) were mated with strains expressing different activation domain (AD) fusion proteins (numbered columns) in 96-well format. The mated yeast were then plated onto four different diploid selection plates: two that contain X-Gal media to detect expression of the lacZ reporter (top), and two that lack leucine to detect expression of the LEU2 reporter by yeast growth (bottom). AD fusion proteins are only expressed only on galactose (right plates) and not on glucose (left plates). LexA fusions include CARP-1 (top row) and seven unrelated proteins that have been shown to interact with other AD proteins in two-hybrid assays (2). LexA-PyrB interacts weakly and nonspecifically with many AD fusion proteins and is included as a control. AD fusions are clones that were isolated from a primary prostate tumor cDNA library using LexA-CARP-1 as bait (Experimental Procedures). Columns 2, 5, and 7 are non-specific clones that were not sequenced. Columns 1, 3, 4 and 9 are four separate clones of HSP5A (NP_005338). The clone in column 8 is filamin-C(NP_001120959). The clone in column 6 is APC-2 (NP_037498). Note that APC-2 interacts strongly with LexA-CARP-1 (blue on galactose X-Gal and growth on galactose leucine), but not with the other LexA fusions.

Yeast Two-Hybrid Screen:

The pNLex(NLS) expression vector (Gyuris, J., Golemis, E., Chertkov, H., and Brent, R. (1993) Cell 75, 791-803), which contains the yeast HIS3 gene and the coding sequences for the LexA DNA-binding domain, was used to express the CARP-1 bait. The full-length CARP-1 coding sequence was excised from the plasmid encoding myc-His-tagged wild-type CARP-1 (Rishi, A. K., Zhang, L., Boyanapalli, M., Wali, A., Mohammad, R. M., Yu, Y., Fontana, J. A., Hatfield, J. S., Dawson, M. I., Majumdar, A. P. N., and Reichert, U. (2003) J. Biol. Chem. 278, 33422-33435) and fused in-frame C-terminal to the LexA DNA-binding domain of pNLex(NLS). The correct orientation and in-frame fusion were confirmed by restriction mapping and DNA sequencing. This bait plasmid containing the LexA-CARP-1 fusion was introduced into yeast strain RFY206, which has the lacZ reporter plasmid pSH18-34 (Finley, R. L. Jr, and Brent, R. (1994) Proc Natl Acad Sci USA. 91(26), 12980-4). The expression of the fusion protein was confirmed by WB analysis using both anti-CARP-1 (α2) and anti-LexA antibodies (not shown). The human primary prostate tumor cDNA library cloned into pJG4-5 plasmid was obtained from OriGene Technology Inc. (Rockville, Md.) and maintained in yeast strain RFY231, which contains LEU2 reporter gene (Kolonin, M. G., and Finley R L Jr. (1998) Proc Natl Acad Sci USA. 95(24), 14266-71). Y2H screening was performed as described (Finley, R. L. Jr, and Brent, R. (1994) Proc Natl Acad Sci USA. 91(26), 12980-4, Kolonin, M. G., and Finley R L Jr. (1998) Proc Natl Acad Sci USA. 95(24), 14266-71). To check whether CARP-1 bait alone would activate the reporter gene LEU2, the bait strain was mated with the RFY231 strain containing the empty pJG4-5 vector (Gyuris, J., Golemis, E., Chertkov, H., and Brent, R. (1993) Cell 75, 791-803). The number of total diploid-forming units (dfu) and Leu$^+$ colonies were counted. The ratio of Leu$^+$ colonies to total dfu was 2 $10^{-7}$, indicating that the background was sufficiently low and that the CARP-1 bait was appropriate for Y2H assay. The yeast strain expressing CARP-1 bait was mated with the prey strain containing the library, and $3 \times 10^6$ dfu were plated onto leucine plates. One hundred ninety two Leu$^+$ colonies were picked and screened for their galactose-dependent reporter activity. Among the 53 galactose-dependent Leu$^+$ colonies, restriction digestion of the cDNA inserts revealed nine unique clones. The prey plasmids were isolated from these nine clones and the specificity of the interactions was tested by re-introducing the plasmids into fresh yeast and conducting two-hybrid assays with the original bait (LexA-CARP-1) and a number of unrelated proteins (FIG. 10). Three clones were non-specific and were not sequenced. The cDNAs in the six specific clones were sequenced. Four of the clones encoded HSP5A (NP_005338), one encoded filamin-C (NP_001120959), and one encoded APC-2 (NP_037498).

Results

CARP-1 Binds with APC/C Subunits APC-2, Cdc20, and Cdh1:

Previous studies have demonstrated that CARP-1 is phosphorylated by diverse signaling pathways, and that CARP-1 inhibited cell growth in part by its interactions with 14-3-3/Stratifin (5) and the PDZ-domain TAZ proteins. Addition studies indicate that CARP-1 regulates ADR-dependent signaling by functioning as a co-activator of tumor suppressor p53, while several proteomic-based studies indicate CARP-1 is a target of phosphorylation by the ATM kinase as well as EGF signaling. Additional, high-throughput proteomic analyses revealed CARP-1 binds with the SAPK/MAPK p38 and the NEMO/IKKγ. However, the nature and context of CARP-1 phosphorylation by ATM or EGF signaling as well as its interactions with NEMO and p38 proteins, and their roles in CARP-1-dependent signaling have not been clarified. In light of the foregoing, it was desired to elucidate CARP-1-dependent signaling mechanisms that regulate cell growth, and postulated that CARP-1 functions in part by interacting with other key cellular proteins to transduce cell growth and apoptosis signaling. As a first step to test this possibility, a Y2H screen was conducted which identified proteins that interact with CARP-1 (Experimental Procedures). One of the proteins that bound specifically to CARP-1 in confirmation Y2H assays was the APC/C E3 ubiquitin ligase component and cullin-homology domain protein APC-2 (FIG. 10).

Additional co-IP-WB experiments were performed to confirm CARP-1 binding with APC-2 protein. Cell lysates from HBC and HeLa cells were subjected to IP using anti-Gst (control) or anti-CARP-1 (a2) antibodies followed by WB with anti-APC-2 antibodies. Alternatively, the cell lysates were also subjected to IP using anti-APC-2 antibodies followed by WB with anti-CARP-1 (a2) antibodies. As expected, APC-2 and CARP-1 proteins were present in the immunoprecipitates derived from anti-CARP-1 and anti-APC-2 antibodies, respectively, demonstrating binding of the cellular CARP-1 and APC-2 proteins (FIG. 1A). Next, the epitopes of CARP-1 and APC-2 proteins that are involved in their mutual binding were mapped.

Figure 1B:
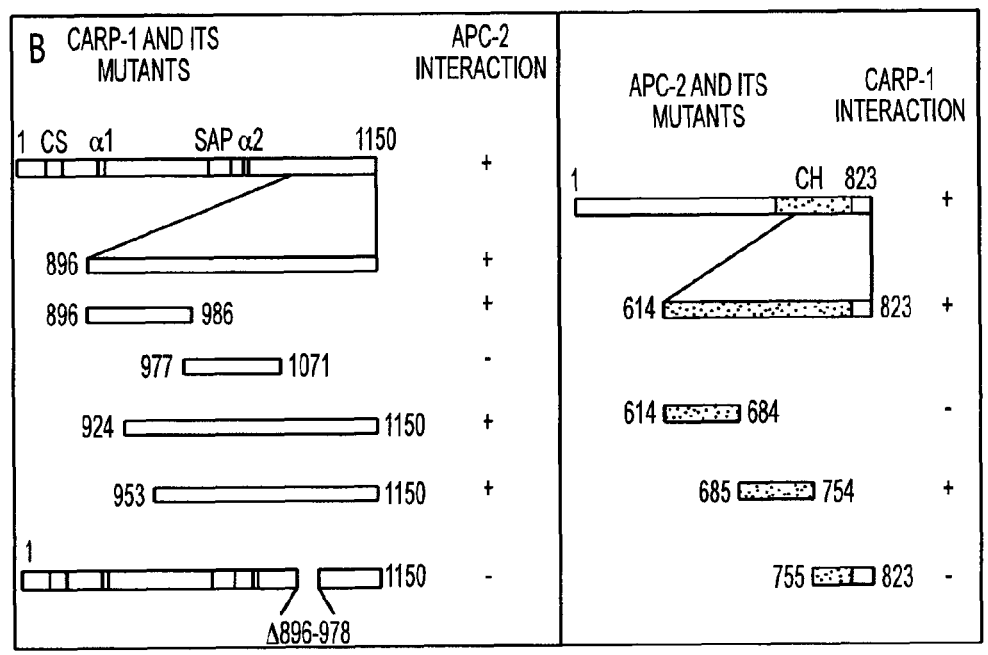
Figures 1C, 1D:
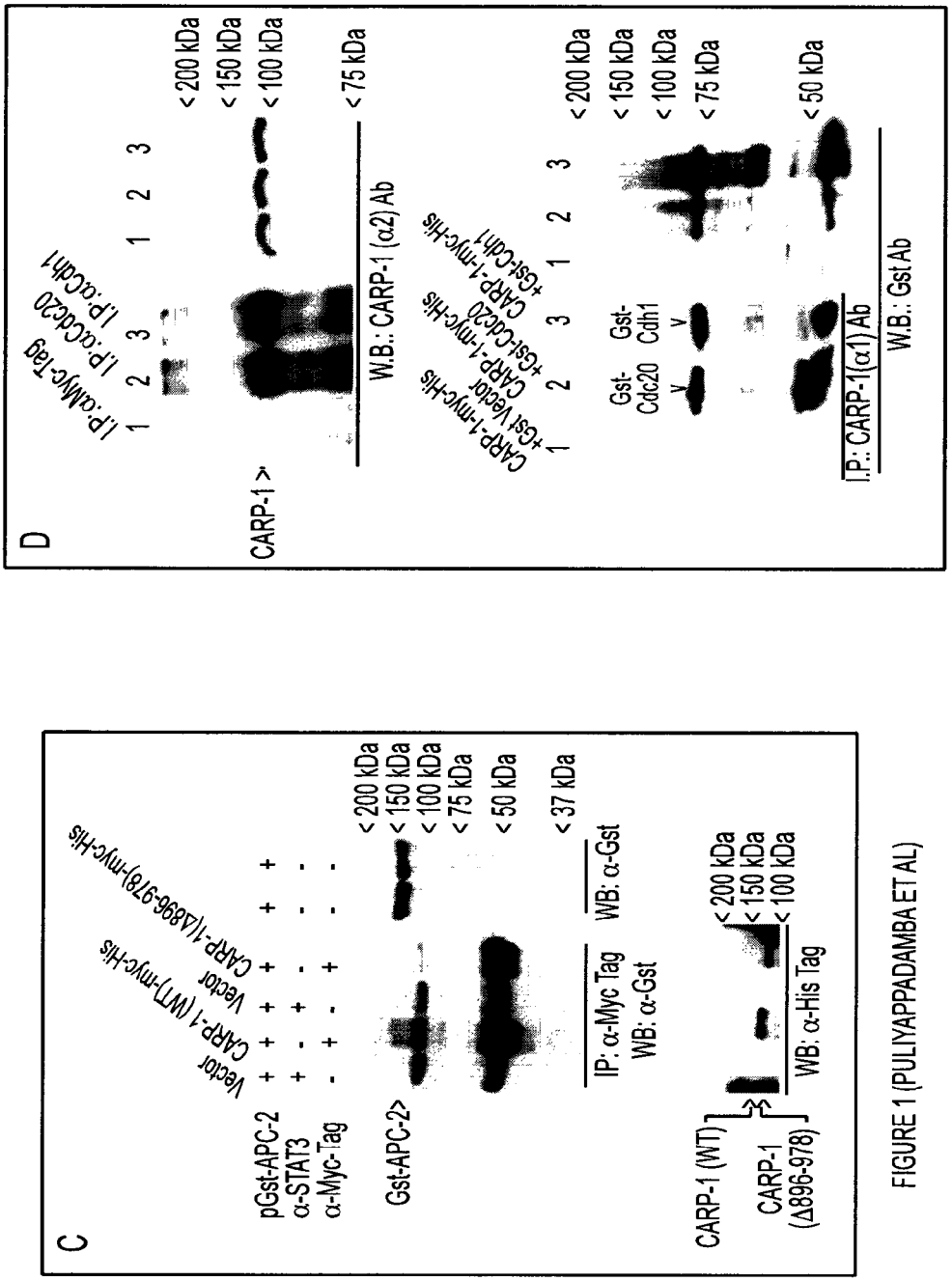
Figures 11A, 11B, 11C, 11D:
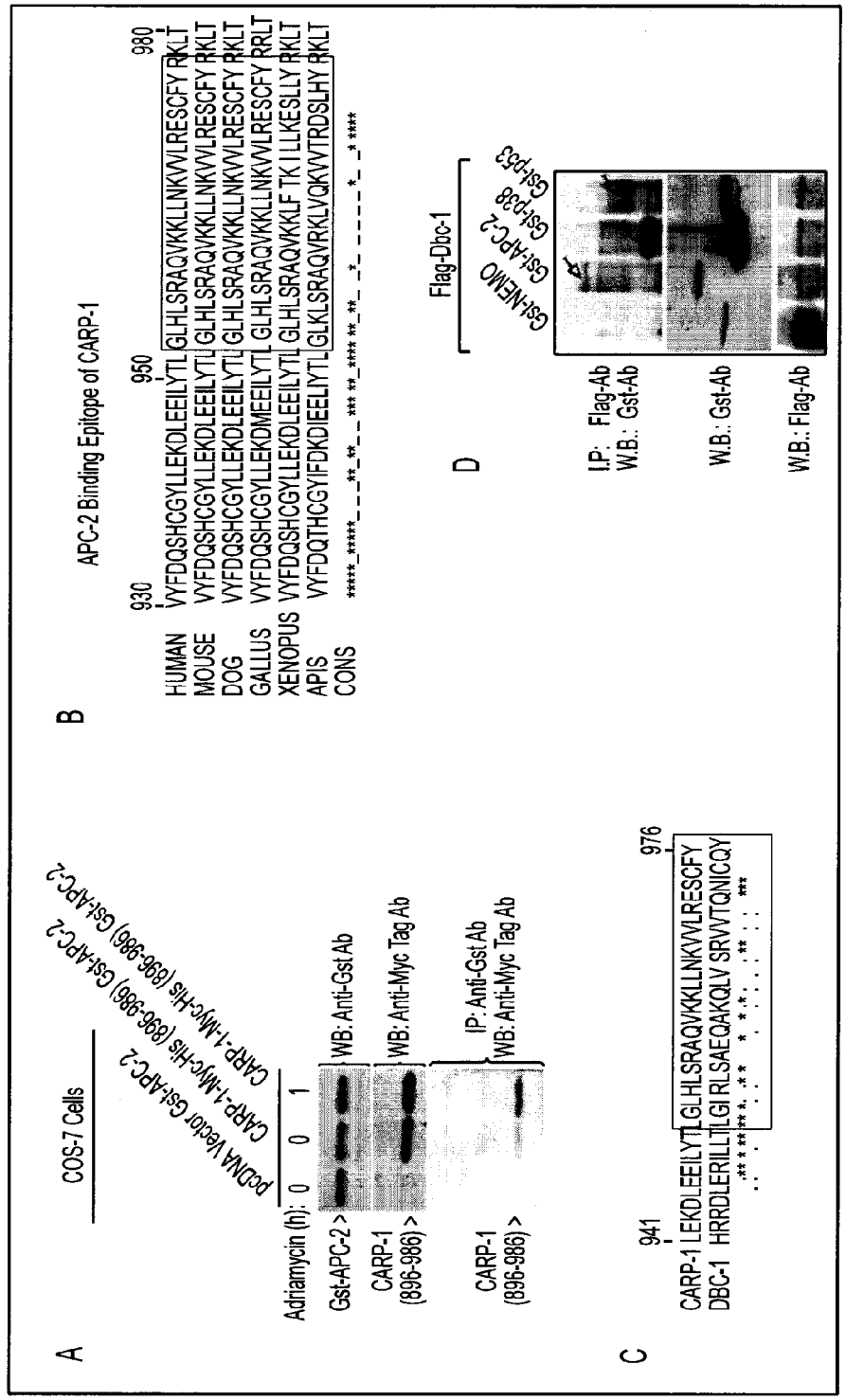
FIGS. 11A-11D: CARP-1 amino-acids 951-980 harbor an epitope for its interaction with APC-2. A, Cells were transfected with plasmid encoding Gst-tagged APC-2 in combination with pcDNA3 vector or CARP-1 (896-986) myc His plasmid as indicated. Cells were then either untreated or treated with ten μg/ml adriamycin for one hour. Fifty μg of protein lysate/lane was subjected to WB with anti-Gst or anti-myc tag antibodies (not shown). One mg of protein lysates were first subjected to IP with anti-Gst antibodies followed by WB of the complexes with anti-myc tag antibodies as in FIG. 1A. Presence of APC-2 interacting CARP-1 (896-986) mutant is indicated on the left side of the middle and lower blots, while Gst-APC-2 presence is indicated on the left side of the upper blot. B, alignment of the carboxyl-terminal regions of CARP-1 proteins of various species with positions 930-980 of the human CARP-1. The APC-2 binding epitope of CARP-1 proteins is indicated inside of the rectangle. C, alignment of human CARP-1 from amino acids 941-976 with the carboxyl-terminal region of human Dbc-1. The APC-2 binding epitope of CARP-1 and the putative APC-2 interacting epitope of Dbc-1 are indicated inside of the shaded rectangle. D, Dbc-1 interacts with APC-2, p38, and p53 but not with NEMO. Cos-7 cells were transfected with plasmid encoding Flag-tagged Dbc-1 in combination with plasmid encoding Gst-tagged NEMO, APC-2, p38, or p53 protein as indicated. Fifty μg of protein lysate/lane was subjected to WB with anti-Gst (middle blot) or anti-Flag tag antibodies (lower blot). One mg of protein lysates were first subjected to IP with anti-Flag antibodies followed by WB of the complexes with anti-Gst tag antibodies as in A above. Presence of Dbc-1-interacting Gst-APC-2, Gst-p38, or Gst-p53 proteins is indicated by arrowheads in upper blot.

For this purpose Cos-7 cells were transfected with various plasmids encoding myc-His-tagged CARP-1 (wild-type and mutant proteins) in combination with plasmids encoding either Gst-tagged wild-type or mutant APC-2 proteins (constructs summarized in FIG. 1B). Cell lysates were subjected to IP with anti-myc or anti-Gst antibodies followed by their WB analyses with anti-Gst or anti-myc antibodies, respectively. These experiments revealed that CARP-1 (896-986) peptide harbored the epitope that interacts with APC-2 protein (FIG. 1B), and an in-frame deletion of the 896-978 region of CARP-1 resulted in loss of its interaction with APC-2 (FIG. 1C). CARP-1 on the other hand interacted with the C-terminal 685-754 region of APC-2 that is located within the cullin-homology domain of APC-2 (FIG. 1B). The APC-2 interacting epitope of CARP-1, termed A-epitope, was further mapped to amino acids 951-980 of the CARP-1 protein (FIGS. 11A and 11B).

The APC/C is composed of a dozen different subunits and has essential functions within and outside of the cell cycle. Association of co-activators Cdc20 and Cdh1 determines APC/C activity during specific cell cycle phases, and is tightly regulated. The activity of the APC/C$^{Cdc20}$ peaks during the late prophase to anaphase to allow smooth transition from spindle assembly checkpoint. The APC/C$^{Cdh1}$, on the other hand, has peak activity during late anaphase to late G1 phase of cell cycle. Given that CARP-1 binds with APC-2, it was desired to clarify whether CARP-1 binding with APC/C was dependent on the APC/C activity during cell-cycle. Co-IP-WB experiments similar to FIG. 1A were conducted to determine whether CARP-1 was present in APC/C$^{Cdc20}$ and/or APC/C$^{Cdh1}$ complexes. HBC Cell lysates were subjected to IP using anti-myc tag (control), anti-Cdc20 or anti-Cdh1 antibodies followed by WB with anti-CARP-1 (α2) antibodies. Alternatively, the Cos-7 cells were first transfected with plasmid encoding myc-His-tagged WT CARP-1 in combination with the Gst vector plasmid or the plasmids encoding Gst-tagged Cdc20 or Cdh1 proteins. The cell lysates were then subjected to IP using anti-CARP-1 (α1) antibodies followed by WB with anti-Gst-tag antibodies. CARP-1 interacted with both Cdc20 and Cdh1 proteins (FIG. 1D). The molecular basis of CARP-1 binding with Cdc20 and Cdh1 proteins by a co-IP-WB was further clarified by an experiment analogous to that of FIG. 1C. Cdh1 interacted with the wild-type CARP-1 as well as the CARP-1 mutant that lacked APC-2-interacting epitope (FIG. 1Ei). In fact, the Cdh1 interacted with the 603-898 region of CARP-1 (FIG. 1Eii). Mutagenesis studies further revealed that like Cdh1, Cdc20 also interacted with an epitope within CARP-1 (761-898) protein (not shown). Data in FIG. 1 suggest that CARP-1, in addition to being a constitutive member of the APC/C, could function as a scaffold to facilitate assembly/activity of APC/C during various phases of cell cycle.

Small molecule inhibitors (SMIs) of CARP-1-APC-2 binding suppress cell growth: The APC/C is a crucial regulator of various cell cycle check-points and since these check-points are often compromised in many cancers, APC/C remains a hotly pursued target for therapeutic intervention. Accordingly, SMIs that target (bind) CARP-1 or APC-2, and, in turn, regulate CARP-1-dependent signaling could inhibit the growth of cells that often have dysregulated APC/C. As a first step to this goal, plasmids for expression of His-TAT-HA-tagged A-epitope and Gst-tagged APC-2 (685-754) proteins were generated, and affinity-purified the fusion proteins from the bacterial lysates as detailed in methods (Zhang, L., Levi, E., Majumder, P., Yu, Y., Aboukameel, A., Du, J., Xu, H., Mohammad, R. M., Hatfield, J. S., Wali, A., Adsay, V., Majumdar, A. P. N., and Rishi, A. K. (2007) Mol. Cancer. Ther. 6(5), 1661-1672, Wadia, J. S., Stan, R. V., and Dowdy, S. F. (2004). Nat. Medicine 10, 310-315). The cell-free interaction of the A-epitope with APC-2 (685-754) was then determined by co-incubating the affinity purified proteins in a binding buffer. Equal amount of Gst-tagged APC-2 (685-754) protein was incubated with buffer, A-epitope (WT), or A-epitope (Scrambled) peptides followed by IP of the complexes with anti-Gst antibodies. The complexes were then subjected to SDS-PAGE analysis followed by WB of the membrane with anti-HA-tag antibodies. This experiment revealed binding of the wild-type A-epitope peptide, but not its scrambled version, with the affinity-purified Gst-APC-2 (685-754) protein (not shown), and thus suggested a direct binding of CARP-1 with APC-2.

The kinetics of CARP-1 binding with APC-2 was determined, and whether this binding could be exploited to identify SMIs of CARP-1-APC-2 interaction was investigated. For this purpose, a FPA utilizing the affinity-purified Gst-APC-2 (685-754) protein and the fluorescein-tagged A-epitope peptide was developed as detailed in methods. The Gst-APC-2 (685-754) binding with the A-epitope peptide had a $K_d$ of 485 nM (FIG. 2A) and 104 nM (not shown) in the presence and absence, respectively, of detergent. The affinity-purified Gst-tagged NEMO (221-317) protein that does not bind with A-epitope peptide did not show any shift in polarization signal (ΔmP). The signal to background ratio of 6 underscored robustness of this assay. Since, the quality (precision) and suitability of the FPA for HTS is usually defined by the Z' factor (25, 40), we utilized the positive and negative control mean signals (μc+ and μc−, respectively) and their standard deviations (σc+ and σc−) to calculate the Z' factor using the equation $Z'=1-[3(\sigma c^+ + \sigma c^-)/(\mu c^+ - \mu c^-)]$. The Z' factor was 0.83 and 0.65 for the 10 nM and 1 nM of Gst-APC-2 (685-754), respectively. The Z' factor however was 0.87 when the detergent was absent from the binding reaction (not shown). Thus, a $K_d$ of 480 nM and a consistent Z' Factors of >0.5 suggested suitability of this assay for single compound HTS.

Figures 2C, 2D:
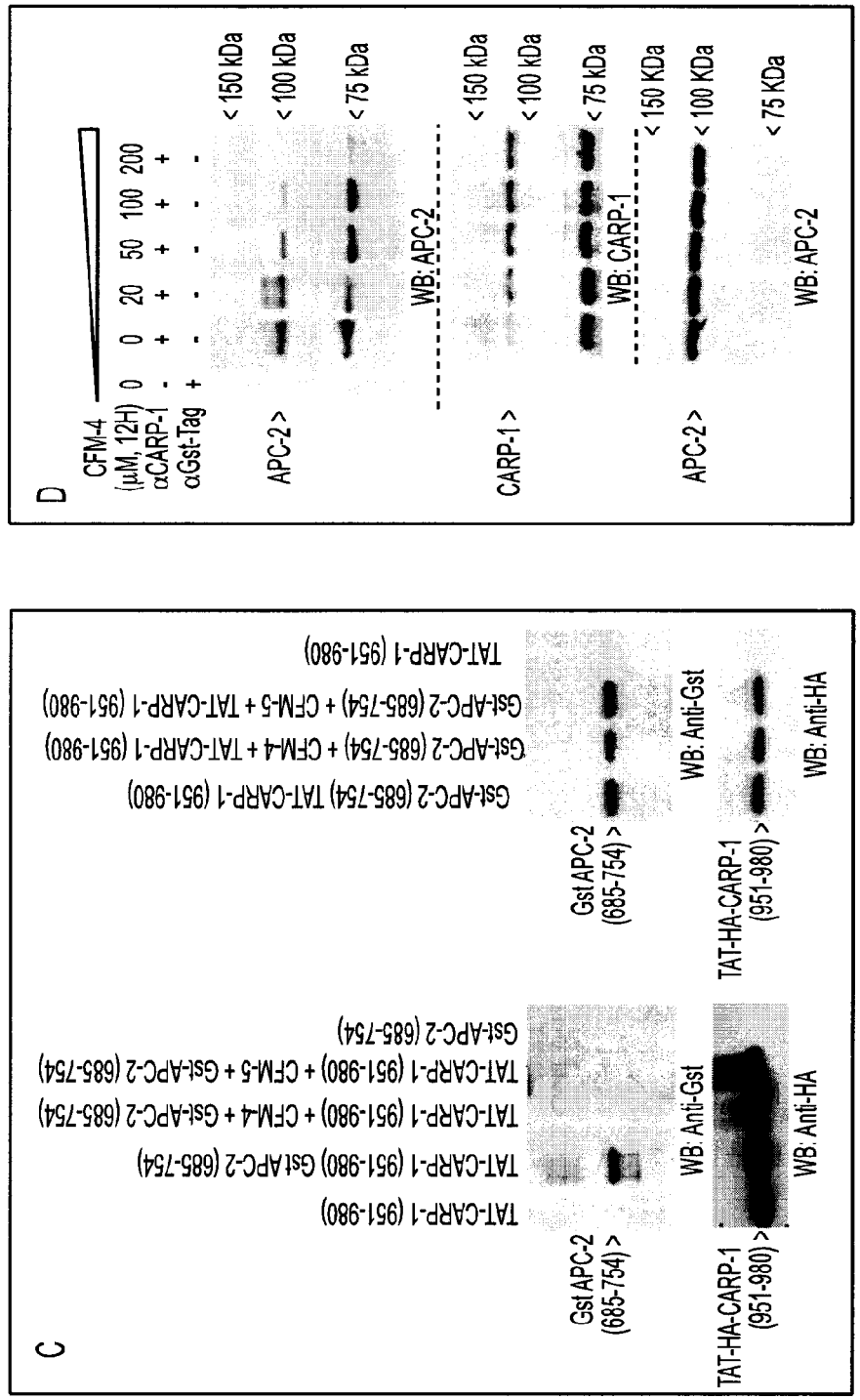

Several active compounds were identified (FIG. 2B) by comparing compound treated mP values to those of the uninhibited control wells from a chemical library of ~10,000 compounds. Dose response assays were then conducted on the active compounds to measure $K_i$ values to select a lead compound for further analyses. Since these compounds could potentially bind with CARP-1 and modulate cell growth, they were named CARP-1 functional mimetics (CFMs). The compounds CFM-1, 4 and 5 displayed an IC50 of 4.1 μM, 0.75 μM, and 1.4 μM, respectively, in the FPA. It was next clarified whether CFM-4 or 5 bind with CARP-1 or APC-2. For this purpose, in vitro binding experiments as detailed in methods were conducted. As expected, the Gst-APC-2 (685-754) bound with the immobilized A-epitope peptide in the reaction that was pre-incubated with DMSO, while pre-incubation of the immobilized A-epitope peptide with CFM-4 or CFM-5 abrogated its binding with Gst-APC-2 (685-754) peptide (FIG. 2C, left panel). Pre-incubation of immobilized Gst-APC-2 (685-754) protein with CFM-4 or CFM-5, on the other hand, failed to abolish its binding with the A-epitope peptide (FIG. 2C, right panel). These data suggest that CFM-4, and -5 bind with CARP-1 A-epitope and consequently prevent its binding with APC-2 in vitro. Whether CFMs also interfere with endogenous interactions of CARP-1 with APC-2 was clarified next. HBC cells were either untreated or treated with escalating doses of CFM-4 for 12 h. Cell lysates were subjected to IP using anti-Gst-tag (control) or anti-CARP-1 (a2) antibodies followed by WB with anti-APC-2 antibodies essentially as in FIG. 1A. Binding of CARP-1 with APC-2 declined in the presence of CFM-4 in a dose-dependent manner, while the levels of CARP-1 but not APC-2 increased in the presence of CFM-4 (FIG. 2D). Taken together, the data in FIG. 2 suggest that CFM-4 and 5 bind with CARP-1, and CFM-4 interferes with endogenous interaction between CARP-1 and APC-2.

Figure 3:
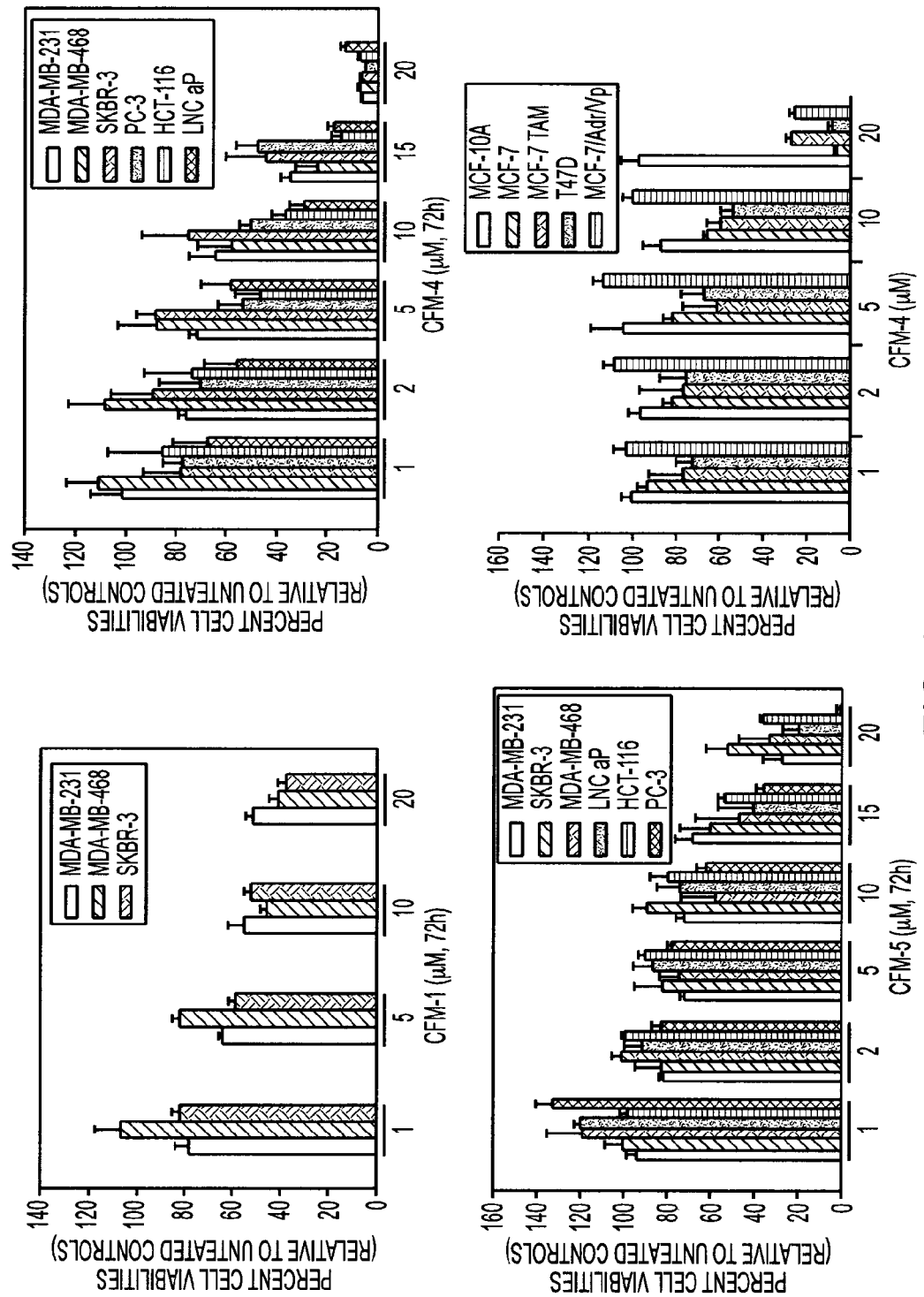
FIG. 3: CFMs inhibit HBC, prostate, and colon cancer cell growth, but do not inhibit growth of immortalized, non-tumorigenic mammary epithelial MCF-10A cells. Cell viability was determined by MTT assay following treatments of cells with vehicle/DMSO (Control) or indicated time and doses of various CFMs. The columns in each histogram indicate percent of live/viable cells relative to their vehicle/DMSO-treated controls, and represent means of three-four independent experiments; bars, S.E.
Figure 12:
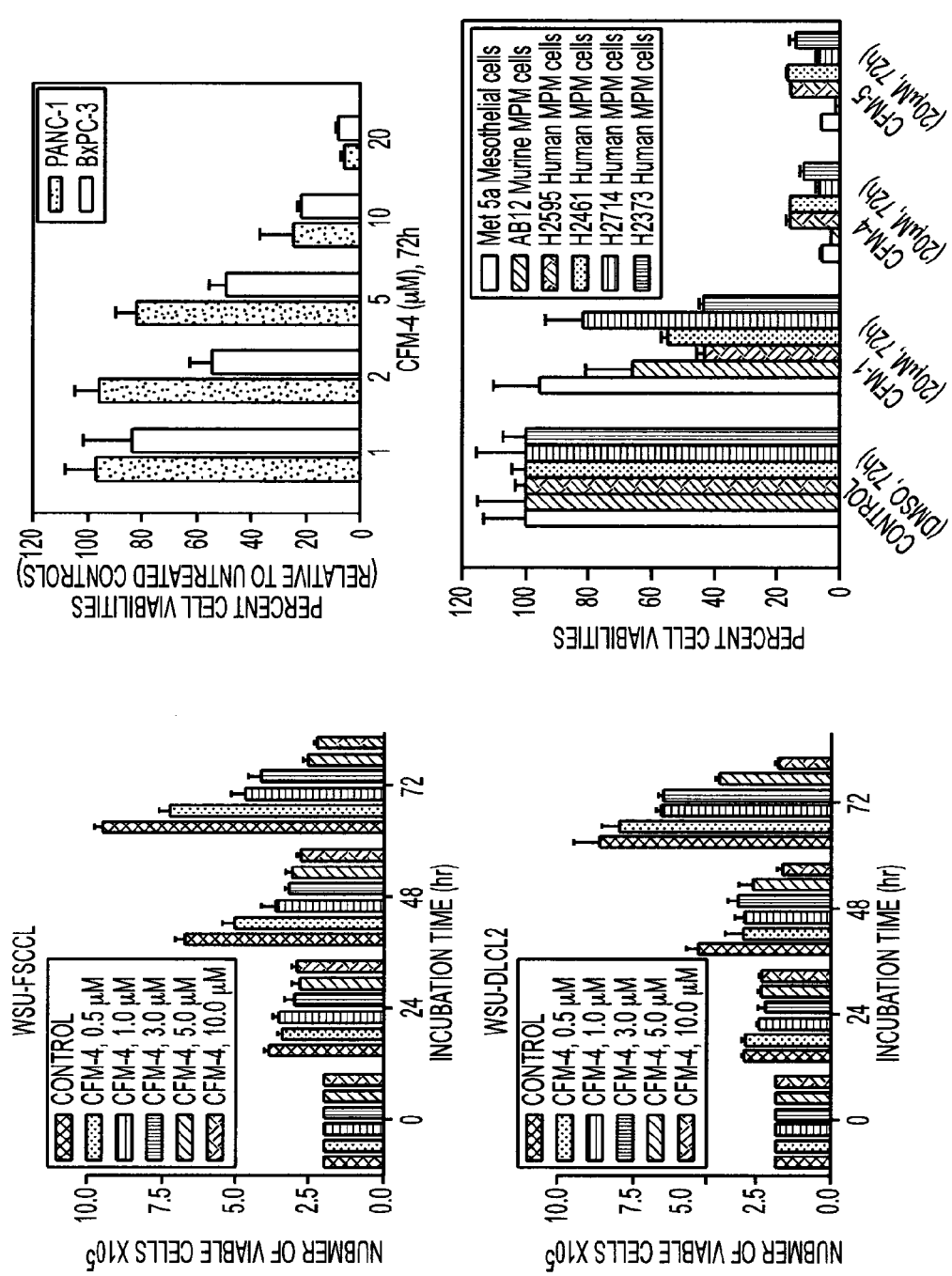
FIG. 12: CFMs inhibit growth of pancreatic cancer, lymphoma and MPM cells. Cell viability was determined by MTT assay following treatments of cells with vehicle/DMSO (Control) or indicated time and doses of CFMs. The columns in each histogram indicate live/viable cells and represent means of two-four independent experiments; bars, S.E.
Figures 13A, 13B, 13C:
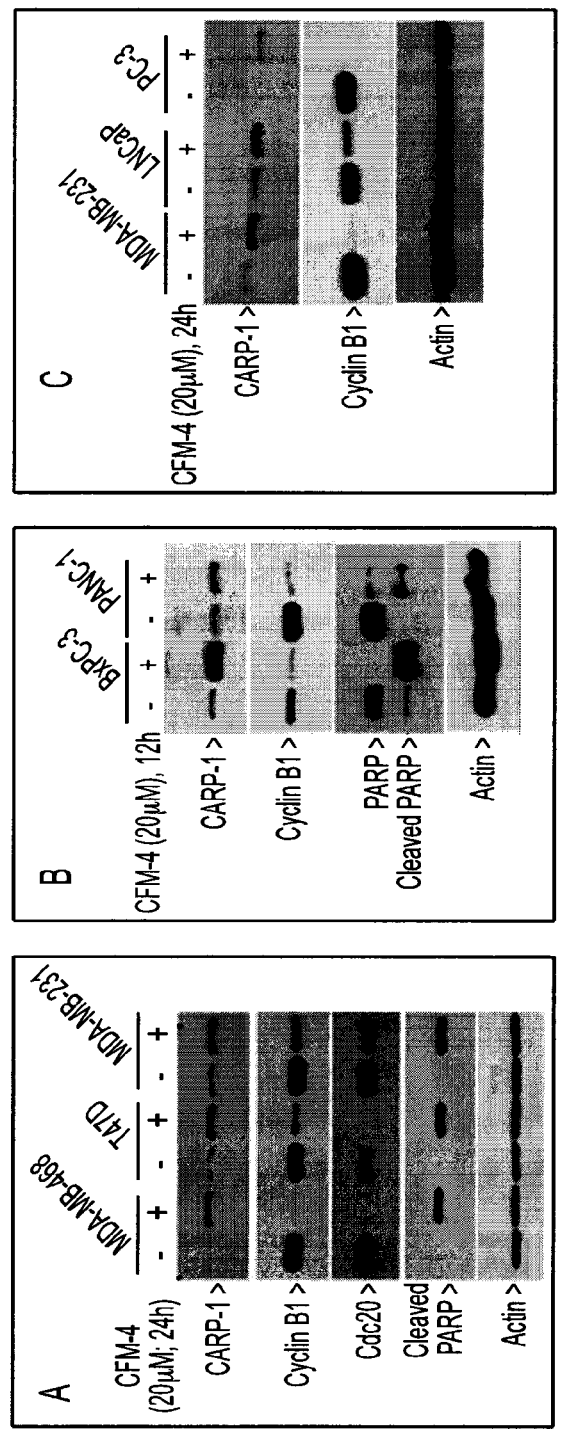
FIGS. 13A-13F: CFM-4 stimulates apoptosis, induces CARP-1 levels, causes cleavage of PARP, and depletion of cyclin B1 and Cdc20. A, B, C, Cells were treated with vehicle (DMSO, −) or with CFM-4 (+) for noted time and dose. The 50 μg of respective cell lysates were analyzed by WB essentially as in FIG. 5B for levels of various proteins that are indicated on the left side of the respective blots. D, cells were either untreated (Control), or treated for 24 h with 10 μg/ml ADR or 20 μM of indicated CFM. Staining of the cells was performed using terminal deoxynucleotidyl transferase-mediated nick end labeling (TUNEL) assay as detailed in methods. E, F, Blockage of caspases but not UPP interferes with cell growth suppression by CFM-4. Cell viability was determined by MTT assay following treatments of cells with vehicle/DMSO (Control), indicated time and doses of CFM-4 alone or in combination with noted time and doses of UPP or caspase inhibitors. The columns in each histogram indicate live/viable cells and represent means of two independent experiments; bars, S.E.
Figures 13D, 13E, 13F:
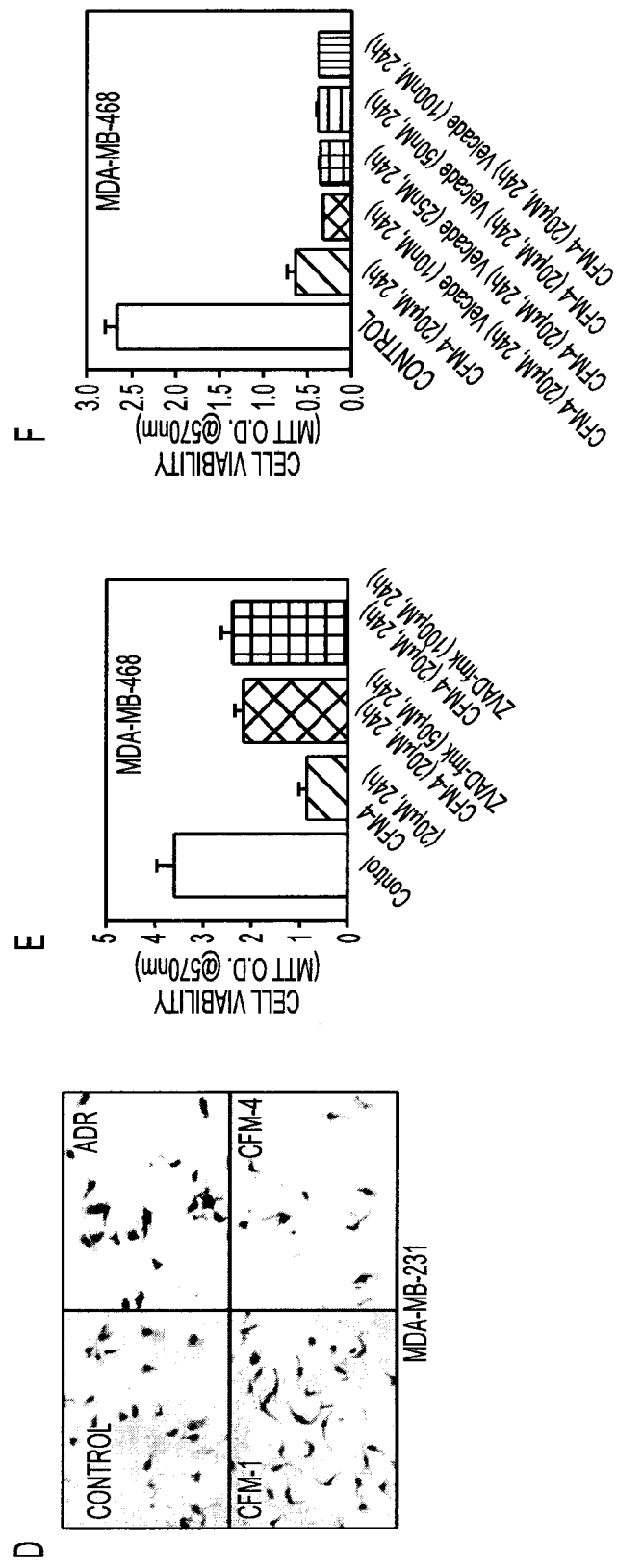
Figure 15A:
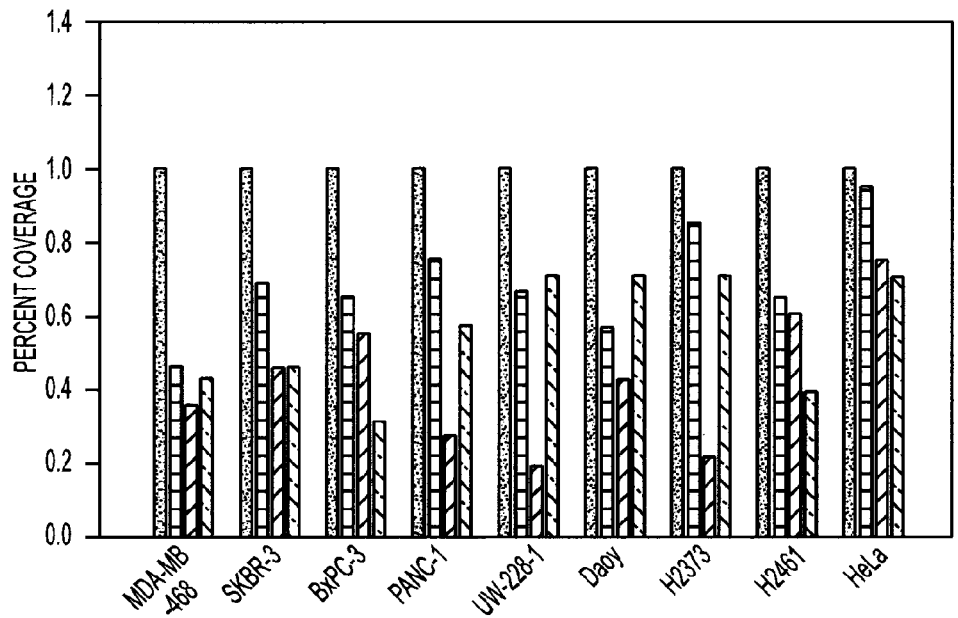
FIGS. 15A and 15B: CFMs inhibit Cancer Cell Growth in Soft Agar. The cancer cells were separately sandwiched between 0.6% and 0.3% agarose in DMEM medium containing FBS as noted in methods. The cells were either untreated (Control) or treated with 10 µM dose of CFMs as noted. Two cell lines each from breast cancer (MDA-MB-468 and SKBR-3), pancreatic cancer (PANC-1 and BxPC-3), Medulloblastomas (Daoy and UW-228-1), and Mesotheliomas (H2373 and H2461), and a cervical cancer cell line (HeLa) were subjected to the soft-agar assays. The colonies of cells were photographed as described in methods. A, B, Colonies from multiple, independent fields from each of the cell line were counted. Histograms represent average counts of colonies from control (untreated) and CFM-treated cells. Compounds for FIG. 15A; left to right for each cell line (control, CFM-1, CFM-4 and CFM-5). Compounds for FIG. 15B; left to right for each cell line (control, CFM-1, CFM-4, CFM-5, 12 and 2).
Figure 15B:
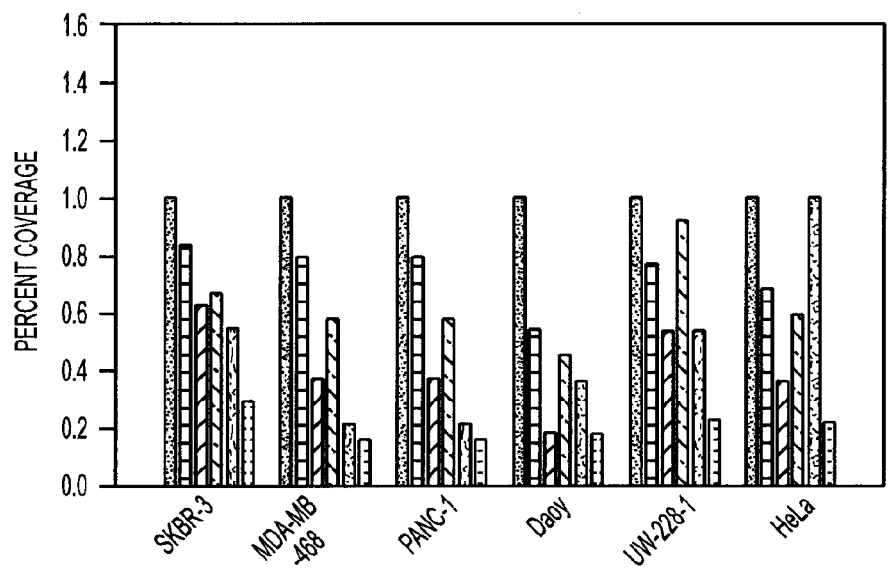
Figure 16A:
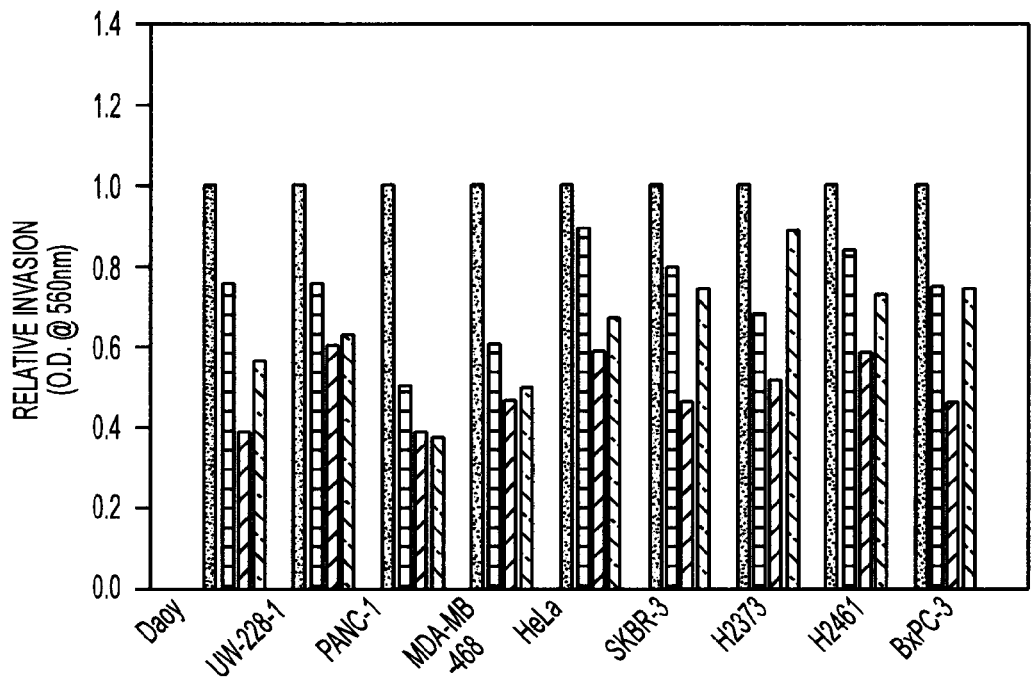
FIGS. 16A and 16B: CFMs attenuate Cancer Cell Invasion. The cancer cells were separately seeded in chambers with matrigel-coated membranes, and treated with buffer (Control) or with 10 µM dose of CFMs as noted in methods. Two cell lines each from breast cancer (MDA-MB-468 and SKBR-3), pancreatic cancer (PANC-1 and BxPC-3), Medulloblastomas (Daoy and UW-228-1), and Mesotheliomas (H2373 and H2461), and a cervical cancer cell line (HeLa) were subjected to the invasion assays. A, B, Cells were treated as above, and live cells migrating across the matrigel-coated membranes were dissociated, and quantitated by an MTT-based assay. The columns in histogram represent MTT OD of the CFM-treated cells relative to untreated controls. Compounds for FIG. 16A; left to right for each cell line (control, CFM-1, CFM-4 and CFM-5). Compounds for FIG. 16B; left to right for each cell line (control, 12 and 2).
Figure 16B:
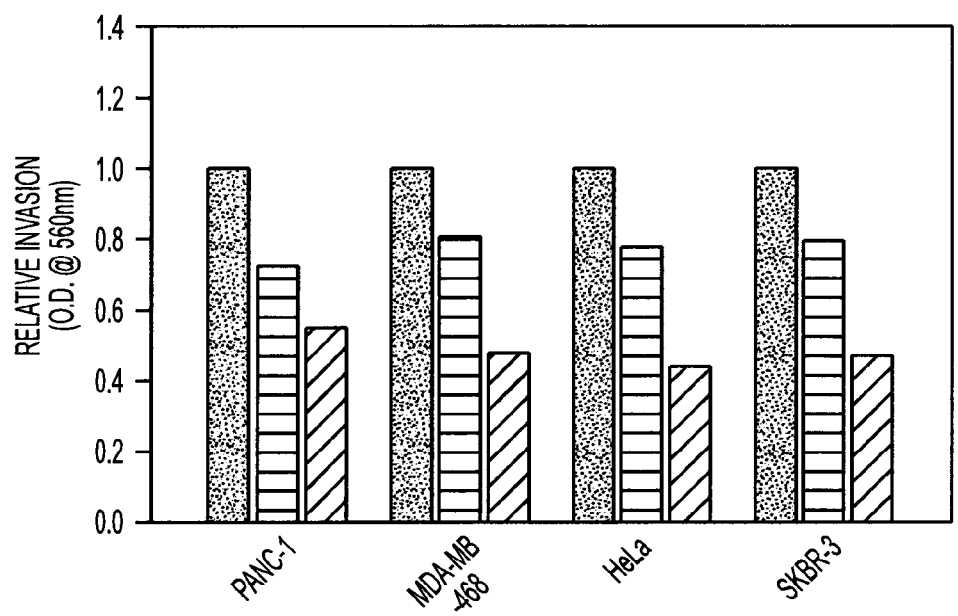

To test whether CFMs that interfere with CARP-1 binding with APC-2 modulate cell growth, HBC, colon, prostate, pancreatic cancer, MPM and lymphoma cells, as well as the immortalized, mammary epithelial MCF-10A cells were utilized. The cells were either treated with vehicle (DMSO) or various doses of the respective compound for a period of 72 h, and percent of live/viable cells for each compound was determined relative to the untreated controls as described in Methods. As shown in FIG. 3 and FIG. 12 each of the SMI suppressed cell growth in a dose-dependent manner with the exception of CFM-1 that elicited activity towards select MPM cells. Of note is the fact that although all the compounds inhibited HBC cell growth, the cells displayed relative increased sensitivity to the 20 μM dose of CFM-4 when compared with the similar dose of CFM-1 and 5. This is also consistent with the IC50 values of these SMIs in the in vitro binding FPAs where CFM-4 displayed an IC50 of 0.75 μM when compared with the IC50 values of 4.1 μM and 1.4 μM for CFM-1 and CFM-5, respectively. Although CFM-4 inhibited proliferation of a variety of cells including the drug (ADR or TAM)-resistant MCF-7 HBC cells, it failed to attenuate growth of the immortalized, non-tumorigenic MCF-10A cells (FIG. 3) suggesting that CFM-4 is selective in targeting cancer cells and therefore may have a suitable safety profile with low toxicities.

Figures 4A, 4B:
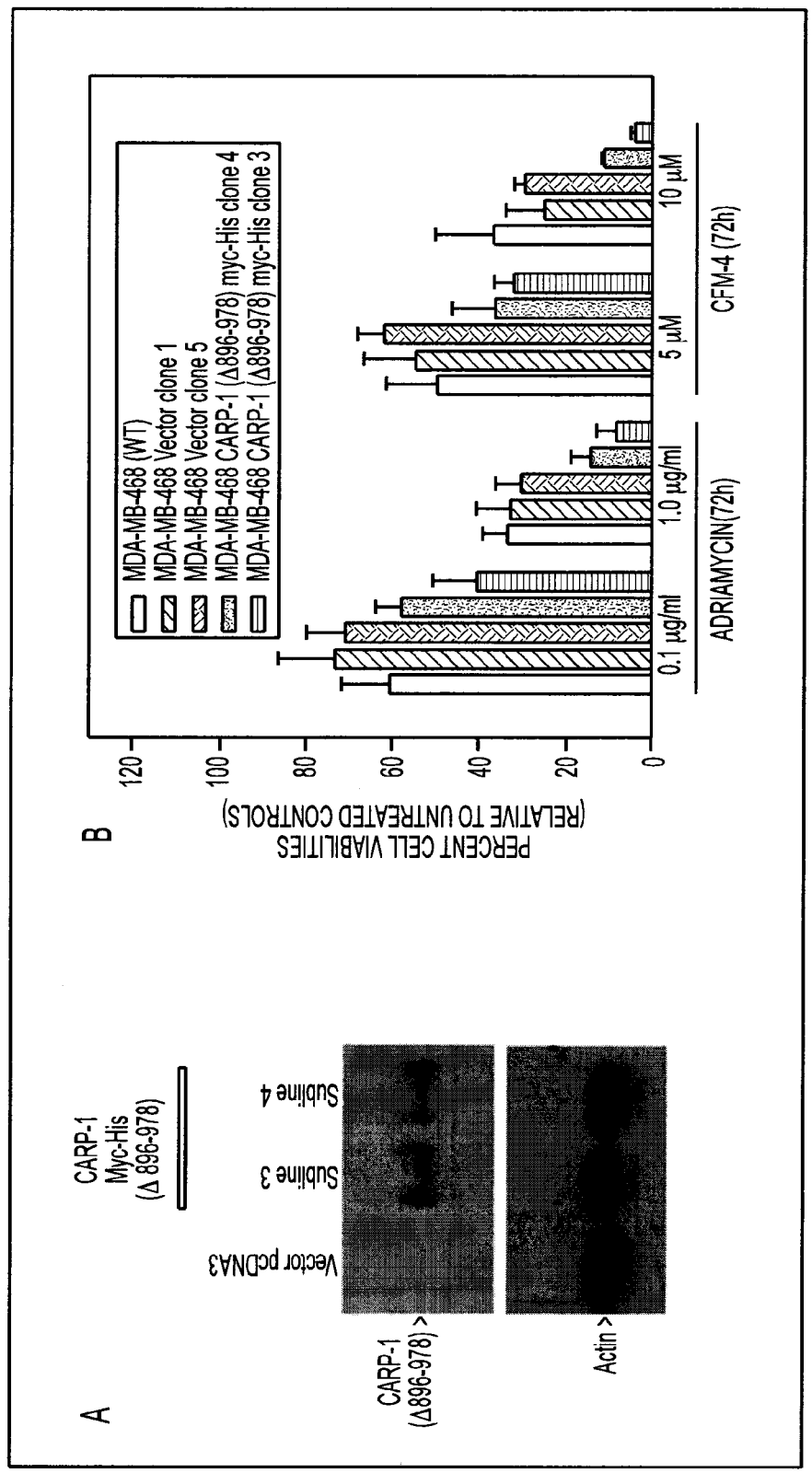
FIGS. 4A and 4B: CARP-1 binding with APC-2 regulates cell growth by ADR or CFM-4. (4A) Cell lysates (50 µg/lane) from each of the stable, neomycin-resistant sublines expressing vector or CARP-1 ($\Delta$896-978) were analyzed by WB for levels of CARP-1 ($\Delta$896-978) and actin proteins by utilizing anti-myc-tag and actin antibodies, respectively, as described in methods. (4B) Cells were treated with indicated doses of CFM-4 or ADR for noted times, and were subjected to MTT assay for determination of their viabilities as in FIG. 3. Columns represent means of three independent experiments; bars, S.E.

The extent CARP-1 binding with APC-2 regulates cell growth was investigated next by utilizing stable HBC sublines expressing vector or the CARP-1 (Δ896-978)-myc-His (FIG. 4A). Cells were either treated with vehicle (DMSO), 0.1 and 1.0 μg/ml ADR, or 5 and 10 μM doses of CFM-4, followed by determination of viable/live cells as above. Both the agents suppressed growth of the wild-type as well as the vector and CARP-1 (Δ896-978) expressing cells (FIG. 4B). Interestingly, cells expressing CARP-1 (Δ896-978) were generally more sensitive to inhibition by both the agents. In particular treatment with 10 μM dose of CFM-4 resulted in a greater loss of viability of CARP-1 (Δ896-978) cells when compared with their similarly treated wild-type or vector-transfected counterparts. Since APC/C E3 ubiquitin ligase is well known to target UPP-dependent degradation of many cellular proteins, it is possible that CARP-1 is also a substrate of APC/C. If so, the absence of the APC-2-binding epitope in CARP-1 (Δ896-978) would likely prevent its degradation by APC/C and sensitize the cells to the inhibitory effects of agents that function in part by elevating cellular CARP-1 levels. Although it remains to be clarified whether CARP-1 is a substrate for APC/C E3 ubiquitin ligase, blockage of UPP has previously been found to elicit CARP-1 increase, and apoptosis-promoting signaling by ADR and CFM-4 (see below) nonetheless enhance CARP-1 levels.

Figures 5A, 5B:
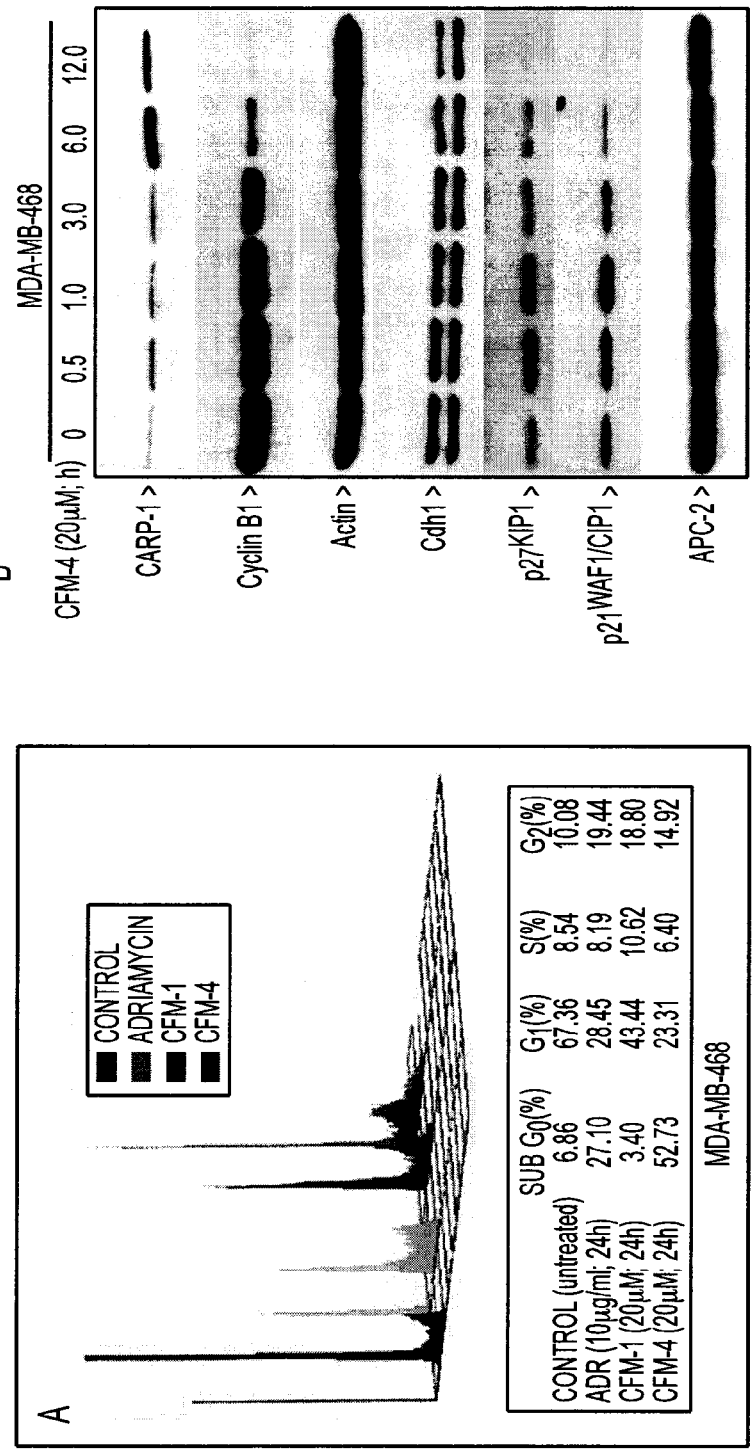
FIGS. 5A-5D: CFM-4 suppresses cell growth in part by elevating CARP-1 and diminishing cyclin B1 levels. In panel A, cells were treated with indicated agents for noted times, labeled with propidium iodide, and sorted by flow cytometry. Histogram and table below represent cell numbers in various phases of cell cycle. In panel B, cells were treated with indicated dose of CFM-4 for noted times, in panel C, cells were either untreated (−) or treated (+) with CFM-4 for noted dose and time, while in panel D, cells were either treated with vehicle control (DMSO) or with indicated agents for noted dose and time. The cell lysates (50 µg/lane) in panels B-D were analyzed by WB for levels of CARP-1, Cyclin B1, Cdh1, APC-2, CDKIs $p21^{WAF1/CIP1}$, $p27^{KIP1}$ and actin proteins as in methods.
Figures 5C, 5D:
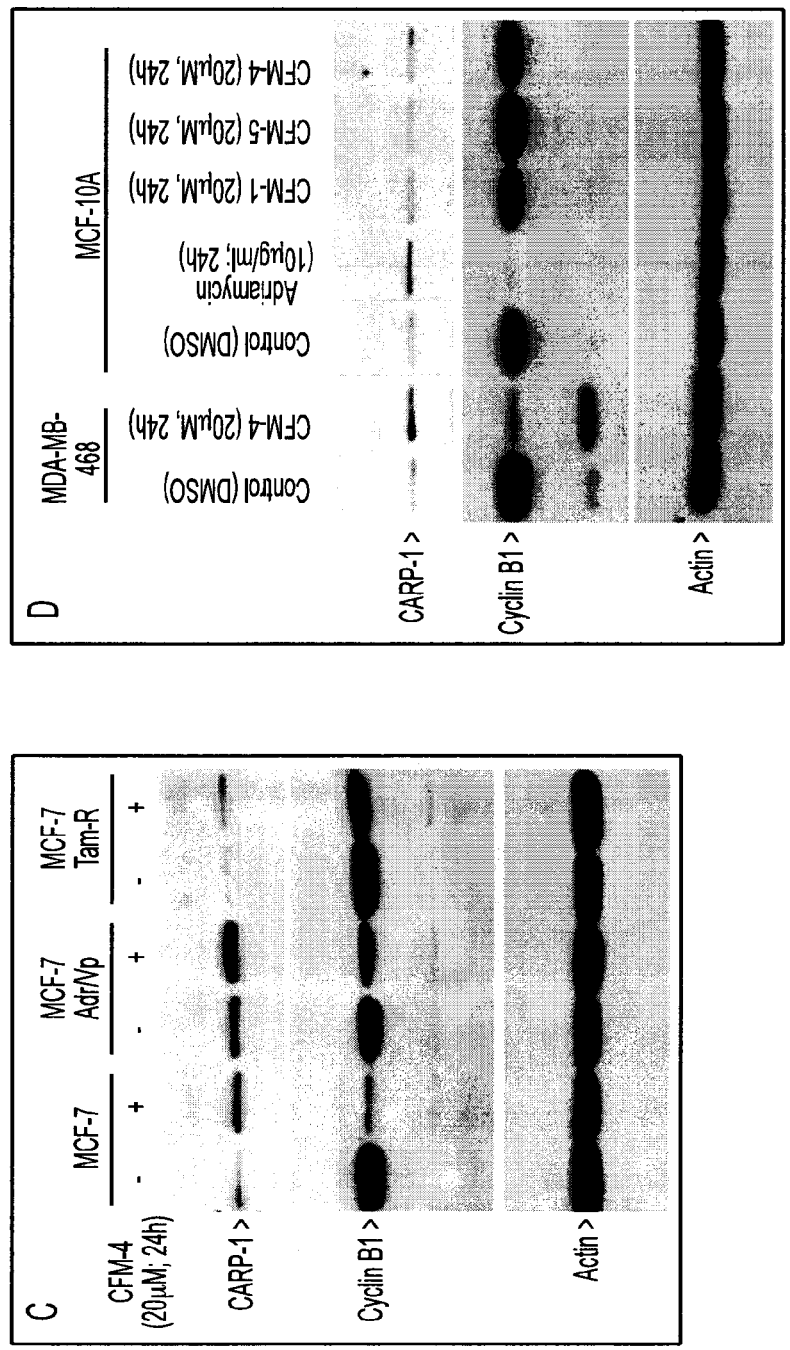

CARP-1 is required for CFM-4-dependent cell growth inhibition. Because APC/C E3 ubiquitin ligase functions to regulate cell cycle and CFM-4 binds with CARP-1 to inhibit its binding with APC-2, it was next determined whether the SMIs interfere with cell cycle progression. Flow-cytometric analysis revealed that like ADR, CFM-1 or CFM-4 treatments induced G2M cell cycle arrest (FIG. 5A). The APC/$C^{Cdc20}$ E3 ubiquitin ligase regulates turnover of the mitotic cyclin B1 and Cdc20 during the G2M phase and exit to mitosis while APC/$C^{Cdh1}$ E3 ligase targets Cdc20 as well as SCF ligase to accomplish exit from mitosis and transition to G0/G1 phases. Attenuation of SCF ligase by APC/$C^{Cdh1}$, in turn, results in elevated levels of CDKIs $p21^{WAF1/CIP1}$ and $p27^{KIP1}$. ADR on the other hand has been shown to promote mitotic crisis in part by stimulating caspase-6-dependent premature degradation of cyclin B1. Since CARP-1 has previously been found to negatively regulate cyclin B1 levels and Velcade (UPP inhibitor) exposure caused elevated CARP-1, it was possible that prevention of CARP-1 binding with APC-2 in the presence of CFM-4 resulted in elevated CARP-1. To investigate this possibility it was determined whether CFM-4 binding with CARP-1 modulated CARP-1 levels. It was found that exposure to CFM-4 stimulated CARP-1 levels but depleted cyclin B1 at 6 h and subsequent treatment periods (FIG. 5B). Although levels of APC-2 were unaffected, CFM-4 exposure resulted in a modest decline in Cdh1 levels (FIG. 5B) while Cdc20 levels were significantly reduced (see below). Interestingly, CFM-4 treatments modulated CDKI levels in a biphasic manner. Levels of both the $p21^{WAF1/CIP1}$ and $p27^{KIP1}$ CDKIs were elevated when cells were exposed to CFM-4 for 0.5-1.0 h time periods (FIG. 5B). This may likely be due to the initial response of the cells to stress following exposure to CFM-4. Presence of CFM-4 for periods of 3 h and beyond resulted in decline in the levels of both the CDKIs. This loss of CDKI expression could be due to attenuation of APC/$C^{Cdh1}$ activity following modest reduction in the Cdh1 levels as well as inability of CARP-1 to bind with APC-2 over prolonged periods of treatments with CFM-4. CFM-4 treatments also resulted in elevated CARP-1 and reduced cyclin B1 levels in drug (ADR or TAM)-resistant MCF-7 cells (FIG. 5C) but not in MCF-10A cells (FIG. 5D). Thus, co-incident increase of CARP-1 and loss of cyclin B1 in the presence of CFM-4 is consistent with previously noted negative regulation of cyclin B1 following elevated expression of CARP-1.

Figures 6A, 6B, 6C, 6D:
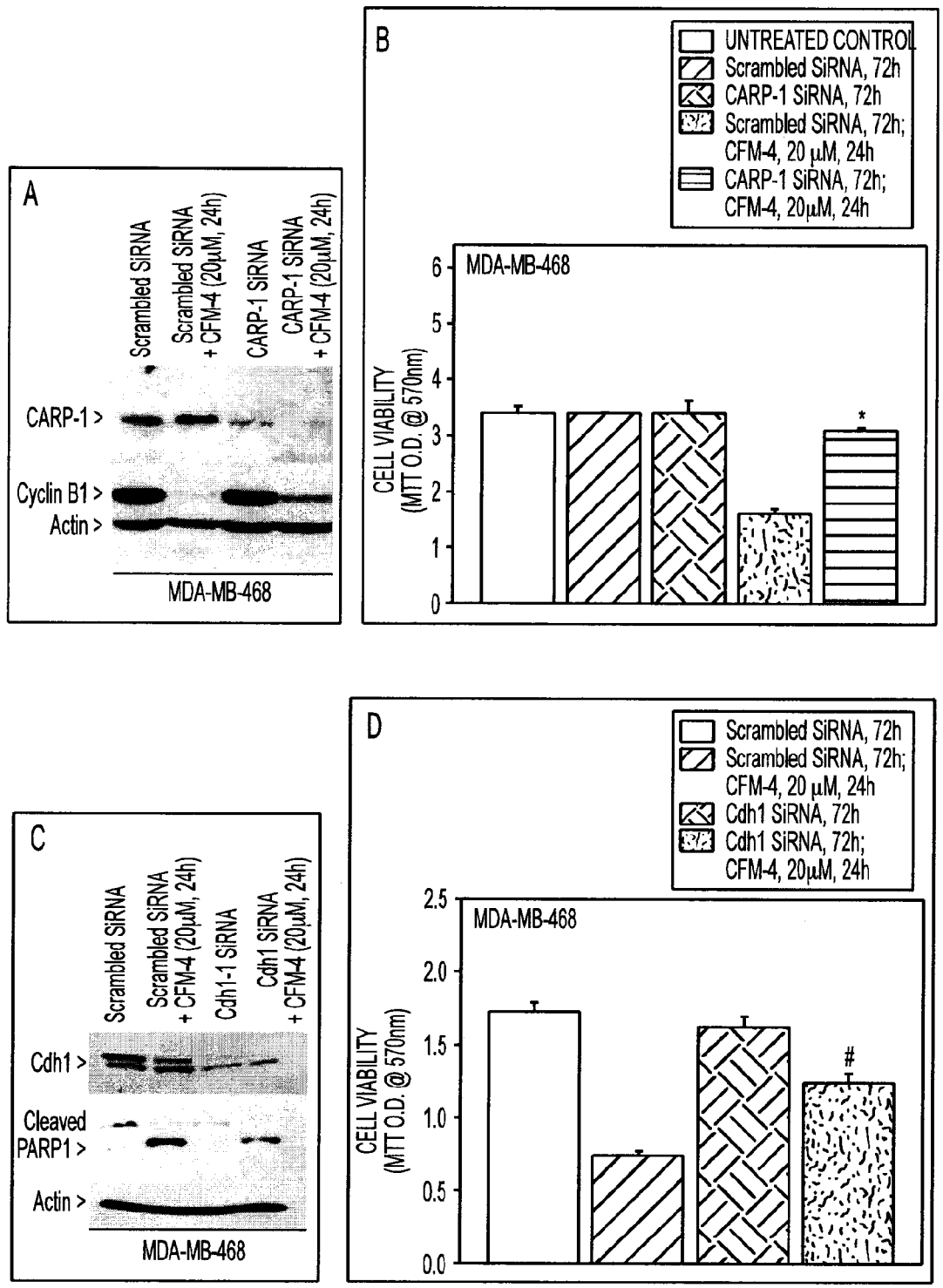
FIGS. 6A-6E: CARP-1 is required for cell growth inhibition by CFM-4, and cyclin B1 loss in the presence of CFM-4 is accomplished independent of UPP. Knockdown of CARP-1 (A, B) or Cdh1 (C, D) blocks CFM-4 effects. Cells were transfected with scrambled, CARP-1 SiRNAs (panel A), or Cdh1 SiRNAs (panel C) for 72 hours, and were then either untreated or treated with CFM-4 for noted time and dose. Cell lysates were subjected to WB as in FIG. 5B above. In panels B and D, cells were similarly transfected with SiRNAs and treated as in A and C, and subjected to MTT assay for determination of their viabilities. Columns represent means of three independent experiments; bars, S.E. * and #, p=<0.01 relative to CFM-4-treated, scrambled SiRNA-transfected cells (E) CFM-4 targets cyclin B1 independent of UPP. The cells were either treated with DMSO (control) or with noted dose and time of indicated agents. Cell lysates were then analyzed by WB as in A above for levels of various proteins that are indicated on the left side of each blot of the panel.

The in vitro binding experiments in FIG. 2 indicate that CFM-4 and 5 bind with CARP-1, and together with the data demonstrating cell growth suppression by these SMIs, suggests that CARP-1 is required for their growth inhibitory function. To test this possibility, cells were transfected with 100 nM each of the CARP-1 or the scrambled SiRNAs as detailed in methods. The SiRNA-transfected cells were then either untreated or treated with 20 μM CFM-4 for 24 h followed by determination of levels of CARP-1 and cyclin B1 proteins. As shown in FIG. 6A, CARP-1 SiRNA caused significantly reduced levels of CARP-1 when compared with CARP-1 levels in the cells transfected with scrambled SiRNAs. CFM-4 treatment stimulated CARP-1 expression in cells transfected with scrambled SiRNAs but not in the CARP-1 SiRNA-transfected cells. CFM-4 treatments also resulted in a greater reduction of cyclin B1 levels in the cells transfected with the scrambled SiRNAs, while knockdown of CARP-1 interfered with loss of cyclin B1 after treatment with CFM-4. These data suggest that CFM-4 presence results in increased CARP-1 and diminished cyclin B1 proteins, while loss of CARP-1 interferes with CFM-4-dependent expression of these proteins. In a separate experiment, cells were similarly transfected with CARP-1 SiRNA or scrambled SiRNAs followed by treatment with CFM-4 essentially as in FIG. 6A, and cell viabilities were determined by the MTT assay. As shown in FIG. 6B, CFM-4 suppressed growth of the cells transfected with scrambled SiRNAs, while CARP-1 knockdown blocked CFM-4-dependent inhibition of cell growth. These data suggest that CARP-1 expression is necessary for CFM-4 inhibition of cell growth, and that this SMI functions in part by inducing CARP-1 levels while attenuating cyclin B1 expression. CFM-4 also induced cyclin B1 loss in prostate and pancreatic cancer cells (FIG. 13A-13F) and together with data in FIG. 5 underscore cyclin B1 targeting as an important mechanism of cell growth suppression by this SMI. Since, CFM-4 functions in part by modulating APC/$C^{Cdh1}$ activity as demonstrated by loss of CDKIs in FIG. 5B, it was next examined whether depletion of individual APC/C components such as APC-2, Cdc20, or Cdh1 will interfere with CFM-4 effects. Since CFM-4 failed to alter APC-2 levels, it was first examined whether SiRNA-mediated depletion of APC-2 will interfere with CFM-4 effects. Transfection of HBC cells with APC-2 SiRNAs resulted in a 2-3-fold reduction in APC-2 levels over a period of 72-96 h (not shown). Depletion of APC-2 intriguingly attenuated cell growth (not shown). SiRNA-mediated depletion of Cdc20 also attenuated cell growth and was consistent with previous study that demonstrated blockage of mitotic exit and induction of apoptosis following knockdown of Cdc20. It was therefore decided to target Cdh1 in HBC cells to determine whether and to what extent depletion of Cdh1 will prevent cell growth inhibition by CFM-4. As shown in FIG. 6C, Cdh1 SiRNA caused significantly reduced levels of Cdh1 when compared with Cdh1 levels in the cells transfected with scrambled SiRNAs. CFM-4 treatment also caused modest decline in Cdh1 expression in cells transfected with scrambled SiRNAs that is consistent with our data in FIG. 5B. CFM-4 treatment however stimulated robust cleavage of PARP1 in cells transfected with scrambled SiRNAs, while knockdown of Cdh1 diminished cleavage of PARP1 in CFM-4-treated cells. In a separate experiment, cells were similarly transfected with Cdh1 SiRNA or scrambled SiRNAs followed by treatment with CFM-4 essentially as in FIG. 6C, and cell viabilities were determined by the MTT assay. As shown in FIG. 6D, CFM-4 suppressed growth of the cells transfected with scrambled SiRNAs while Cdh1 knockdown blocked CFM-4-dependent inhibition of HBC cell growth.

Figure 6E:
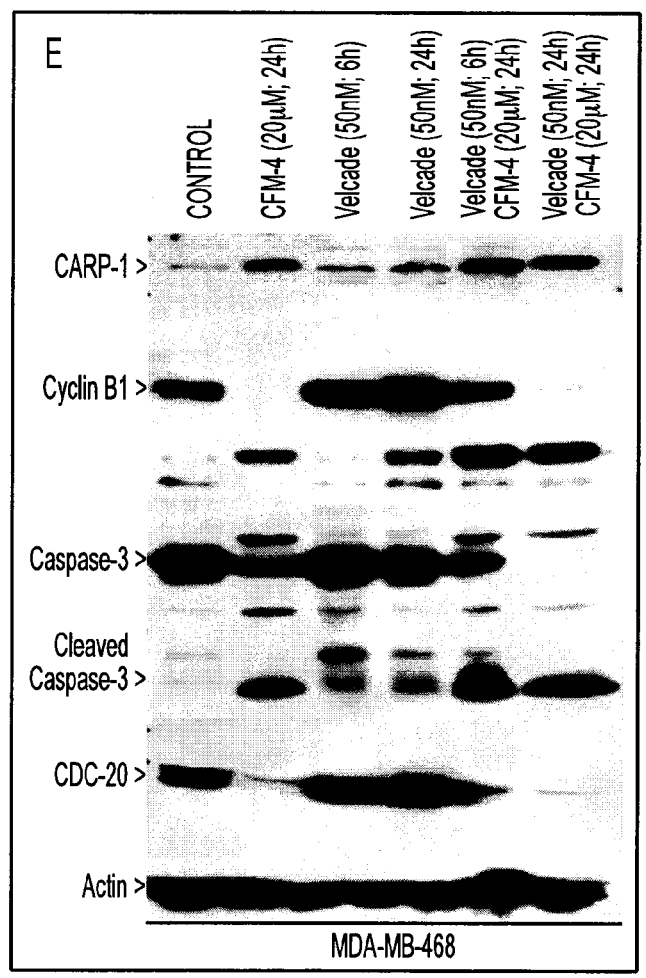

In light of the fact that the UPP is known to target cyclin B1 and Cdc20 during G2M phase and exit of cells from mitosis, the extent to which the UPP was involved in CFM-4-dependent loss of cyclin B1 and Cdc20 was examined. For this purpose, cells were treated with 50 nM velcade for 6 h or 24 h, 20 µM CFM-4 for 24 h, or a combination of both, and the cell lysates were analyzed for expression of CARP-1, cyclin B1, Cdc20 and activated Caspase 3. CFM-4 caused a robust increase in CARP-1 levels while treatment with velcade resulted in a modest increase in CARP-1 levels. Velcade-dependent increase in CARP-1 levels is consistent with earlier observations in breast cancer and MPM cells. Presence of velcade however failed to interfere with CFM-4-dependent loss of cyclin B1 or Cdc20 proteins (FIG. 6E). Thus although CFM-4 functions in part by antagonizing CARP-1 binding with the APC/C, depletion of cyclin B1 and Cdc20 proteins in the presence of this agent is likely independent of the UPP.

Figures 7A, 7B, 7C, 7D:
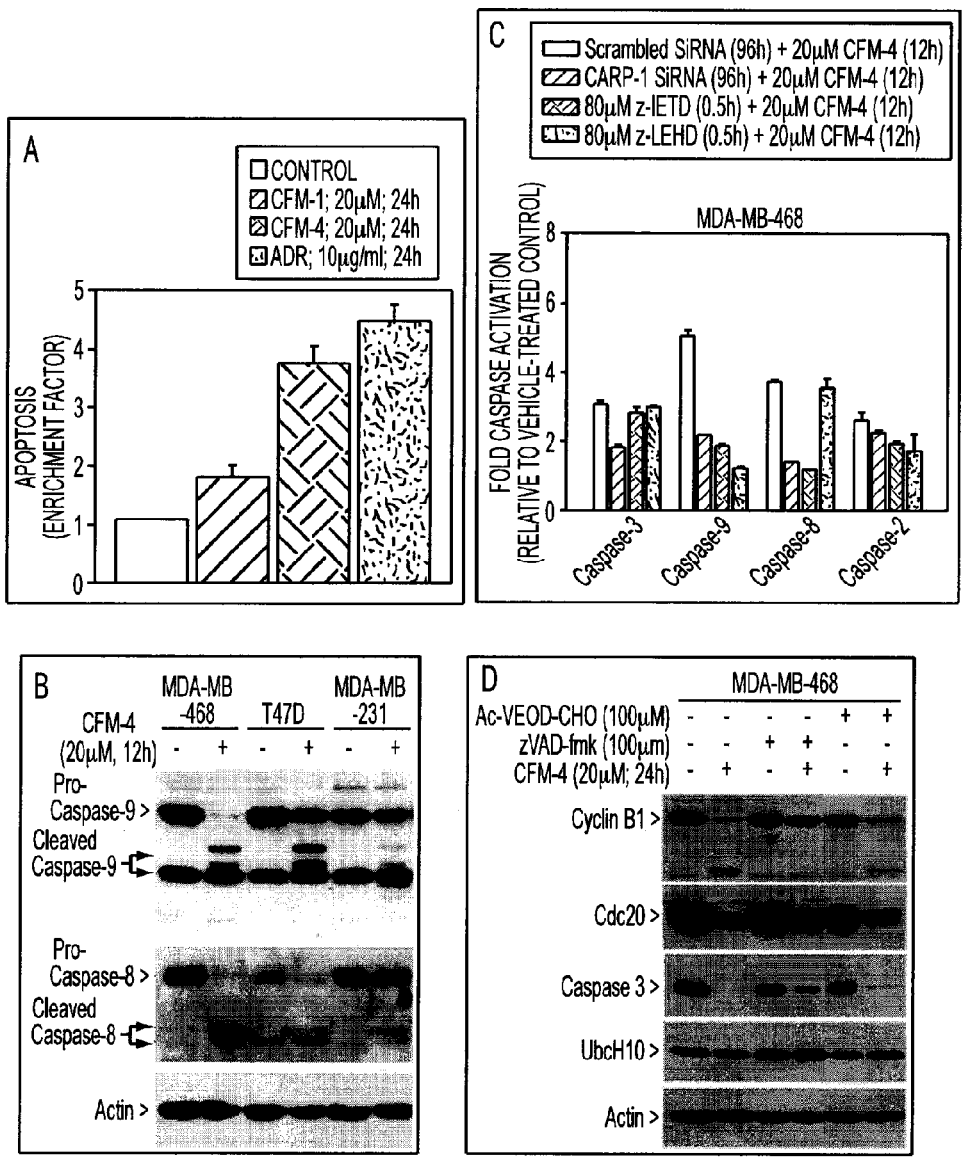
FIGS. 7A-7D: CFM-4 suppresses cell growth in part by inducing apoptosis that involves caspase-dependent targeting of cyclin B1 and Cdc20 proteins. (A) Cells were either treated with DMSO (control) or with indicated agents for noted times, and the cell lysates subjected to measurement of DNA fragmentation by ELISA-based assay. Columns represent means of three independent experiments; bars, S.E. (B) Cells were either untreated (−) or treated (+) with CFM-4 for noted dose and time. Cell lysates were then analyzed by WB as in FIG. 5B above for levels of pro and activated caspases 9 and 8, and actin proteins that are indicated on the left side of each blot of the panel. (C) Cells were either transfected with scrambled SiRNA, CARP-1 SiRNA, treated with caspase-8 inhibitor, or caspase-9 inhibitor prior to treatments with CFM-4 as indicated. Activities of the noted caspases were profiled as in methods. Columns in histogram represent fold activities of caspases relative to the corresponding controls and are derived from means of two independent experiments; bars, S.E. (D) CFM-4 inhibition of cyclin B1 and Cdc20 levels is dependent on caspase activation. Cells were treated with vehicle (DMSO, −), CFM-4 (+), caspase inhibitor, or a combination of both for noted time and dose. Cell lysates were then analyzed by WB as in FIG. 5B above for levels of various proteins that are indicated on the left side of each blot of the panel.

CFM-4 suppresses cell growth in part by inducing apoptosis: In light of the data in FIG. 5A showing significant accumulation of CFM-4-treated cells in the sub $G_0$ phase, and the fact that cells undergoing apoptosis often accumulate in the sub $G_0$ fractions, it was next ascertained the extent of apoptosis stimulation by these agents by utilizing an ELISA-based DNA fragmentation assay. The data revealed significantly elevated levels of apoptosis in the cells that were treated with CFM-4 or ADR (FIG. 7A). It is of note that while both CFM-1 and CFM-4 suppressed viabilities of HBC cells (FIG. 3), only treatments with CFM-4 induced apoptosis (FIG. 7A). The intrinsic, mitochondria-mediated and the extrinsic, extracellular receptor-activated, apoptosis signaling pathways are transduced by activation of various caspases that promote eventual breakdown of cellular proteins, organelles and plasma membrane. Caspase 8 is often activated by extrinsic signals while intrinsic apoptosis target mitochondria leading to activation of caspase 9. It was next determined whether apoptosis stimulation by CFM-4 involved activation of caspases 8 or 9 or both. WB analysis of cell lysates derived from CFM-4-treated cells revealed cleavage of caspases 9 and 8 (FIG. 7B), suggesting that this SMI likely functions by activating both extrinsic and intrinsic apoptosis signaling pathways. The activation of caspases in the presence of CFM-4 was further profiled by utilizing a fluorescence-based quantitative assay as detailed in methods. CFM-4 exposure caused activation of caspases 3, 8, 9, and 2 (FIG. 7C). Consistent with the requirement of CARP-1 in CFM-4-dependent cell growth inhibition, it was found that CARP-1 knock-down interfered with CFM-4-dependent activation of caspases, in particular caspases 3, 8, and 9 (FIG. 7C). Pre-treatment of cells with z-IETD-fmk or z-LEHD-fmk, the pharmacologic inhibitors of caspase 8 or caspase 9, respectively, abolished activation of these caspases by CFM-4. Presence of caspase 8 inhibitor also attenuated CFM-4-dependent activation of caspases 9. Blockage of caspase 9, on the other hand, did not affect activation of caspase 8 by CFM-4 (FIG. 7C). These data suggest that CFM-4 activates caspase 8 prior to activating caspase 9. Additional WB analysis revealed elevated levels of CARP-1, cleavage of caspase-target PARP, and loss of cyclin B1 and Cdc20 proteins in CFM-4-treated cancer cells (FIGS. 13A-13F).

The extent CFM-4 signaling required activities of caspases to regulate levels of cyclin B1 and Cdc20 proteins was also examined. Cells were pre-treated with a pharmacologic pan-caspase inhibitor zVAD-fMK or a specific, caspase-6 inhibitor Ac-VEOD-CHO followed by their exposure to CFM-4. WB analysis of the cell lysates derived from the untreated and treated cells revealed pre-treatment of cells with the pan-caspase or caspase-6 inhibitors blocked CFM-4-dependent loss of cyclin B1 and Cdc20 proteins (FIG. 7D). The levels of E2 ubiquitin ligase UbCH10 however were not affected in the cells that were treated either with CFM-4 alone or in combination with caspase inhibitors. Presence of zVAD-fMK also blocked the ability of CFM-4 to suppress cell growth (supplementary FIG. 4E). These data suggest that CFM-4 inhibits cell growth in part by caspase-dependent targeting key cell cycle regulatory proteins to promote G2M arrest. Thus data in FIGS. 6 and 7 collectively demonstrate that cell growth inhibitory signaling by CFM-4 targets cyclin B1 and Cdc20 proteins in a manner that is independent of the UPP while requiring activation of initiator caspases 8 and 9.

Figures 8A, 8B, 8C:
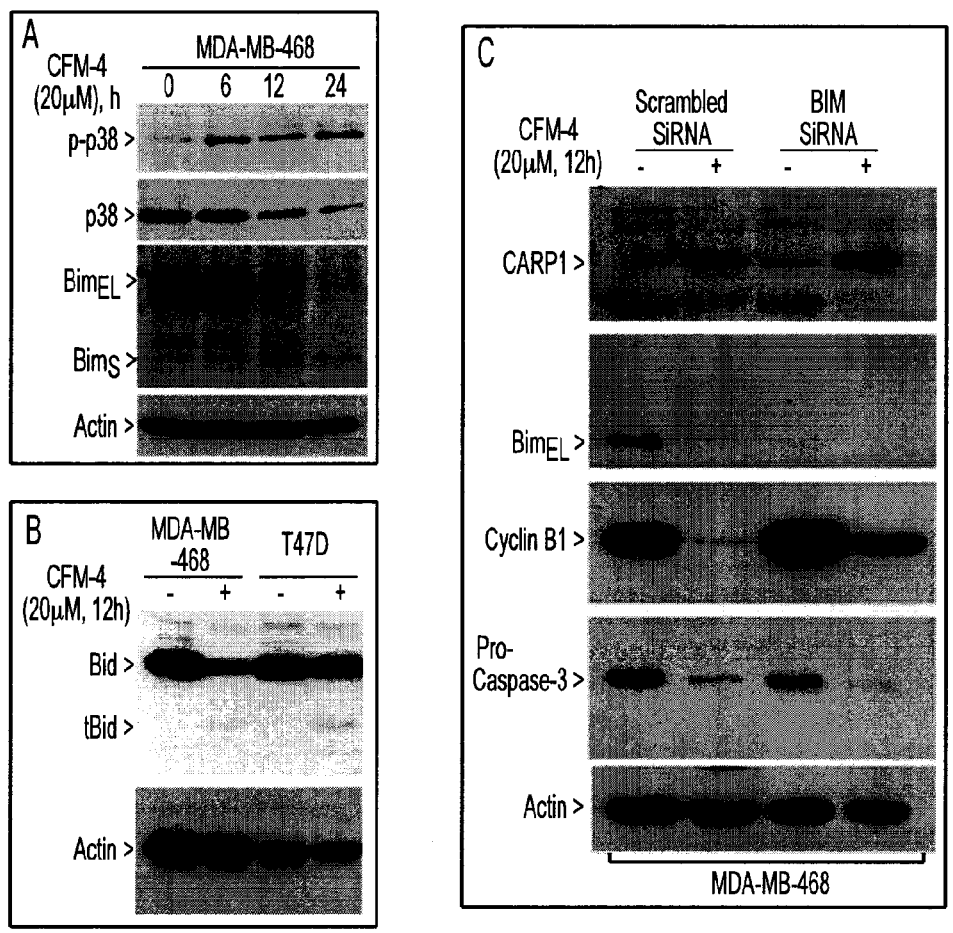
FIGS. 8A-8C: CFM-4 exposure results in activation of pro-apoptotic p38, Bim and Bid proteins, and loss of Bim blocks CFM-4-dependent depletion of cyclin B1. Cells were treated with DMSO (0 or −) or with CFM-4 (+) for noted time and dose except that in panel C cells were transfected with indicated SiRNAs for 96 h followed by their treatments with DMSO (−) or CFM-4 (+). At the end of treatment periods, 50 gig of each lysate was analyzed by WB essentially as in FIG. 5B. The presence of different proteins on the radiogram is indicated by arrows on left side of each panel.
Figure 9:
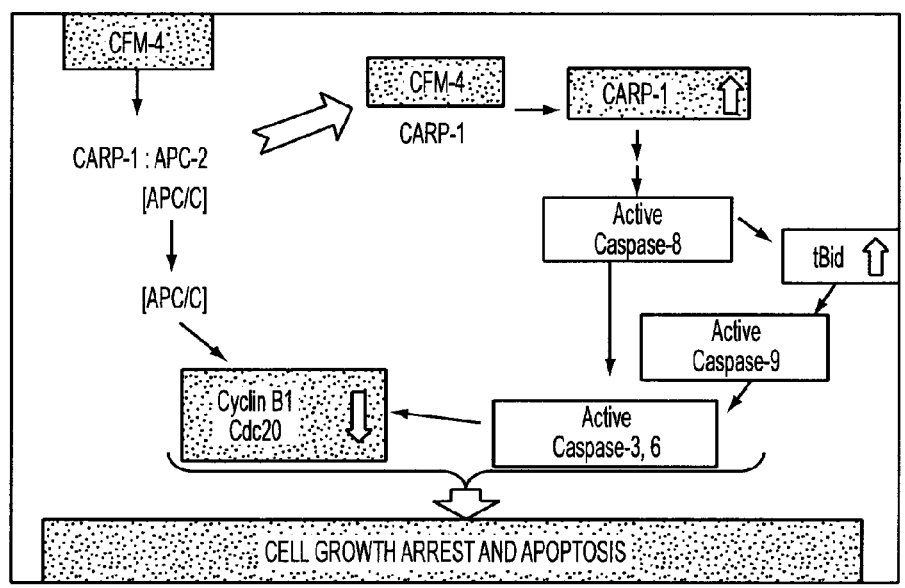
FIG. 9: Schematic of mechanism of action of CFM-4.

Previous studies have indicated involvement of p38 MAPK/SAPK and apoptosis signaling in transducing CARP-1-dependent growth inhibitory effects. Since CFM-4 elevated CARP-1 levels (FIGS. 5B, 5C, 6A and 6E), it was further investigated the extent CFM-4 treatments activated p38. As shown in FIG. 8A, treatment of cells with 20 µM CFM-4 resulted in activation (phosphorylation) of p38. Although, p38 activation occurred as early as 6 h and was sustained through 24 h, the levels of total p38 began to decline by 12 h of CFM-4 treatment possibly due to ensuing apoptotic cell death. It was further determined whether and to what extent any of the Bcl2 family of anti- and/or pro-apoptotic proteins was involved in transducing CFM-4-dependent apoptosis signaling. CFM-4 treatments failed to modulate levels of $Bcl_2$, $Bcl_{XL}$, Noxa, and Puma proteins in different cells (not shown). Levels of the pro-apoptotic protein Bim however were altered following exposure of cells to CFM-4 in a time-dependent manner. Specifically, levels of $Bim_{EL}$ declined significantly following 12 h or 24 h treatments; a concomitant increase in the levels of the pro-apoptotic, BH3-only, $Bim_s$ isoform was noted in CFM-4-treated cells (FIG. 8A). Emerging evidence indicates Bim is activated during chemotherapy (paclitaxel)-induced apoptosis, and targets all pro-survival, Bcl2-family of proteins at the mitochondrial membrane. Bim is also known to bind with Bax and promote Bax translocation to the mitochondria to induce cytochrome C release and subsequent activation of caspase-9 to trigger the intrinsic apoptosis cascade. Although, CFM-4 treatments failed to stimulate Bax expression (not shown), it is likely that activated $Bim_s$ targets pro-survival Bcl2 family proteins directly or functions to facilitate Bax translocation to mitochondria and consequent activation of caspases 9 and 3. Since blockage of caspase 8 interfered with activation of caspases 9 and 3 in the presence of CFM-4 (FIG. 7C), and the fact that activated caspase 8 is known to target pro-apoptotic protein Bid to facilitate generation of truncated Bid (tBid) to subsequently target mitochondria for activation of caspase 9, it was investigated whether CFM-4 exposure also promoted generation of tBid. As shown in FIG. 8B, exposure of cells to CFM-4 resulted in a modest increase in tBid levels suggesting that activation of caspase 9 by this compound is accomplished in part by the caspase 8 pathway. SiRNA-mediated depletion of Bim, on the other hand, prevented loss of cyclin B1 in the presence of CFM-4 while loss of Bim failed to interfere with CFM-4-dependent CARP-1 increase (FIG. 8C). Together data in FIGS. 6, 7 and 8 suggest that although CFM-4 elevates CARP-1 to enhance apoptosis, Bim expression and activation of caspases are required for targeting of cyclin B1. Thus SMIs such as CFM-4 that antagonize CARP-1 binding with APC-2 suppress cell growth in part by activating caspases to stimulate apoptosis as well as caspase-dependent targeting of cyclin B1 and Cdc20 proteins (FIG. 9).

Discussion

CARP-1 is a peri-nuclear phosphoprotein that is thought to have broad roles in apoptosis signaling and transcriptional regulation. A number of studies to-date indicate CARP-1 involvement in cell growth signaling by tumor suppressor p53, protein kinase A, the steroid/thyroid receptor superfamily, β-catenin, and DNA-damage inducing chemotherapeutics. Proteomic-based studies further revealed that CARP-1 interacts with the SAPK p38 and the NF-κB upstream kinase subunit NEMO/IKKγ. Together with the fact that retroviral or TAT-mediated expression of various non-overlapping peptides of CARP-1 suppressed growth of HBC and lymphoma cells in vitro and in vivo, it was speculated that CARP-1 likely functions in part by interacting with a number key cell growth and apoptosis transducers in a context and signal-dependent manner. To test this possibility, a Y2H screen using CARP-1 as a bait was performed and found that the carboxyl terminal region of CARP-1 binds with an epitope within the cullin-homology domain of the APC-2, a subunit of the APC/C E3 ubiquitin ligase. Following mapping of the respective epitopes involved in CARP-1-APC-2 binding, and determination of their binding kinetics ($K_d$) in vitro by an FPA, an additional screen of a chemical library was conducted which identified several SMIs of CARP-1-APC-2 binding. The lead compound CFM-4, antagonizes CARP-1 interaction with APC-2 by binding with CARP-1, causes elevated levels of CARP-1, and induces G2M arrest and apoptosis in a dose and time-dependent manner.

CARP-1 and its paralog Dbc-1 are large multi-domain, nuclear or perinuclear proteins that play roles in promoting apoptosis. Like CARP-1, Dbc-1 also regulates activities of estrogen receptor and p53 proteins, apoptosis signaling by ADR, and is also a component of the NF-κB proteome. Alignment of the CARP-1 and Dbc-1 proteins revealed that the APC-2 binding epitope of CARP-1 was significantly homologous to the epitope within the C-terminal region of Dbc-1 (FIG. 11C). Additional co-IP-WB experiments further revealed that flag-tagged Dbc-1 interacted with Gst-APC-2, p38, and p53 proteins (FIG. 11D). Dbc-1 however did not interact with NEMO, and is consistent with previous study showing IKKβ interaction with Dbc-1. Whether Dbc-1 binds with the cullin homology domain epitope of APC-2, the endogenous binding of Dbc-1 and APC-2 is constitutive or regulated by cell cycle signaling, and the SMIs identified in the current study also antagonize Dbc-1 interaction with APC-2 remains to be clarified.

The SMIs that were identified represent a novel class of pharmacological agents with potential utility in elucidating the cell cycle and apoptosis signaling pathways. All the SMIs that we identified antagonize binding of CARP-1 with APC-2, albeit with varying dissociation kinetics ($K_d$), while CFM-4 and CFM-5 do so by binding with CARP-1. It remains to be determined whether CFM-1 also binds with CARP-1. The facts that both CFM-1 and CFM-4 elicited G2M cell cycle arrest while only CFM-4 also stimulated CARP-1 levels, activated caspases and induced apoptosis (FIGS. 5 and 7), suggests that CARP-1 binding with APC-2 is involved in regulation of cell cycle. Since APC/$C^{Cdc20}$ E3 ubiquitin ligase is known to finely regulate M-phase, inhibition of CARP-1 binding with APC-2 by CFM-4 likely modulates APC/$C^{Cdc20}$ functions to interfere with G2M progression. In this context, inhibition of UPP by velcade was previously found to promote G2M arrest and apoptosis and together with the facts that velcade exposure caused a modest increase in CARP-1 levels (FIG. 6E), and antagonism of CARP-1 binding with APC-2 by CFM-1 or CFM-4 also induced G2M arrest, further support involvement of CARP-1 in modulating APC/C E3 ubiquitin ligase function to regulate the cell cycle. The SMIs like CFM-1 inhibit cell growth by inducing cell cycle arrest without significant increase in apoptosis.

Whether CARP-1, like Cdc20, is a substrate of APC/C or a co-activator or both is not clear. A potential APC/C co-activator property of CARP-1 can be inferred from following observations. First, ectopic expression of CARP-1 results in loss of cyclin B1 and increased expression of CDKI p21$^{WAF1/CIP1}$. Increased CARP-1, in turn, will bind APC-2 and activate APC/$C^{Cdc20}$ function to induce depletion of cyclin B1, while elevated activities of APC/$C^{Cdh1}$ will culminate into increased levels of CDKI p21$^{WAF1/CIP1}$. Second, since apoptosis signaling by ADR also involved elevated CARP-1 expression, it is likely that ADR-dependent apoptotic effects involve CARP-1-mediated stimulation of APC/C activities and consequent loss of cyclin B1 and increased levels of CDKI p21$^{WAF1/CIP1}$. Finally, CFM-4 binding with CARP-1 prevents CARP-1 from associating with APC-2, and thus interferes with APC/C activities. Loss of CDKIs p21$^{WAF1/CIP1}$ and p27$^{KIP1}$ following treatment of cells with CFM-4 for periods longer than three hours as noted in FIG. 5B is consistent with attenuation of the APC/$C^{Cdh1}$ function/activities. The extent APC/$C^{Cdc20}$ activity is also compromised in the presence of CFM-4 is not clear. CFM-4 nonetheless stimulates CARP-1 expression and caspase-dependent apoptosis signaling to target Cdc20 and cyclin B1 expression (FIGS. 6E and 7D). Depletion of Cdc20 and/or cyclin B1 likely interferes with ability of cells to exit mitosis and thus contribute to G2M arrest and eventual elimination of cells by apoptosis.

In addition to promoting cell cycle arrest, CFM-4 inhibited cell growth in part by inducing apoptosis. With the exception of MCF-10A cells, treatments with CFM-4 inhibited growth of a variety of cells (FIG. 3) in part by inducing CARP-1 levels and diminishing cyclin B1 (FIG. 5), as well as by promoting apoptosis as evidenced by activation of caspases 8, 9 and 3 (FIG. 7). The fact that these CFMs antagonize CARP-1 binding with APC-2, and the ability of CFM-4 to suppress cell growth was dependent on CARP-1 (FIGS. 4 and 6) suggest that CARP-1 levels likely play an important role in regulating apoptosis signaling by these compounds. Further, since pretreatment of cells with pan-caspase or caspase-6 inhibitor interferes with loss of cyclin B1 and Cdc20 proteins by CFM-4 (FIG. 7D) it would suggest that caspase-dependent loss of the key regulators of the G2M and mitotic phases contributes in promoting cell cycle arrest. Caspase targeting of cyclin B1 in the presence of CFM-4 corroborate previous studies where caspase-6 was found to regulate cleavage of cyclin B1 during ADR-induced mitotic catastrophe. Although UPP is well known to target cyclin B1 and Cdc20 during M phase, presence of velcade failed to block loss of both cyclin B1 and Cdc20 in CFM-4-treated cells (FIG. 6E). Since presence of pan-caspase inhibitor zVAD-fmk blocked CFM-4-dependent loss of cyclin B1 and Cdc20 (FIG. 7D) it is likely that, similar to cyclin B1, activated caspases also promote degradation of Cdc20 following induction of apoptosis signaling by CFM-4. The extent apoptosis induction by CFM-4 involves caspase-dependent targeting of Cdc20, the type of caspase(s) in addition to and upstream of caspase 6, and the presence of caspase-targeted motif(s) within the Cdc20 protein are yet to be elucidated. Given that Cdc20 is often considered as a potential oncogene, and the fact that tumor suppressor p53 has been documented to inhibit Cdc20, caspase-mediated targeting of Cdc20 in the presence of CFM-4 may point to a novel mechanism of cell cycle regulation as well as tumor suppression.

Previous studies have revealed involvement of CARP-1 in apoptosis signaling by a variety of stimuli. Apoptosis induction in response to DNA damaging anthracycline toxins ADR or etoposide stimulated CARP-1 levels. Expression of CARP-1 or its apoptosis-promoting peptides inhibited cell growth in part by activating p38 SAPK/MAPK and caspases 9 and 3. Studies have further revealed an important role of CARP-1 binding with the LIM-domain of the Zyxin protein in transducing UV-C-induced apoptosis that also involved activation of caspase-3. The facts that CFM-4 stimulated CARP-1 levels (FIG. 5B) while apoptosis by CFM-4 involved activation of p38 (FIG. 8A), and Caspases (FIG. 7B, 7C), underscore the involvement of CARP-1 in regulating apoptosis signaling and consequent cell growth in the presence of compounds such as CFM-4 or DNA damage-inducing insults. Since both ADR and CFM-4 require CARP-1 for cell growth suppression, it is however unclear whether and to the extent apoptosis stimulation by CFM-4 also involves damage to the DNA in a manner analogous to ADR. Nevertheless, binding of CARP-1 with APC-2 seems to play an important role in regulating cell growth since expression of CARP-1 lacking its APC-2-binding epitope sensitizes cells to inhibition by CFM-4 or ADR (FIG. 4). Treatment of cells with CFM-4 however induced levels of truncated Bid as well as pro-apoptotic BH3-only $Bim_s$ protein (FIG. 8A, 8B). Activation of tBid and/or Bim likely promoted mitochondrial targeting and subsequent activation of caspases-9 and 3. Depletion of Bim on the other hand failed to interfere with the CFM-4-induced increase in CARP-1 levels and activation of caspase-3 but blocked cyclin B1 loss (FIG. 8C) suggesting that Bim activation and mitochondrial targeting are likely downstream of CARP-1. The fact that CFM-4 caused activation of caspase-8, and activated caspase-8 in turn is known to directly activate caspase-3 as well as pro-apoptotic Bid (tBid), it may be that CFM-4-dependent activation of caspase-8 and 3 are early events that lead to mitochondrial targeting by tBid and/or $Bim_s$ to support "feed-back" activation of caspase-3 and other down-stream caspases to target PARP, Cdc20 and cyclin B1. Since caspase-8 is a key initiator caspase for apoptosis by CD95 system, elucidation of the mechanism(s) of caspase-8 activation by small molecular antagonists of CARP-1/APC-2 binding such as CFM-4 will enhance the understanding of the extrinsic apoptosis signaling pathway.

The ability of a compound of the invention to act as an anti-cancer agent may be determined using pharmacological models which are well known to the art, as described herein (e.g. example 1) or using the tests described in example 2.

Example 2

Cancer Cell Growth Inhibition by Compounds of Formula I Including Compounds of the Invention Cancer cells that were tested included the estradiol-receptor (ER) positive human breast cancer MCF-7, ER-negative and Her-2-positive MDA-MB-453 and SKBR-3, the triple negative breast cancer (TNBC) MDA-MB-468 and MDA-MB-231. In addition, human pancreatic cancer (BxPc-3, PANC-1), human prostate cancer (PC-3, LnCaP), human cervical cancer HeLa, and Human mesothelioma (lung cancer) H2461 and 2373 cells were utilized. In the first instance, the MDA-MB-468, HeLa, and H2373 cells were separately treated with 20 micromolar dose of each of the compounds. Determination of viable/live cells was carried out by MTT assay. Approximately $5 \cdot 10^3$ cells were seeded in a 96-well culture plate and subsequently treated with different compounds at different doses and time periods noted above. Control cells were treated with 0.1% dimethyl sulfoxide (DMSO) in culture medium. After treatment, the cells were incubated with 1 mg/ml of MTT reagent at 37° C. for 4 hours and then MTT was removed and 100 µL of DMSO was added, followed by colorimetric analysis using a multilabel plate reader at 560 nm wavelength (Victor$^3$; PerkinElmer, Wellesley, Mass., USA). The compounds that were found to be most active in inhibiting cell viabilities were then tested further for their IC50 dose (the dose that causes a 50% reduction in the number of the viable/live cells) for all the cancer cell types listed above. Each of the cell type was separately treated with 0.1, 0.2, 0.5, 1.0, 2.0, 5.0, 10.0, and 20.0 micromolar doses of each of the compounds for 24, 48, and 72 hours. The IC50 dose of each of the compounds was calculated for each of the cell line. The average optical density values relative to vehicle-treated controls were derived from six replicates for each cell line. Data from two independent experiments was utilized to establish IC50 for each compound for a given cancer cell line. FIG. 14 shows results of these assays for certain compounds of formula I.

Compounds of formula I including compounds of the invention were prepared by the procedures described in the following non-limiting examples.

Example 3

General Experimental Procedures and Preparation of Intermediates

General experimental: Starting materials were purchased from Fisher, Sigma-Aldrich Lancaster, Fluka or TCI-America and were used without purification. All reaction solvents were purchased from Fisher and used as received. Reactions were monitored by TLC using precoated silica gel 60 F254 plates. Silica gel chromatography was performed with silica gel (220-240 mesh) obtained from Silicycle. NMR spectra were recorded on a Varian 400 MHz spectrometer. Chemical shifts are reported in δ (parts per million), by reference to the hydrogenated residues of deuterated solvent as internal standard $CDCl_3$: δ=7.28 ($^1$H NMR). Mass spectra were recorded on a Micromass LCT time-of-flight instrument utilizing the electrospray ionization mode. The purity of the compounds was assessed via analytical reverse phase HPLC with a gradient of 10% acetonitrile/water to 90% acetonitrile/water over 6 minutes (C18 column, 3.5 um, 4.6×100 mm, 254 nm detection) (HPLC system A).

Schemes 1-3 describe synthetic steps that were used to prepare the compounds described in the examples. The chemistry outlined in these schemes can be used to prepare additional compounds of formula I.

Scheme 1

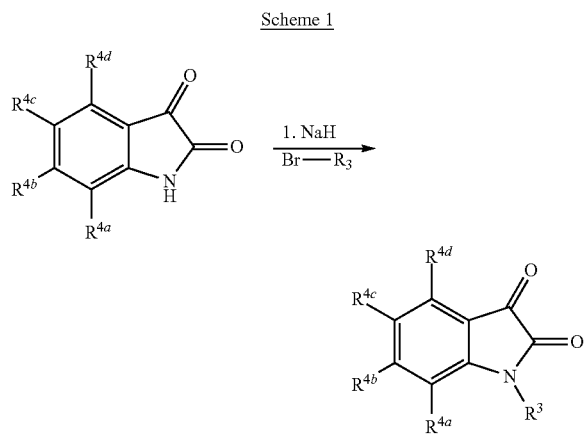

Scheme 2

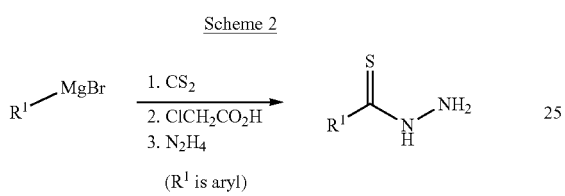

($R^1$ is aryl)

Scheme 3

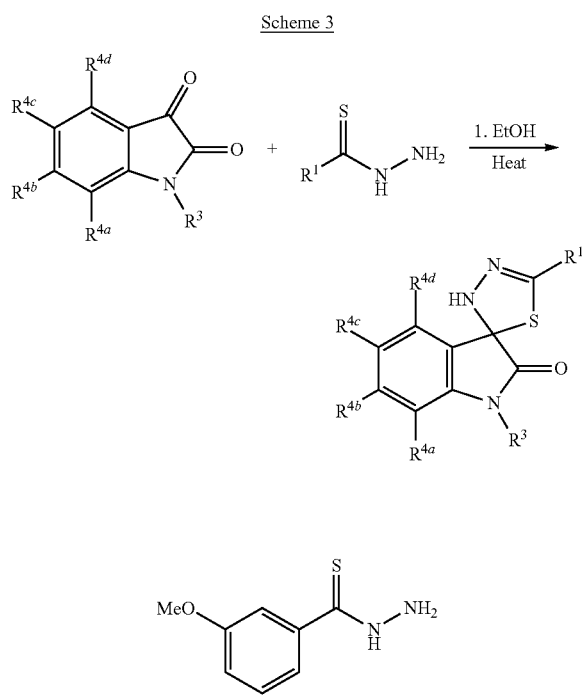

3-methoxybenzothiohydrazide

To a suspension of (3-methoxyphenyl)magnesium bromide (3.0 ml, 3.0 mmol) in ether (10 mL) cooled to −78° C. was added carbon disulfide (0.18 ml, 3.0 mmol) drop wise. The resulting mixture was allowed to warm to room temperature over 1 hour, then stirred at room temperature for 2 hours. The mixture was treated with satd. aqueous $NH_4Cl$ and partitioned between ethyl acetate and water. The layers were separated and the aqueous layer was extracted with ethyl acetate. The combined organic layers were washed with satd. aqueous NaCl solution, dried ($MgSO_4$). The residue was dissolved in abs. ethanol (30 mL) and treated with a solution of 2-chloroacetic acid (0.28 g, 3.0 mmol) and sodium bicarbonate (0.25 g, 3.0 mmol) in water (10 mL) and stirred for 2 hours. The solution was concentrated and acidified with 2 M HC, extracted with EtOAc (2×), washed with satd. aqueous NaCl and dried ($MgSO_4$). The mixture was filtered and concentrated. The residue was dissolved in ethanol and added to a solution of hydrazine (20 mmol) in ethanol (30 ml) and stirred 2 hours and concentrated. The residue was dissolved in EtOAc and washed with water (1×) and satd. aqueous NaCl solution (1×), dried ($MgSO_4$) and concentrated. The residue was triturated with ether and filtered. 3-methoxybenzothiohydrazide was obtained (55% yield) as a tan solid. HPLC system A, 95% ($t_R$=4.8 min).

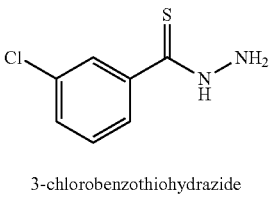 [SMILES: NNC(=S)c1cccc(Cl)c1]

3-chlorobenzothiohydrazide

To a suspension of (3-chlorophenyl)magnesium bromide (6.0 ml, 3.0 mmol) in ether (10 mL) cooled to −78 C was added carbon disulfide (0.18 ml, 3.0 mmol). The resulting mixture was allowed to warm to room temperature over 1 hour. The mixture was stirred at room temperature for 2 hours then treated with satd. $NH_4Cl$ and partitioned between ethyl acetate and water. The layers were separated and extracted and the aqueous layer was extracted with ethyl acetate. The combined organic layers were washed with satd. aqueous NaCl solution and dried ($MgSO_4$). The residue was dissolved in ethanol 30 mL and treated with a solution of 2-chloroacetic acid (0.28 g, 3.0 mmol) and sodium bicarbonate (0.25 g, 3.0 mmol) in water (10 mL). After stirring for 2 hours the solution was acidified with 2 M HCl and extracted with EtOAc (2×), washed with satd. NaCl and dried ($MgSO_4$). The mixture was filtered and concentrated. To a solution of hydrazine (0.41 ml, 13.0 mmol) in ethanol (30 mL) was added portion wise 2-((3-chlorophenylcarbonothioyl)oxy)acetic acid (0.3 g, 1.3 mmol). The resulting mixture was allowed to stir 2 hours at room temperature before concentrating. The residue was dissolved in $CH_2Cl_2$ and washed with water, satd. aqueous NaCl and dried $MgSO_4$. The mixture was filtered and concentrated to provide a solid. The solid was triturated with ether and filtered. 3-chlorobenzothiohydrazide was obtained in 78% yield was a brown solid. HPLC system A, 92% ($t_R$=5.5 min).

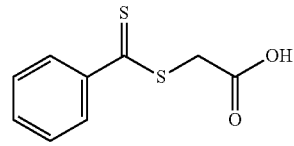

2-((Phenylcarbonothioyl)thio)acetic acid

To a suspension of Mg (1.94 g, 80 mmol) in dry THF (100 mL) were added tiny crystal of iodine and bromobenzene (8.4 mL, 80 mmol) slowly over a period of 20 minutes. The reaction was initiated by warming to 40° C. The reaction was exothermic and the solution started refluxing. After the reaction was over, $CS_2$ (4.8 mL, 80 mmol) was slowly added from a syringe. The reaction was allowed to stir at room temperature for 2 h. Then a solution of chloroacetic acid (7.56 g, 80 mmol) in water (200 mL) was prepared and neutralized with $NaHCO_3$ (6.72 g, 80 mmol). This solution was rapidly added through the condenser and the reaction was brought to boiling by heating to 90° C. and left refluxing for 5 minutes. Then the solution was added to 500 mL of cold water and stirred. Concentrated HCl was slowly added to neutralize the solution. The solution was cooled and stirred for 30 minutes to yield a scarlet red precipitate. The red precipitate was filtered, washed with water, dried under suction and then under vacuum desiccator overnight. TLC indicated there was a slight presence of impurity that was less polar than the product. The crude compound was dissolved in $CHCl_3$ by warming, decanted of from the visible debris, and left at room temperature for crystallization overnight. The crystals were filtered, washed with DCM/hexanes and the solvent was removed under suction. The mother liquor was concentrated and left at room temperature for the recovery of second crop. After 3 h, the crystals were filtered, washed with DCM/hexanes mixture and the solvent was removed under suction. TLC indicated both crops of 2-((phenylcarbonothioyl)thio)acetic acid were identical. Yield: 10.58 g (62%). $^1H$ NMR (400 MHz, $CDCl_3$) δ 10.5 (bs, 1H), 8.02-8.05 (m, 2H), 7.54-7.59 (m, 1H), 7.39-7.43 (m, 2H) & 4.28 (s, 2H).

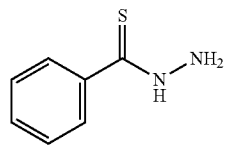

Benzothiohydrazide 2-((Phenylcarbonothioyl)thio)acetic acid (1.15 g, 5.45 mmol) was dissolved in 1N NaOH (5.45 mL) and diluted with 5 mL of water and cooled in ice. To this solution was added hydrazine hydrate (820 mg, 16.35 mmol). Yellow colored compound precipitated out of the solution. The reaction was acidified with 2N HCl. The mixture was cooled in ice for 1 h, filtered, washed with cold water, dried under suction and then under high vacuum overnight to provide benzothiohydrazide. Yield: 0.23 g (28%). $^1H$ NMR (400 MHz, $CDCl_3$) δ 9.01 (bs, 1H), 7.66-7.69 (m, 2H), 7.44-7.48 (m, 1H), 7.35-7.40 (m, 2H) & 4.85 (bs, 2H).

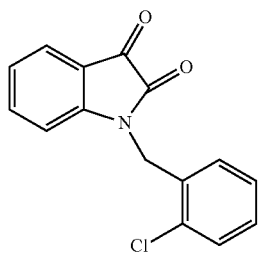

1-(2-Chlorobenzyl)indoline-2,3-dione

To a 0° C. suspension of sodium hydride 60% (1.6 g, 40.8 mmol) in dry THF was added, portion wise, indoline-2,3-dione (5.0 g, 34.0 mmol). After the addition was complete the mixture was stirred 2 hour at 0° C. and then allowed warm to room temperature. The 1-(bromomethyl)-2-chlorobenzene (6.9 g, 34.0 mmol) was then added portion wise and the resulting mixture was stirred overnight at room temperature. The mixture was quenched with 5% citric acid and the layers were separated. The organic layer was washed with satd. aqueous brine (3×) and dried with $MgSO_4$. The mixture was filtered and concentrated to provide a red solid which was triturated in $Et_2O$ and filtered. 1-(2-Chlorobenzyl)indoline-2,3-dione was obtained (73% yield) as a red solid. HPLC system A, 95% ($t_R$=7.2 min). ESI+MS m/z 272.0 (M+H$^+$).

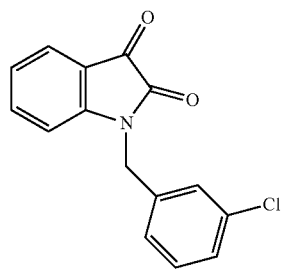

1-(3-Chlorobenzyl)indoline-2,3-dione

NaH (0.4 g, 10 mmol, 60%) was washed with hexane (2×25 mL) and suspended in dry THF (35 mL). Isatin (1.5 g, 10 mmol) was added portion wise slowly over a period of 20 minutes and stirred for 20 min. Then 3-chlorobenzylbromide (1.31 mL, 10 mmol) was added slowly from a syringe. The reaction was stirred at room temperature overnight. The solvent was removed under reduced pressure and the crude product was extracted with EtOAc (50 mL), washed with $H_2O$ (2×25 mL), dried ($Na_2SO_4$) and the solvent was removed under reduced pressure. The residue was dissolved in minimum amount of EtOAc to which hexanes was added and left at room temperature for crystallization. The crystallized compound was filtered washed with 50% EtOAc/hexanes and dried under high vacuum overnight. As there was some starting material left, the compound was purified further by flash chromatography and eluted with eluted with 15-60% EtOAc/hexane over 300 mL at 15 mL/min. The desired fractions were pooled and the solvent was removed to obtain 1-(3-chlorobenzyl)indoline-2,3-dione as a pure orange colored compound (0.76 g (28%)). $^1H$ NMR (400 MHz, $CDCl_3$) δ 7.63 (d, J=7.4, 1H), 7.52 (td, J=7.8 & 1.3 Hz, 1H), 7.21-7.33 (m, 4H), 7.13 (t, J=7.5 Hz, 1H), 6.76 (d, J=7.9 Hz, 1H) & 4.91 (s, 2H).

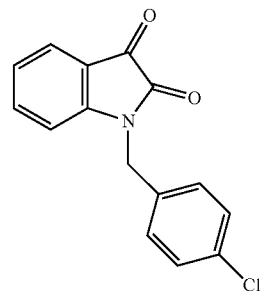

1-(4-chlorobenzyl)indoline-2,3-dione

NaH (0.16 g, 4 mmol, 60%) was suspended in dry THF (35 mL). Isatin (0.6, 4 mmol) was added portion wise slowly over a period of 20 minutes and stirred for 20 min. Then 4-chlorobenzylbromide (0.92, 4.4 mmol) was then added. The reaction was stirred at room temperature overnight. As TLC indicated some presence of the starting material, the reaction was refluxed for 8 h. The solvent was removed under reduced pressure and the crude product was extracted with $CH_2Cl_2$ (50 mL), washed with $H_2O$ (2×25 mL), dried ($Na_2SO_4$) and the solvent was removed under reduced pressure. The residue was dissolved in minimum amount of EtOAc to which hexanes was added and left at room temperature for crystallization. The crystallized compound was filtered, washed with 50% EtOAc/hexanes and dried under high vacuum overnight. Yield: 0.27 g (25%). $^1$H NMR (400 MHz, $CDCl_3$) δ 7.61 (d, J=7.4, 1H), 7.48 (t, J=7.8 Hz, 1H), 7.24-7.32 (m, 4H), 7.09 (t, J=7.6 Hz, 1H), 6.72 (d, J=7.9 Hz, 1H) & 4.88 (s, 2H).

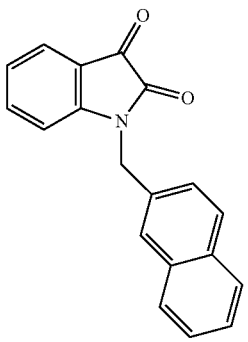

1-(Naphthalen-2-ylmethyl)indoline-2,3-dione

NaH (0.4 g, 10 mmol, 60%) was washed with hexane (2×15 mL) and suspended in dry THF (60 mL). To this suspension, isatin (1.5 g, 10 mmol) was added portion-wise slowly over a period of 10 minutes and stirred for 30 min. Then the bromonapthyl derivative (2.21 g, 10 mmol) was added. The reaction was stirred at reflux overnight. TLC indicated still the presence of some starting material, especially the bromonapthyl derivative. The reaction was set to reflux for further 8 h after the addition of 20 mL of dry THF. TLC after 8 h reflux indicated almost completion of the reaction. The solvent was removed under reduced pressure and the crude product was extracted with DCM (100×2 mL), washed with $H_2O$ (2×25 mL), dried ($Na_2SO_4$) and the solvent was removed under reduced pressure. The residue was dissolved in minimum amount of EtOAc to which hexanes was added and left at RT for crystallization. The crystallized compound was filtered washed with 50% EtOAc/hexanes and dried under high vacuum overnight. Yield: 1.85 g (64%). $^1$H NMR (400 MHz, $CDCl_3$) δ 7.39-7.85 (m, 4H), 7.62 (d, J=7.4 Hz, 1H), 7.48-7.52 (m, 2H), 7.42-7.46 (m, 2H), 7.08 (t, J=7.5 Hz, 1H), 6.81 (d, J=7.9 Hz, 1H) & 5.10 (s, 2H).

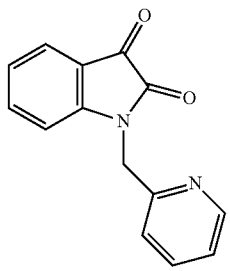

1-(Pyridin-2-ylmethyl)indoline-2,3-dione

NaH (0.6 g, 15 mmol, 60%) was washed with hexane (10 mL) and suspended in dry DMF (6 mL). To this suspension, isatin (0.75 g, 5 mmol) was added slowly over a period of 10 minutes in little portions and stirred for 15 min. Powdered bromopyridium salt (1.27 g, 5 mmol) was then added. The reaction was stirred at room temperature overnight. TLC indicated completion of reaction. Crushed ice was added over the solution and the solution was extracted with EtOAc (3×25 mL). The combined extract was washed with water (3×20 mL), dried ($Na_2SO_4$) and the solvent was removed under reduced pressure. The residue was dissolved in minimum amount of EtOAc to which hexane was added until very slight turbidity was observed. The solution was left for crystallization at room temperature. The solvent was removed and the residue was applied on a column of pre-packed silica gel (40 g, Silicycle) and eluted with 15-80% EtOAc/hexanes over 680 mL at 35 mL/minute. The desired fractions were pooled after TLC analysis and the solvent was removed to give the title compound, 0.252 g (21%). %). $^1$H NMR (400 MHz, $CDCl_3$) δ 8.57 (d, J=4 Hz, 1H), 7.68 (td, J=7.3 & 1.7 Hz, 1H), 7.61 (d, J=7.4 Hz, 1H), 7.51 (t, J=7.7 Hz, 1H), 7.34 (d, J=7.8 Hz, 1H), 7.24 (m, 1H), 7.10 (t, J=7.6 Hz, 1H), 6.97 (d, J=7.9 Hz, 1H) & 5.05 (s, 2H).

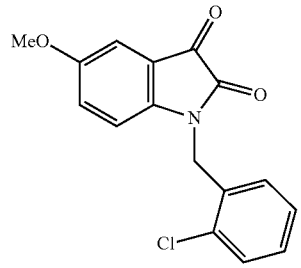

1-(2-Chlorobenzyl)-5-methoxyindoline-2,3-dione

NaH (0.3 g, 7.5 mmol, 60%) was washed with hexane (10 mL) and suspended in dry DMF (6 mL). To this suspension, isatin derivative (0.89 g, 5 mmol) was added slowly over a period of 10 minutes in small portions. The sides of the reaction container were rinsed with 3 mL of DMF to wash in all of the compound. After stirring for 30 minutes the 2-chlorobenzyl bromide (0.65 mL, 5 mmol) was added. The reaction was stirred at room temperature overnight. TLC indicated the reaction was complete. Crushed ice was added over the solution and the solution was extracted with DCM (2×25 mL). The combined extract was washed with water (3×20 mL), dried ($Na_2SO_4$) and the solvent was removed under reduced pressure. The residue was dissolved in minimum amount of EtOAc to which hexane was added until very slight turbidity was observed. The solution was left for crystallization at room temperature for 12 h. The crystallized compound was filtered, washed with 50% EtOAc/hexane, dried under suction and then under high vacuum for overnight to provide the desired compound. Yield: 0.638 g (42%). ¹H NMR (400 MHz, CDCl₃) δ 7.42 (d, J=7.5, 1H), 7.21-7.27 (m, 3H), 7.17 (d, J=2.6 Hz, 1H), 7.05 (m, 1H), 6.68 (d, J=8.6 Hz, 1H), 5.03 (s, 2H) & 3.79 (s, 3H).

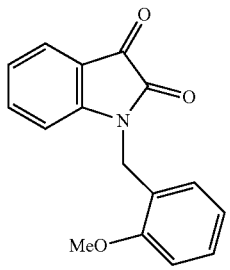

1-(2-Methoxybenzyl)indoline-2,3-dione

NaH (0.3 g, 7.5 mmol, 60%) was washed with hexane (7 mL) and suspended in dry DMF (5 mL). To this suspension, isatin derivative (0.75 g, 5 mmol) was added slowly over a period of 10 minutes in small portions and stirred for 60 min. Then the 2-mehthoxybenzyl chloride (1.3 mL, 5 mmol) was added. The reaction was stirred at room temperature overnight. TLC indicated completion of reaction. Crushed ice was added over the solution and the solution was extracted with DCM (2×25 mL). The combined extract was washed with water (3×20 mL), dried (Na₂SO₄) and the solvent was removed under reduced pressure. The residue was dissolved in minimum amount of EtOAc to which hexane was added until very slight turbidity was observed. The solution was left for crystallization at room temperature for 12 h. The crystallized compound was filtered, washed with 50% EtOAc/hexane, dried under suction and then under high vacuum for 5 h. Yield: 0.39 g (29%). ¹H NMR (400 MHz, CDCl₃) δ 7.59 (d, J=7.4, 1H), 7.48 (t, J=7.6 Hz, 1H), 7.26 (m, 2H), 7.07 (t, J=7.4 Hz, 1H), 6.87-6.93 (m, 3H), 4.95 (s, 2H) & 3.89 (s, 3H).

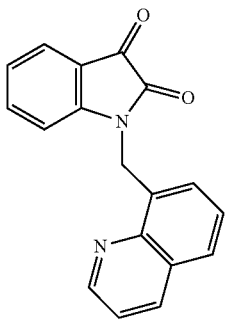

1-(Quinolin-8-ylmethyl)indoline-2,3-dione

NaH (0.135 g, 3.38 mmol, 60%) was washed with hexane (7 mL) and suspended in dry DMF (4 mL). To this suspension, isatin (0.33 g, 2.25 mmol) was added slowly over a period of 10 minutes in small portions and the sides of the reaction container were rinsed with 1.5 mL of DMF to wash in all of the isatin that stuck on the sides. After stirring for 20 minutes 8-(bromomethyl)quinoline (0.5 g, 2.25 mmol) was added. The reaction was stirred at room temperature for 3 h. TLC indicated completion of the reaction. Crushed ice was added over the solution and the precipitated solid was filtered, washed with excess water and dried under high vacuum overnight. The crude compound was dissolved in EtOAc by boiling to which a small amount of hexane was added. The solution was left for crystallization at room temperature for 4 h. The crystallized compound was filtered, washed with 50% EtOAc/hexane, dried under suction and then under high vacuum overnight. Yield: 0.29 g (45%). ¹H NMR (400 MHz, CDCl₃) δ 9.01 (d, J=4.2 Hz, 1H), 8.21 (d, J=8.3 Hz, 1H), 7.80 (d, J=8.2 Hz, 1H), 7.70 (d, J=7.2 Hz, 1H), 7.60 (d, J=7.4 Hz, 1H), 7.78-7.51 (m, 2H), 7.42 (t, J=7.8 Hz, 1H), 7.02-7.07 (m, 2H) & 5.70 (s, 2H).

Example 4

1-[(2-Chlorophenyl)methyl]-5'-(3-methoxyphenyl)-1,2-dihydro-3'H-spiro[indole-3,2'-[1,3,4]thiadiazole]-2-one (1)

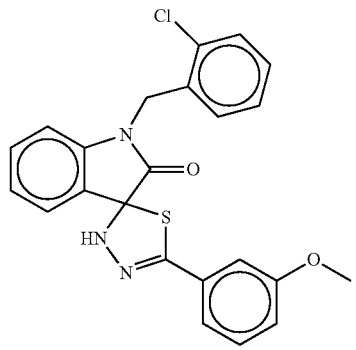

3-Methoxybenzothiohydrazide (0.11 g, 0.60 mmol) was dissolved in ethanol (10 mL) and 1-(2-chlorobenzyl)indoline-2,3-dione (0.16 g, 0.60 mmol) was added in one portion. Two drops of HOAc were added and the reaction was heated to 60° C. for 2 hours. The mixture was filtered and dried under vacuum overnight. The desired compound was obtained (60.8% yield) as a yellow solid. HPLC system A, 95% (t_R=7.2 min) ¹H NMR (400 MHz, DMSO-d6) δ 9.01 (s, 1H), 7.60 (dd, J=7.4, 1.3 Hz, 1H), 7.53-7.44 (m, 1H), 7.44-7.22 (m, 3H), 7.22-7.01 (m, 4H), 7.01-6.87 (m, 1H), 6.79 (d, J=7.9 Hz, 1H), 5.18-4.67 (m, 3H), 3.77 (d, J=0.6 Hz, 3H).

Example 5

5'-(3-Chlorophenyl)-1-[(2-chlorophenyl)methyl]-1,2-dihydro-3'H-spiro[indole-3,2'-[1,3,4]thiadiazole]-2-one (2)

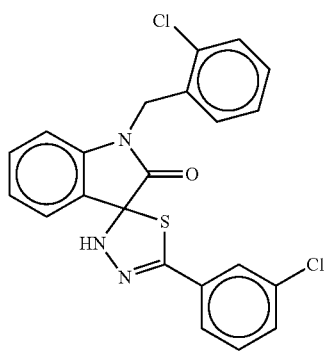

3-Chlorobenzothiohydrazide (0.09 g, 0.48 mmol) was dissolved in ethanol (10 ml) and 1-(2-chlorobenzyl)indoline-2,3-dione (0.13 g, 0.48 mmol) was added in one portion. Two drops of HOAc were added and the mixture was heated to 60° C. for 2 hours. The mixture was filtered and dried under vacuum overnight. The title compound was obtained (85% yield) as an orange solid. HPLC system A, 96% ($t_R$=8.9 min) $^1$H NMR (400 MHz, DMSO-d6) δ 9.17 (s, 1H), 7.72-7.53 (m, 3H), 7.53-7.39 (m, 3H), 7.30 (m, 3H), 7.25-7.01 (m, 2H), 6.80 (d, J=7.9 Hz, 1H), 4.93 (m, 2H).

Example 6

5-Chloro-1-[(2-chlorophenyl)methyl]-5'-phenyl-1,2-dihydro-3'H-spiro[indole-3,2'-[1,3,4]thiadiazole]-2-one (3)

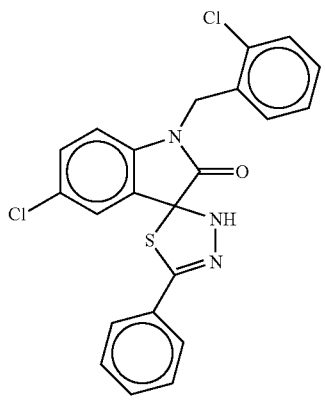

Benzothiohydrazide (0.09 g, 0.59 mmol) was dissolved in ethanol (10 mL) and 5-chloro-1-(2-chlorobenzyl)indoline-2,3-dione (0.181 g, 0.59 mmol) was added in one portion. Two drops of HOAc were added and the reaction was heated to 60° C. for 2 hours. The mixture was filtered and dried under vacuum overnight.
The desired compound was obtained (77% yield) as a yellow solid. HPLC system A, 99% ($t_R$=8.9 min) $^1$H NMR (400 MHz, DMSO-d6) δ 9.03 (s, 1H), 7.68-7.23 (m, 8H), 7.23-7.13 (m, 1H), 6.84 (d, J=8.5 Hz, 1H), 5.11-4.65 (m, 2H).

Example 7

1-[(2-Chlorophenyl)methyl]-5'-(2-methylphenyl)-1,2-dihydro-3'H-spiro[indole-3,2'-[1,3,4]thiadiazole]-2-one (4)

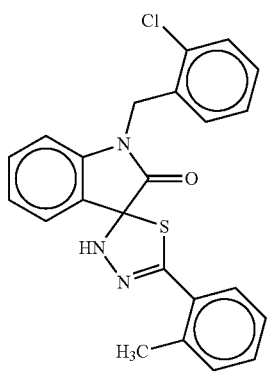

2-Methylbenzothiohydrazide (0.12 g, 0.72 mmol) was dissolved in ethanol (10 mL) and 1-(2-chlorobenzyl)indoline-2,3-dione (0.19 g, 0.72 mmol) was added in one portion. Two drops HOAc were added and the reaction was heated to 60° C. for 12 hours. The mixture was filtered, washed with EtOH, and dried under vacuum overnight. The desired compound was obtained (21% yield) as a red solid. HPLC system A, 97% ($t_R$=8.87 min) $^1$H NMR (400 MHz, Chloroform-d) δ 7.66 (dd, J=7.5, 1.3 Hz, 1H), 7.59-7.34 (m, 2H), 7.34-6.94 (m, 8H), 6.70 (d, J=7.8 Hz, 1H), 6.49 (s, 1H), 5.28-4.84 (m, 2H), 2.61 (s, 3H). ESI-MS m/z 420.0 (M+H$^+$).

Example 8

1-(3-Chlorobenzyl)-5'-phenyl-3'H-spiro[indoline-3,2'-[1,3,4]thiadiazol]-2-one (5)

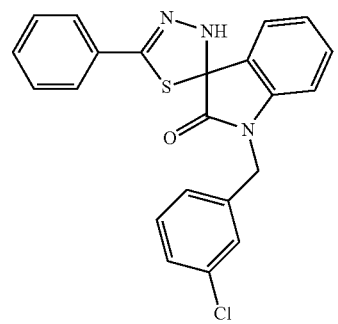 [SMILES: O=C1N(Cc2cccc(Cl)c2)c2ccccc2C12NN=C(c1ccccc1)S2]

To a solution of benzothiohydrazide (12.3 mg, 0.08 mmol) in EtOH (0.4 mL) was added 3-chlorobenzylisatin (22 mg, 0.08 mmol). The solution was stirred at 45° C. for 1.5 h. TLC (50% DCM/hexane) indicated completion of reaction. The precipitate was filtered washed with 50% EtOAc/hexanes (2 mL), dried under suction and then under high vacuum overnight to provide the desired compound. Yield: 23 mg (70%). $^1$H NMR (400 MHz, DMSO-d$^6$) δ 9.05 (s, 1H), 7.58-7.63 (m, 3H), 7.42-7.49 (m, 4H), 7.30-7.40 (m, 4H), 7.14 (t, J=7.5 Hz, 1H), 6.96 (d, J=7.9 Hz, 1H), 4.97 (d, J=16 Hz, 1H) & 4.88 (d, J=16 Hz, 1H).

Example 9

1-(4-Chlorobenzyl)-5'-phenyl-3'H-spiro[indoline-3,2'-[1,3,4]thiadiazol]-2-one (6)

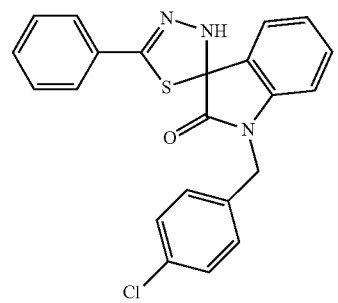 [SMILES: O=C1N(Cc2ccc(Cl)cc2)c2ccccc2C12NN=C(c1ccccc1)S2]

To a solution of benzothiohydrazide (23 mg, 0.15 mmol) in EtOH (0.8 mL) was added 4-chlorobenzylisatin (41 mg, 0.15 mmol). The solution was stirred at 45° C. for 1.5 h.

TLC (50% DCM/hexane) indicated completion of reaction. The solvent was removed and the residue was dissolved in 0.4 mL of EtOAc to which about 1 mL of hexanes was added. The sides were scratched to induce crystallization. The precipitate was filtered, washed with 50% EtOAc/hexanes (2 mL), dried under suction then under high vacuum overnight to provide the desired compound. Yield: 45 mg (73%). $^1$H NMR (400 MHz, DMSO-d$^6$) δ 9.01 (s, 1H), 7.57-7.61 (m, 3H), 7.32-7.47 (m, 8H), 7.13 (t, J=6.8 Hz, 1H), 6.95 (d, J=7.4 Hz, 1H), 4.93 (d, J=15.3 Hz, 1H) & 4.87 (d, J=16.1 Hz, 1H).

Example 10

1-(Naphthalen-2-ylmethyl)-5'-phenyl-3'H-spiro[indoline-3,2'-[1,3,4]thiadiazol]-2-one (7)

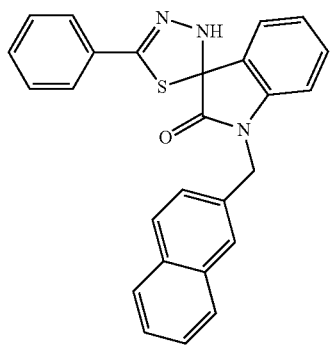 [SMILES: O=C1N(Cc2ccc3ccccc3c2)c2ccccc2C12NN=C(c1ccccc1)S2]

To a solution of benzothiohydrazide (23 mg, 0.15 mmol) in EtOH (0.8 mL) was added 2-napthylmethylisatin (43 mg, 0.15 mmol). The solution was stirred at 55° C. for 3 h. The red color of the solution disappeared and the compound precipitated out of the solution. The mixture was cooled in ice for 1 h, filtered and washed with 2 mL of cold EtOH. The solids were dried under suction and then under high vacuum to provide the desired compound. Yield: 56 mg (88%). $^1$H NMR (400 MHz, DMSO-d$^6$) δ 9.09 (s, 1H), 7.87-7.94 (m, 4H), 7.59-7.63 (m, 3H), 7.44-7.54 (m, 6H), 7.31 (t, J=7.7 Hz, 1H), 7.12 (t, J=7.5 Hz, 1H), 6.98 (d, J=7.9 Hz, 1H), 5.12 (d, J=15.9 Hz, 1H) & 5.04 (d, J=15.9 Hz, 1H).

Example 11

5'-Phenyl-1-(pyridin-2-ylmethyl)-3'H-spiro[indoline-3,2'-[1,3,4]thiadiazol]-2-one (8)

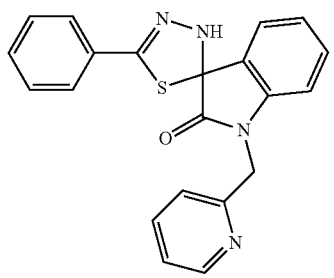 [SMILES: O=C1N(Cc2ccccn2)c2ccccc2C12NN=C(c1ccccc1)S2]

To a solution of benzothiohydrazide (23 mg, 0.15 mmol) in EtOH (0.8 mL) was added 2-pyridylisatin (36 mg, 0.15 mmol). The solution was stirred at 55° C. for 3 h. The red color of the solution disappeared and the compound precipitated out of the solution. The mixture was cooled in ice for 1 h, filtered and washed with 2 mL of cold EtOH. The solids were dried under suction and then under high vacuum to provide the desired compound. Yield: 43 mg (76%). $^1$H NMR (400 MHz, DMSO-d$^6$) δ 9.00 (s, 1H), 8.53 (d, J=4.4 Hz, 1H), 7.79 (t, J=7.3 Hz, 1H), 7.59 (m, 3H), 7.45 (m, 3H), 7.32 (m, 3H), 7.13 (t, J=7.5 Hz, 1H), 6.92 (d, J=7.8 Hz, 1H), & 4.99 (s, 1H).

Example 12

1-(2-Chlorobenzyl)-5-methoxy-5'-phenyl-3'H-spiro[indoline-3,2'-[1,3,4]thiadiazol]-2-one (9)

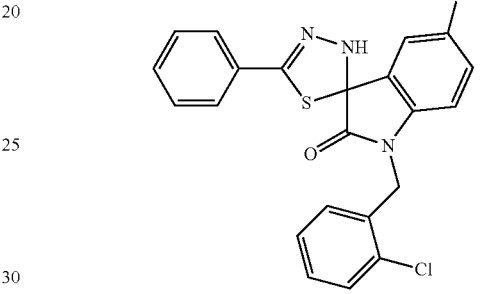

To a solution of the hydrazide (23 mg, 0.15 mmol) in EtOH (0.8 mL) was added the isatin derivative (46 mg, 0.15 mmol). The solution was stirred at 55° C. for 3 h. The red color of the solution persisted and the compound precipitated out of the solution. The mixture was cooled in ice for 1 h, filtered and washed with 2 mL of cold EtOH. The solids were dried under suction and then under high vacuum to provide the desired compound. Yield: 0.056 g (85%). $^1$H NMR (400 MHz, DMSO-d$^6$) δ 9.05 (s, 1H), 7.58-7.60 (m, 2H), 7.53 (d, J=7.4 Hz, 1H), 7.44-7.49 (m, 3H), 7.34 (m, 2H), 7.21 (m, 2H), 6.91 (d, J=8.6 Hz, 1H), 6.74 (d, J=8.6 Hz, 1H), 4.97 (d, J=16.7 Hz, 1H), 4.90 (d, J=16.8 Hz, 1H) & 3.73 (s, 3H).

Example 13

1-(2-Methoxybenzyl)-5'-phenyl-M-spiro[indoline-3,2'-[1,3,4]thiadiazol]-2-one (10)

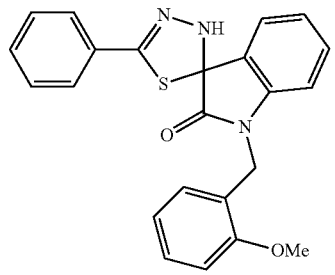 [SMILES: COc1ccccc1CN1C(=O)C2(NN=C(c3ccccc3)S2)c2ccccc21]

To a solution of the hydrazide (23 mg, 0.15 mmol) in EtOH (0.8 mL) was added the isatin derivative (40 mg, 0.15 mmol). The solution was stirred at 55° C. for 3 h. The red color of the solution persisted and the compound precipitated out of the solution. The mixture was cooled in ice for 1 h, filtered and washed with 2 mL of cold EtOH. The solids were dried under suction and then under high vacuum to provide the desired compound. Yield: 0.047 g (77%). $^1$H NMR (400 MHz, DMSO-d$^6$) δ 9.01 (s, 1H), 7.57-7.60 (m, 3H), 7.43-7.49 (m, 3H), 7.27-7.34 (m, 2H), 7.05-7.12 (m, 3H), 6.90 (t, J=7.4 Hz, 1H), 6.83 (d, J=7.8 Hz, 1H), 4.88 (d, J=16.3 Hz, 1H), 4.77 (d, J=16.3 Hz, 1H) & 3.87 (s, 3H).

Example 14

5'-Phenyl-1-(quinolin-8-ylmethyl)-3'H-spiro[indoline-3,2'-[1,3,4]thiadiazol]-2-one (11)

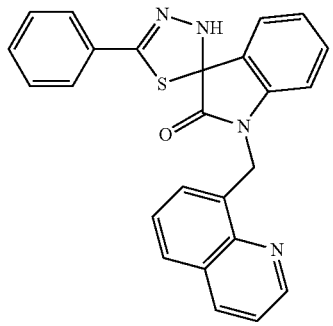 [SMILES: O=C1N(Cc2cccc3cccnc23)c2ccccc2C12NN=C(c1ccccc1)S2]

To a solution of the hydrazide (23 mg, 0.15 mmol) in EtOH (0.8 mL) was added 1-(quinolin-8-ylmethyl)indoline-2,3-dione (44 mg, 0.15 mmol). The solution was stirred at 55° C. for 3 h. The red color of the solution persisted and the compound precipitated out of the solution. The mixture was cooled in ice for 1 h and filtered. The solids were washed with 2 mL of cold EtOH, dried under suction and then under high vacuum to provide the desired compound. Yield: 0.052 g (81%). $^1$H NMR (400 MHz, DMSO-d$^6$) δ 9.09 (s, 1H), 9.05 (m, 1H), 8.45 (d, J=8.3 Hz, 1H), 7.96 (d, J=8 Hz, 1H), 7.55-7.64 (m, 5H), 7.43-7.48 (m, 4H), 7.27 (t, J=7.8 Hz, 1H), 7.12 (t, J=7.5 Hz, 1H), 6.85 (d, J=7.8 Hz, 1H), 5.60 (d, J=17 Hz, 1H) & 5.50 (d, J=16.9 Hz, 1H).

Example 15

The following illustrate representative pharmaceutical dosage forms, containing a compound of formula I or formula II ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

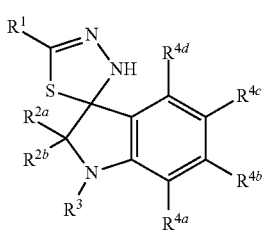

wherein:
R$^1$ is (C$_1$-C$_6$)alkylaryl, wherein any (C$_1$-C$_6$)alkylaryl of R$^1$ is optionally substituted with one or more groups selected from (C$_1$-C$_6$)alkyl, (C$_2$-C$_6$)alkenyl, (C$_2$-C$_6$)

alkynyl, $(C_3-C_7)$carbocycle, halogen, —CN, —$OR_{a1}$, —$NR_{q1}R_{r1}$, —$NR_{n1}COR_{p1}$, $NO_2$, —$C(O)R_{n1}$ and —$C(O)OR_{n1}$ or $R^1$ is

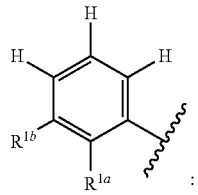

wherein each $R^{1a}$ and $R^{1b}$ is independently selected from H, $(C_2-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$;

$R^{2a}$ and $R^{2b}$ are each H, or $R^{2a}$ and $R^{2b}$ together are oxo (=O);

$R^3$ is —$(C_1-C_6)$alkylaryl or —$(C_1-C_6)$alkylheteroaryl, wherein any —$(C_1-C_6)$alkylaryl or —$(C_1-C_6)$alkylheteroaryl of $R^3$ is optionally substituted with one or more groups selected from $Z^1$, $(C_1-C_6)$alkyl, $(C_2-C_6)$alkenyl and $(C_2-C_6)$alkynyl;

$R^{4a}$ is H, $(C_1-C_8)$alkyl, $(C_2-C_6)$alkenyl, $(C_2-C_6)$alkynyl, $(C_3-C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4b}$ is H, $(C_1-C_8)$alkyl, $(C_2-C_8)$alkenyl, $(C_2-C_8)$alkynyl, $(C_3-C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4c}$ is H, $(C_1-C_8)$alkyl, $(C_2-C_8)$alkenyl, $(C_2-C_8)$alkynyl, $(C_3-C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

$R^{4d}$ is H, $(C_1-C_8)$alkyl, $(C_2-C_8)$alkenyl, $(C_2-C_8)$alkynyl, $(C_3-C_7)$carbocycle, halogen, —CN, —$OR_{n3}$, —$NR_{q3}R_{r3}$, —$NR_{n3}COR_{p3}$, $NO_2$, —$C(O)R_{n3}$ or —$C(O)OR_{n3}$;

each $Z^1$ is independently selected from $(C_3-C_7)$carbocycle, halogen, —CN, —$OR_{n2}$, —$NR_{q2}R_{r2}$, —$NR_{n2}COR_{p2}$, $NO_2$, —$C(O)R_{n2}$ and —$C(O)OR_{n2}$;

each $R_{n1}$ is independently selected from H, $(C_1-C_6)$alkyl, $(C_2-C_6)$alkenyl, $(C_2-C_6)$alkynyl and $(C_3-C_7)$carbocycle;

each $R_{p1}$ is independently selected from $(C_1-C_6)$alkyl, $(C_2-C_6)$alkenyl, $(C_2-C_6)$alkynyl and $(C_3-C_7)$carbocycle;

$R_{q1}$ and $R_{n1}$ are each independently selected from H, $(C_1-C_6)$alkyl, $(C_2-C_6)$alkenyl, $(C_2-C_6)$alkynyl and $(C_3-C_7)$carbocycle, or $R_{q1}$ and $R_{n1}$ together with the nitrogen to which they are attached form a heterocycle;

each $R_{n2}$ is independently selected from H, $(C_1-C_6)$alkyl, $(C_2-C_6)$alkenyl, $(C_2-C_6)$alkynyl and $(C_3-C_7)$carbocycle;

each $R_{p2}$ is independently selected from $(C_1-C_6)$alkyl, $(C_2-C_6)$alkenyl, $(C_2-C_6)$alkynyl and $(C_3-C_7)$carbocycle;

$R_{q2}$ and $R_{r2}$ are each independently selected from H, $(C_1-C_6)$alkyl, $(C_2-C_6)$alkenyl, $(C_2-C_6)$alkynyl and $(C_3-C_7)$carbocycle, or $R_{q2}$ and $R_{r2}$ together with the nitrogen to which they are attached form a heterocycle;

each $R_{q3}$ is independently selected from H, $(C_1-C_6)$alkyl, $(C_2-C_6)$alkenyl, $(C_2-C_6)$alkynyl and $(C_3-C_7)$carbocycle;

each $R_{p3}$ is independently selected from $(C_1-C_6)$alkyl, $(C_2-C_6)$alkenyl, $(C_2-C_6)$alkynyl and $(C_3-C_7)$carbocycle; and $R_{q3}$ and $R_{r3}$ are each independently selected from H, $(C_1-C_6)$alkyl, $(C_2-C_6)$alkenyl, $(C_2-C_6)$alkynyl and $(C_3-C_7)$carbocycle, or $R_{q3}$ and $R_{r3}$ together with the nitrogen to which they are attached form a heterocycle;

or a pharmaceutically acceptable salt thereof;

provided:

$R^3$ is not 2-chlorophenylmethyl, 2-fluorophenylmethyl, 2,6-dichlorophenylmethyl, 4-chlorophenylmethyl, or 4-fluorophenylmethyl when $R^1$ is phenyl, $R^{4a}$ is H, $R^{4b}$ is H, $R^{4c}$ is H, $R^{4d}$ is H and $R^{2a}$ and $R^{2b}$ together are oxo (=O);

$R^3$ is not 2-phenylethyl when $R^1$ is phenyl, $R^{4a}$ is H, $R^{4b}$ is H, $R^{4c}$ is Br, $R^{4d}$ is H and $R^{2a}$ and $R^{2b}$ together are oxo (=O); and provided that:

when $R^3$ is benzyl the benzyl is substituted with one or more groups selected from $Z^1$, $(C_1-C_6)$alkyl, $(C_2-C_6)$alkenyl and $(C_7-C_6)$alkynyl; and when $R^3$ is substituted naphthylmethyl-, the substituted naphthylmethyl- is substituted with one or more groups selected from $Z^1$, $(C_7-C_6)$alkenyl and $(C_2-C_6)$alkynyl and at least one of $R^{1a}$ or $R^{1b}$ is selected from $(C_1-C_6)$alkyl, $(C_2-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$; and the remaining $R^{1a}$ or $R^{1b}$ is selected from H, $(C_2-C_6)$alkenyl, $(C_2-C_6)$alkynyl, $(C_3-C_2)$carbocycle, halogen, —CN, —$OR_{n1}$, —$NR_{q1}R_{r1}$, —$NR_nCOR_{p1}$, $NO_2$, —$C(O)R_{n1}$ and —$C(O)OR_{n1}$; or when $R^3$ is unsubstituted naphthylmethyl at least one of $R^{1a}$ or $R^{1b}$ is independently selected from $(C_7-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$ and the remaining $R^{1a}$ or $R^{1b}$ is selected from H, $(C_1-C_6)$alkyl, $(C_2-C_6)$alkenyl, $(C_7-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$.

2. The compound of claim 1 wherein $R^{2a}$ and $R^{2b}$ together are oxo (=O).

3. The compound of claim 1 wherein $R^3$ is —$(C_1-C_6)$alkylaryl, wherein —$(C_1-C_6)$alkylaryl is optionally substituted with one or more groups selected from $Z^1$, $(C_1-C_6)$alkyl, $(C_2-C_6)$alkenyl and $(C_2-C_6)$alkynyl.

4. The compound of claim 1 wherein each $Z^1$ is independently selected from $(C_3-C_7)$carbocycle, Br, I, —CN, —$OR_{n2}$, —$O(C_3-C_7)$carbocycle, —$NR_{q2}R_{r2}$, —$NR_{n2}COR_{p2}$, $NO_2$, —$C(O)R_{n2}$ and —$C(O)OR_{n2}$.

5. The compound of claim 1 wherein $R^1$ is:

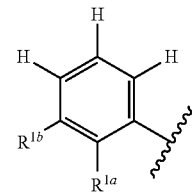

wherein each $R^{1a}$ and $R^{1b}$ is independently selected from H, $(C_1-C_6)$alkyl, $(C_2-C_6)$alkenyl, $(C_7-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$.

6. The compound of claim 1 selected from:
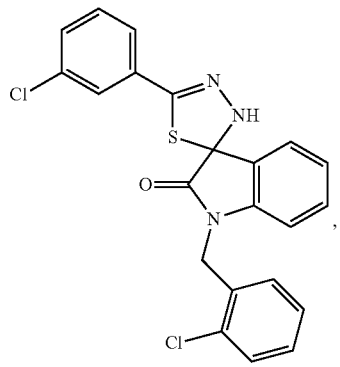
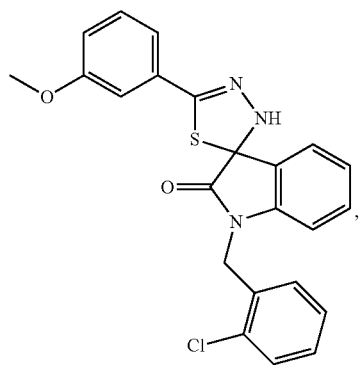
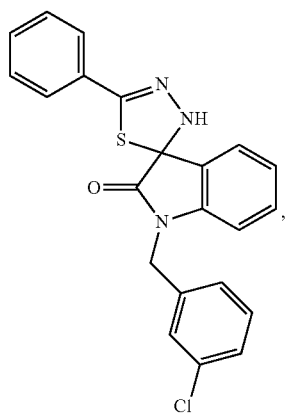
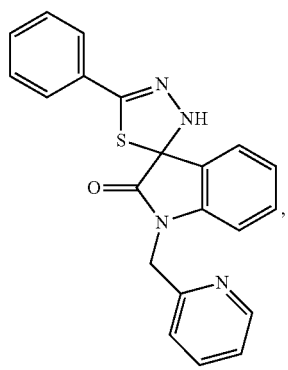
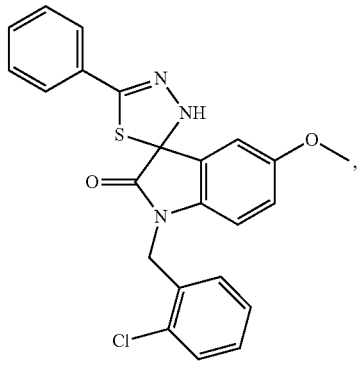
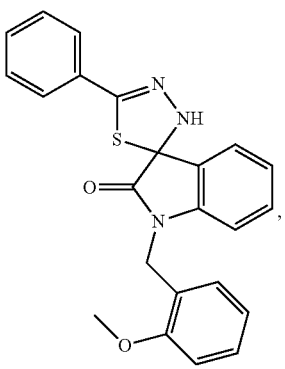
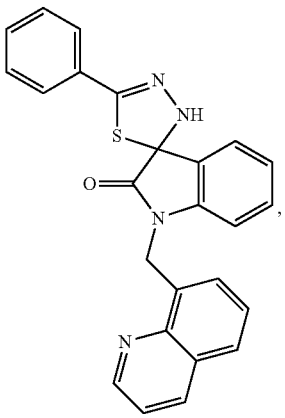
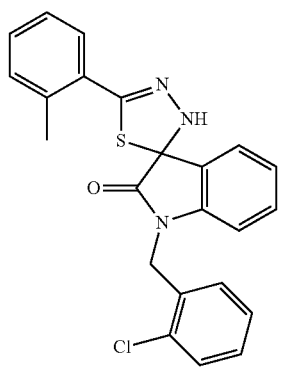
and -continued

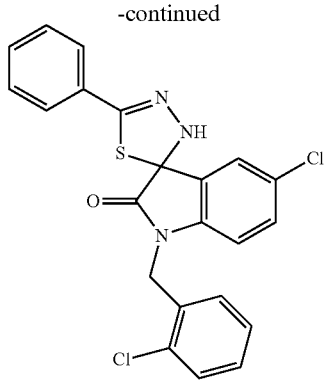

and pharmaceutically acceptable salts thereof.

7. A pharmaceutical composition comprising a compound of formula I as described in claim 1, or a pharmaceutically acceptable salt thereof, and a pharmaceutically acceptable carrier.

8. A method for treating breast cancer, pancreatic cancer or a mesothelioma in a mammal comprising administering to the mammal an effective amount of a compound of formula I as described in claim 1, or a pharmaceutically acceptable salt thereof.

9. A method for treating breast cancer, pancreatic cancer or a mesothelioma in a mammal comprising administering to the mammal an effective amount of a compound of formula I:

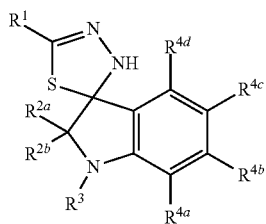

wherein:
R$^1$ is aryl or —(C$_1$-C$_6$)alkylaryl, wherein any aryl or —(C$_1$-C$_6$)alkylaryl of R$^1$ is optionally substituted with one or more groups selected from (C$_1$-C$_6$)alkyl, (C$_2$-C$_6$)alkenyl, (C$_2$-C$_6$)alkynyl, (C$_3$-C$_7$)carbocycle, halogen, —CN, —OR$_{n1}$, —NR$_{q1}$R$_{r1}$, —NR$_{n1}$COR$_{p1}$, NO$_2$, —C(O)R$_{n1}$ and —C(O)OR$_{n1}$;

R$^{2a}$ and R$^{2b}$ are each H, or R$^{2a}$ and R$^{2b}$ together are oxo(=O);

R$^3$ is (C$_1$-C$_6$)alkyl, —(C$_1$-C$_6$)alkylaryl or —(C$_1$-C$_6$)alkylheteroaryl, wherein any (C$_1$-C$_6$)alkyl of R$^3$ is optionally substituted with one or more Z$^1$ groups and wherein any —(C$_1$-C$_6$)alkylaryl or —(C$_1$-C$_6$)alkylheteroaryl of R$^3$ is optionally substituted with one or more groups selected from Z$^1$, (C$_1$-C$_6$)alkyl, (C$_2$-C$_6$)alkenyl and (C$_2$-C$_6$)alkynyl;

R$^{4a}$ is H, (C$_1$-C$_8$)alkyl, (C$_2$-C$_8$)alkenyl, (C$_2$-C$_6$)alkynyl, (C$_3$-C$_7$)carbocycle, halogen, —CN, —OR$_{n3}$, —NR$_{q3}$R$_{r3}$, —NR$_{n3}$COR$_{p3}$, NO$_2$, —C(O)R$_{n3}$ or —C(O)OR$_{n3}$;

R$^{4b}$ is H, (C$_1$-C$_8$)alkyl, (C$_2$-C$_8$)alkenyl, (C$_2$-C$_8$)alkynyl, (C$_3$-C$_7$)carbocycle, halogen, —CN, —OR$_{n3}$, —NR$_{q3}$R$_{r3}$, —NR$_{n3}$COR$_{p3}$, NO$_2$, —C(O)R$_{n3}$ or —C(O)OR$_{n3}$;

R$^{4c}$ is H, (C$_1$-C$_8$)alkyl, (C$_2$-C$_8$)alkenyl, (C$_2$-C$_8$)alkynyl, (C$_3$-C$_7$)carbocycle, halogen, —CN, —OR$_{n3}$, —NR$_{q3}$R$_{r3}$, —NR$_{n3}$COR$_{p3}$, NO$_2$, —C(O)R$_{n3}$ or —C(O)OR$_{n3}$;

R$^{4d}$ is H, (C$_1$-C$_8$)alkyl, (C$_2$-C$_8$)alkenyl, (C$_2$-C$_8$)alkynyl, (C$_3$-C$_7$)carbocycle, halogen, —CN, —OR$_{n3}$, —NR$_{q3}$R$_{r3}$, —NR$_{n3}$COR$_{p3}$, NO$_2$, —C(O)R$_{n3}$ and —C(O)OR$_{n3}$;

each Z$^1$ is independently selected from (C$_3$-C$_7$)carbocycle, halogen, —CN, —OR$_{n2}$, —NR$_{q2}$R$_{r2}$, —NR$_{n2}$COR$_{p2}$, NO$_2$, —C(O)R$_{n2}$ and —C(O)OR$_{n2}$;

each R$_{n1}$ is independently selected from H, (C$_1$-C$_6$)alkyl, (C$_2$-C$_6$)alkenyl, (C$_2$-C$_6$)alkynyl and (C$_3$-C$_7$)carbocycle;

each R$_{p1}$ is independently selected from (C$_1$-C$_6$)alkyl, (C$_2$-C$_6$)alkenyl, (C$_2$-C$_6$)alkynyl and (C$_3$-C$_7$)carbocycle;

R$_{q1}$ and R$_{r1}$ are each independently selected from H, (C$_1$-C$_6$)alkyl, (C$_2$-C$_6$)alkenyl, (C$_2$-C$_6$)alkynyl and (C$_3$-C$_7$)carbocycle, or R$_{q1}$ and R$_{r1}$ together with the nitrogen to which they are attached form a heterocycle;

each R$_{n2}$ is independently selected from H, (C$_1$-C$_6$)alkyl, (C$_2$-C$_6$)alkenyl, (C$_2$-C$_6$)alkynyl and (C$_3$-C$_7$)carbocycle;

each R$_{p1}$ is independently selected from (C$_1$-C$_6$)alkyl, (C$_2$-C$_6$)alkenyl, (C$_2$-C$_6$)alkynyl and (C$_3$-C$_7$)carbocycle;

R$_{q2}$ and R$_{r2}$ are each independently selected from H, (C$_1$-C$_6$)alkyl, (C$_2$-C$_6$)alkenyl, (C$_2$-C$_6$)alkynyl and (C$_3$-C$_7$)carbocycle, or R$_{q2}$ and R$_{r2}$ together with the nitrogen to which they are attached form a heterocycle;

each R$_{n3}$ is independently selected from H, (C$_1$-C$_6$)alkyl, (C$_2$-C$_6$)alkenyl, (C$_2$-C$_6$)alkynyl and (C$_3$-C$_7$)carbocycle;

each R$_{p3}$ is independently selected from (C$_1$-C$_6$)alkyl, (C$_2$-C$_6$)alkenyl, (C$_2$-C$_6$)alkynyl and (C$_3$-C$_7$)carbocycle; and R$_{q3}$ and R$_{r3}$ are each independently selected from H, (C$_1$-C$_6$)alkyl, (C$_2$-C$_6$)alkenyl, (C$_2$-C$_6$)alkynyl and (C$_3$-C$_7$)carbocycle, or R$_{q3}$ and R$_{r3}$ together with the nitrogen to which they are attached form a heterocycle;

or a pharmaceutically acceptable salt thereof.

10. The method of claim 9 wherein the compound of formula I is a compound of formula Ia:

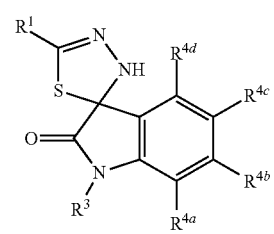

or a pharmaceutically acceptable salt thereof.

11. The method of claim 9 wherein R$^3$ is (C$_1$-C$_6$)alkyl or —(C$_1$-C$_6$)alkylaryl, wherein any (C$_1$-C$_6$)alkyl of R$^3$ is optionally substituted with one or more Z$^1$ groups and wherein any —(C$_1$-C$_6$)alkylaryl is optionally substituted with one or more groups selected from Z$^1$, (C$_1$-C$_6$)alkyl, (C$_2$-C$_6$)alkenyl and (C$_2$-C$_6$)alkynyl.

12. The method of claim 9 wherein R$^3$ is —(C$_1$-C$_6$)alkylaryl, wherein —(C$_1$-C$_6$)alkylaryl is optionally substituted with one or more groups selected from $Z^1$, $(C_1-C_6)$alkyl, $(C_2-C_6)$alkenyl and $(C_2-C_6)$alkynyl.

13. The method of claim 9 wherein $R^1$ is phenyl or —$(C_1-C_6)$alkylphenyl, wherein any phenyl or —$(C_1-C_6)$alkylphenyl of $R^1$ is optionally substituted with one or more groups selected from $(C_1-C_6)$alkyl, $(C_2-C_6)$alkenyl, $(C_2-C_6)$alkynyl, $(C_3-C_7)$carbocycle, halogen, —CN, —$OR_{n1}$, —$NR_{q1}R_{r1}$, —$NR_{n1}COR_{p1}$, $NO_2$, —$C(O)R_{n1}$ and —$C(O)OR_{n1}$.

14. The method of claim 9 wherein each $R^{4a}$, $R^{4b}$, $R^{4c}$ and $R^{4d}$ is independently H or halogen.

15. The method of claim 9 wherein the compound of formula I is selected from

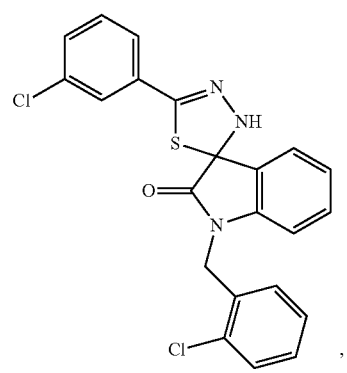

,

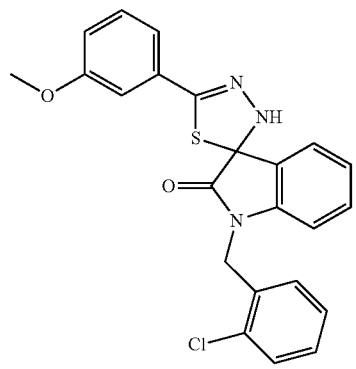

,

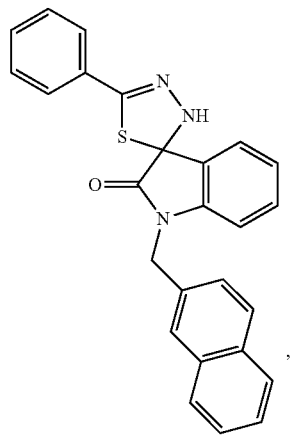

,

-continued

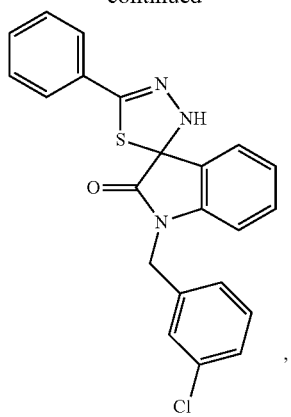

,

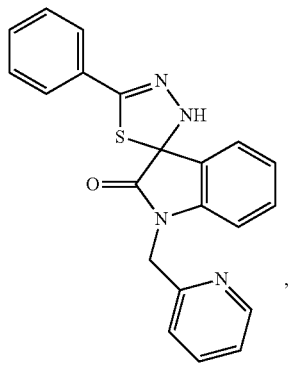

,

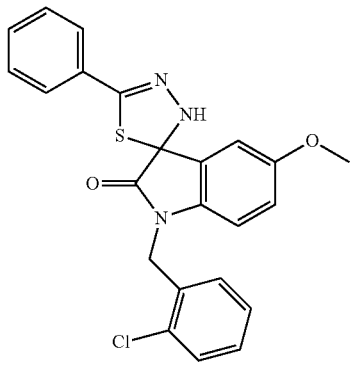

,

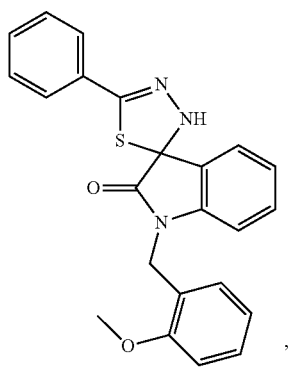

,

81
-continued
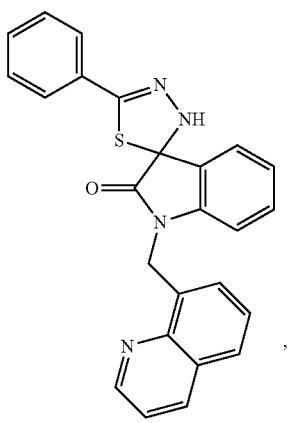
,
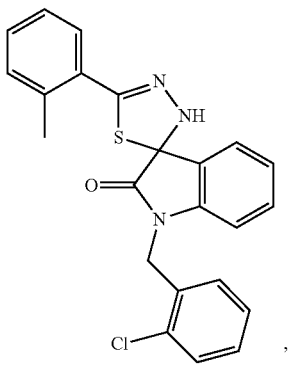
,
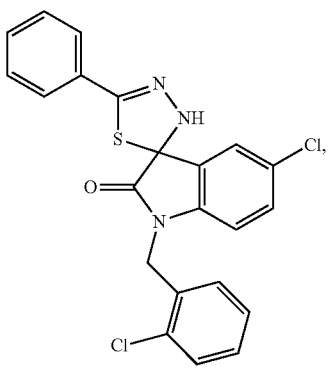
,
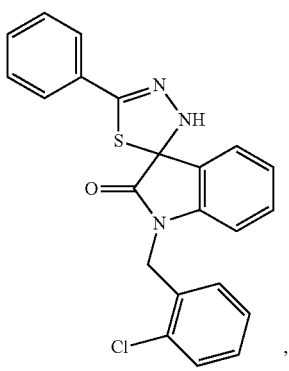
,
82
-continued
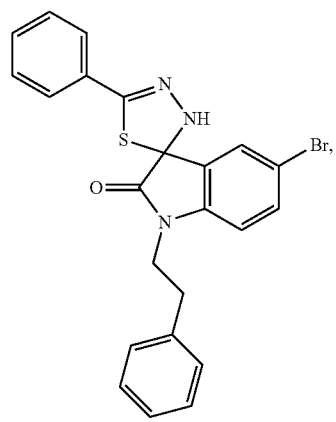
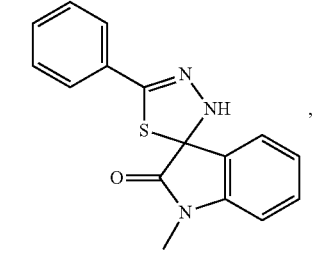
,
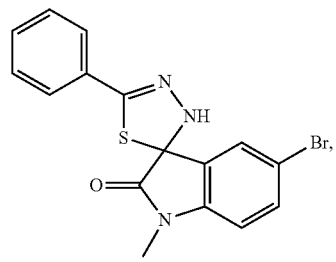
,
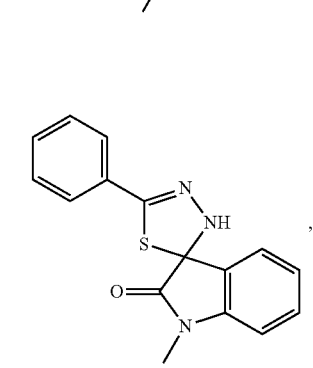
,
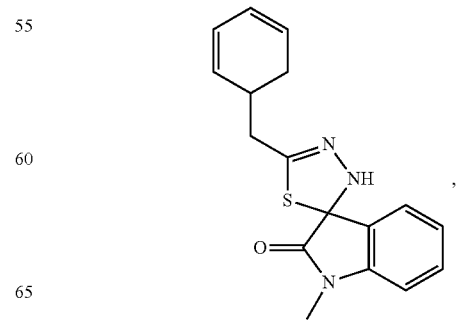
, -continued

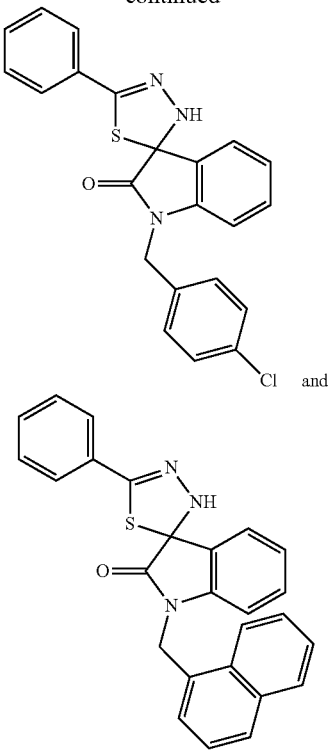

and pharmaceutically acceptable salts thereof.

16. The method of claim 8 wherein the cancer is breast cancer.

17. The method of claim 9 wherein the cancer is breast cancer.

18. The compound of claim 1 wherein $R^{1a}$ is H.

19. The compound of claim 1 wherein $R^{1b}$ is H.

20. The compound of claim 1 wherein at least one of $R^{1a}$ or $R^{1b}$ is independently selected from $(C_1-C_6)$alkyl, $(C_2-C_6)$alkenyl, $(C_2-C_6)$alkynyl, $(C_3-C_7)$carbocycle, halogen, —CN, —$NR_{n1}R_{r1}$, —$NR_{n1}COR_{p1}$, $NO_2$, —$C(O)R_{n1}$ and —$C(O)OR_{n1}$.

21. The compound of claim 1 wherein $R^1$ is phenyl, 3-chlorophenyl, 3-methoxyphenyl or 2-methylphenyl.

22. The compound of claim 1 wherein $R^3$ is benzyl wherein the benzyl is substituted with one or more groups selected from $Z^1$, $(C_1-C_6)$alkyl, $(C_2-C_6)$alkenyl and $(C_2-C_6)$alkynyl, or $R^3$ is substituted naphthylmethyl-, wherein the substituted naphthylmethyl- is substituted with one or more groups selected from $Z^1$, $(C_1-C_6)$alkyl, $(C_2-C_6)$alkenyl and $(C_2-C_6)$alkynyl and at least one of $R^{1a}$ ore is selected from $(C_1-C_6)$alkyl, $(C_2-C_6)$alkenyl, $(C_2-C_6)$alkynyl, $(C_3-C_7)$carbocycle, halogen, —CN, —$NR_{n1}R_{r1}$, —$NR_{n1}COR_{p1}$, $NO_2$, —$C(O)R_{n1}$ and —$C(O)OR_{n1}$; and the remaining $R^{1a}$ or $R^{1b}$ is selected from H, $(C_1-C_6)$alkyl, $(C_2-C_6)$alkenyl, $(C_2-C_6)$alkynyl, $(C_3-C_7)$carbocycle, halogen, —CN, —$NR_{n1}R_{r1}$, —$NR_{n1}COR_{p1}$, $NO_2$, —$C(O)R_{n1}$ and —$C(O)OR_{n1}$; or $R^3$ is unsubstituted naphthylmethyl- and at least one of $R^{1a}$ or $R^{1b}$ is independently selected from $(C_2-C_6)$alkenyl, $(C_2-C_6)$alkynyl, $(C_3-C_7)$carbocycle, halogen, —CN, —$NR_{n1}R_{r1}$, —$NR_{n1}COR_{p1}$, $NO_2$, —$C(O)R_{n1}$ and —$C(O)OR_{n1}$ and the remaining $R^{1a}$ or $R^{1b}$ is selected from H, $(C_1-C_6)$alkyl, $(C_2-C_6)$alkenyl, $(C_2-C_6)$alkynyl, $(C_3-C_7)$carbocycle, halogen, —CN, —$NR_{n1}R_{r1}$, —$NR_{n1}COR_{p1}$, $NO_2$, —$C(O)R_{n1}$ and —$C(O)OR_{n1}$.

23. The compound of claim 1 wherein $R^3$ is benzyl wherein the benzyl is substituted with one or more groups selected from $Z^1$, $(C_1-C_6)$alkyl, $(C_2-C_6)$alkenyl and $(C_2-C_6)$alkynyl.

24. The compound of claim 1 wherein $R^3$ is 2-chlorobenzyl, 2-methoxybenzyl, 3-chlorobenzyl, pyridine-2-ylmethyl or quinolin-8-ylmethyl.

* * * * *

UNITED STATES PATENT AND TRADEMARK OFFICE
CERTIFICATE OF CORRECTION

PATENT NO. : 9,598,441 B2
APPLICATION NO. : 14/239881
DATED : March 21, 2017
INVENTOR(S) : Arun K. Rishi and Scott D. Larsen It is certified that error appears in the above-identified patent and that said Letters Patent is hereby corrected as shown below:

In the Claims

Column 73, Line 1, Claim 1, please delete "-CN, -OR$_{a1}$, -NR$_{q1}$R$_{r1}$," and insert
-- -CN, -OR$_{n1}$, -NR$_{q1}$R$_{r1}$, --;

Column 73, Line 15, Claim 1, please delete "H, (C$_2$-C$_6$)alkenyl." and insert
-- H, (C$_1$-C$_6$)alkyl, (C$_2$-C$_6$)alkenyl. --;

Column 73, Line 51, Claim 1, please delete "R$_{q1}$ and R$_{n1}$ are" and insert -- R$_{q1}$ and R$_{r1}$ are --;

Column 73, Line 53, Claim 1, please delete "R$_{q1}$ and R$_{n1}$ together" and insert -- R$_{q1}$ and R$_{r1}$ together --;

Column 74, Line 24, Claim 1, please delete "Z$^1$, (C$_7$-C$_6$)alkenyl," and insert -- Z$^1$, (C$_2$-C$_6$)alkenyl, --;

Column 74, Lines 29-30, Claim 1, please delete "H, (C$_2$-C$_6$)alkenyl." and insert
-- H, (C$_1$-C$_6$)alkyl, (C$_2$-C$_6$)alkenyl. --;

Column 74, Line 30, Claim 1, please delete "(C$_3$-C$_2$)carbocycle" and insert -- (C$_3$-C$_7$)carbocycle --;

Column 74, Line 31, Claim 1, please delete "-NR$_n$COR$_{p1}$," and insert -- -NR$_{n1}$COR$_{p1}$, --;

Column 74, Line 34, Claim 1, please delete "from (C$_7$-C$_6$)alkenyl," and insert -- from
(C$_2$-C$_6$)alkenyl, --;

Column 74, Line 39, Claim 1, please delete "(C$_7$-C$_6$)alkynyl," and insert -- (C$_2$-C$_6$)alkynyl, --;

Column 74, Line 65, Claim 5, please delete "(C$_7$-C$_6$)alkynyl," and insert -- (C$_2$-C$_6$)alkynyl, --;

Column 78, Line 21, Claim 9, please delete "R$_{q1}$ and R$_{n1}$ are" and insert -- R$_{q1}$ and R$_{r1}$ are --;

Signed and Sealed this
Twenty-second Day of May, 2018

Andrei Iancu
*Director of the United States Patent and Trademark Office*

CERTIFICATE OF CORRECTION (continued)
U.S. Pat. No. 9,598,441 B2

Column 82, Lines 40-50, Claim 15, please delete the following structure:

" 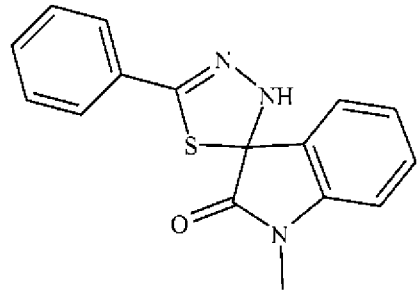 " and insert -- 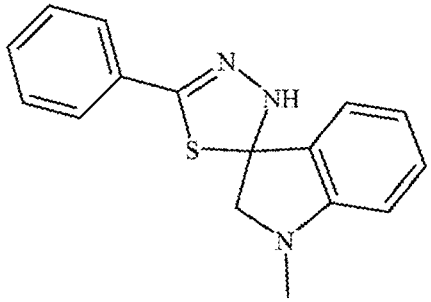 --;

Column 84, Line 5, Claim 20, please delete "-CN, -$NR_{n1}R_{r1}$, -$NR_{n1}COR_{p1}$," and insert -- -CN, -$OR_{n1}$, -$NR_{q1}R_{r1}$, -$NR_{n1}COR_{p1}$, --;

Column 84, Line 15, Claim 22, please delete "of $R^{1a}$ ore is" and insert -- of $R^{1a}$ or $R^{1b}$ is --;

Column 84, Line 17, Claim 22, please delete "-CN, -$NR_{n1}R_{r1}$, -$NR_{n1}COR_{p1}$," and insert -- -CN, -$OR_{n1}$, -$NR_{q1}R_{r1}$, -$NR_{n1}COR_{p1}$, --;

Column 84, Line 20, Claim 22, please delete "-CN, -$NR_{n1}R_{r1}$, -$NR_{n1}COR_{p1}$," and insert -- -CN, -$OR_{n1}$, -$NR_{q1}R_{r1}$, -$NR_{n1}COR_{p1}$, --;

Column 84, Line 24, Claim 22, please delete "-CN, -$NR_{n1}R_{r1}$, -$NR_{n1}COR_{p1}$," and insert -- -CN, -$OR_{n1}$, -$NR_{q1}R_{r1}$, -$NR_{n1}COR_{p1}$, --;

Column 84, Line 28, Claim 22, please delete "-CN, -$NR_{n1}R_{r1}$, -$NR_{n1}COR_{p1}$," and insert -- -CN, -$OR_{n1}$, -$NR_{q1}R_{r1}$, -$NR_{n1}COR_{p1}$, -- therefor.